US012807958B2

(12) United States Patent
Jones et al.

(10) Patent No.: US 12,807,958 B2
(45) Date of Patent: Nov. 24, 2026

(54) METHODS FOR THE PRODUCTION OF PSILOCYBIN AND INTERMEDIATES OR SIDE PRODUCTS

(71) Applicant: MIAMI UNIVERSITY, Oxford, OH (US)

(72) Inventors: J. Andrew Jones, Liberty Township, OH (US); Alexandra Adams, Liberty Township, OH (US); Nicholas Kaplan, Fort Wayne, IN (US)

(73) Assignee: Miami University, Oxford, OH (US)

( * ) Notice: Subject to any disclaimer, the term of this patent is extended or adjusted under 35 U.S.C. 154(b) by 1162 days.

(21) Appl. No.: 17/755,368

(22) PCT Filed: Sep. 18, 2020

(86) PCT No.: PCT/US2020/051543

§ 371 (c)(1),
(2) Date: Apr. 27, 2022

(87) PCT Pub. No.: WO2021/086513

PCT Pub. Date: May 6, 2021

(65) Prior Publication Data

US 2022/0372494 A1 Nov. 24, 2022

Related U.S. Application Data

(60) Provisional application No. 62/990,633, filed on Mar. 17, 2020, provisional application No. 62/926,875, filed on Oct. 28, 2019.

(51) Int. Cl.

*C12N 15/52* (2006.01)
*C12N 9/10* (2006.01)
*C12N 9/12* (2006.01)
*C12N 15/70* (2006.01)

(52) U.S. Cl.

CPC ........... *C12N 15/52* (2013.01); *C12N 9/1007* (2013.01); *C12N 9/1205* (2013.01); *C12N 15/70* (2013.01)

(58) Field of Classification Search

CPC .... C12N 15/52; C12N 9/1007; C12N 9/1205; C12N 15/70

See application file for complete search history.

(56) References Cited

U.S. PATENT DOCUMENTS 11,661,617 B2 * 5/2023 Protzko ................ C12N 9/0071 435/252.33
11,952,580 B2 * 4/2024 Mojzita .............. C12N 15/8243
2020/0165632 A1 * 5/2020 Qu ......................... C12N 15/86

FOREIGN PATENT DOCUMENTS

WO WO-2019173797 A1 * 9/2019 ..... C12Y 203/01087
WO WO-2019180309 A1 * 9/2019 ............ C12N 15/63

OTHER PUBLICATIONS

Fricke et al. (Fricke, J., Blei, F., & Hoffmeister, D. (2017). Enzymatic synthesis of psilocybin. Angewandte Chemie International Edition, 56(40), 12352-12355, see IDS filed Apr. 27, 2022, Cite No. 6) (Year: 2017).*
Jones et al. (Sci Rep. Jun. 11, 2015:5:11301. doi: 10.1038/srep11301.) (Year: 2015).*
Adams et al. "In Vivo Production of Psilocybin in *E Coli*" Metabolic Engineering vol. 56, pp. 111-119, (2019).
Supplementary Search Report from EP Application No. 20 88 2990 dated Mar. 27, 2024.
Search Report and Written Opinion for SG Application No. 11202204155Q, dated May 7, 2025.
First Office Action for CN Application No. 202080089926.6 with EN Translation, dated Apr. 22, 2025.
Restriction Requirement for PH Application No. 1-2022-550990 dated Aug. 6, 2025.
Certificate of Patent Renewal for NG/PT/PCT/2022/5988, dated Oct. 28, 2024.
Second Office Action for CN Application No. 202080089926.6 with EN Translation.
UnipProt Accession No. PODPA6 (PSID_PSICU), L-tryptophan decarboxylase, Oct. 25, 2017, 2, [online] [retrieved on Dec. 31, 2020]. Retrieved from <URL: https://www.UnipProt.org/UnipProt/PODPA6; nucleotides 1-439> Entire document Oct. 25, 2017.
UnipProt Accession No. PODPA8 (PSIK_PSICU), 4-hydroxytryptamine kinase, Oct. 25, 2017 [online], [retrieved on Dec. 31, 2020]. Retrieved from <URL: https://www.UnipProt.org/UnipProt/PODPA8; nucleotides 1-362> Entire document Oct. 25, 2017.
UnipProt Accession No. P0DPA9 (PSIM_PSICU), Psilocybin synthase, Oct. 25, 2017 [online], [retrieved on Dec. 31, 2020]. Retrieved from <URL: https://www.UnipProt.org/UnipProt/PODPA9; nucleotides 1-309> Entire document Oct. 25, 2017.
Fordjour, et al., Metabolic engineering of *Escherichia coli* BL21 (DE3) for de novo production of L-DOPA from D-glucose, Microbial Cell Factories, vol. 18, No. 74 Apr. 25, 2019.
Jones, J. A., et al., ePathOptimize: A Combinatorial Approach for Transcriptional Balancing of Metabolic Pathways, Sci Rep . Jun. 11, 2015.
Fricke, J., et al., Enzymatic synthesis of psilocybin. Angew. Chemie Int. 2017, Ed. 56, 12352-12355.
Xu, P., et al., ePathBrick: A synthetic biology platform for engineering metabolic pathways in *E. coli*. Biol., 2012, 1, 256-266.

(Continued)

*Primary Examiner* — Fereydoun G Sajjadi
*Assistant Examiner* — Joel D Levin
(74) *Attorney, Agent, or Firm* — Calfee, Halter & Griswold LLP

(57) ABSTRACT

Provided are methods, prokaryotic host cells, expression vectors, and kits for the production of psilocybin or an intermediate or a side product thereof. Also provided are methods, prokaryotic host cells, expression vectors, and kits for the production of norbaeocystin. In certain embodiments, the prokaryotic host cell is selected from the group consisting of *Escherichia coli, Corynebacterium glutamicum, Vibrio natriegens, Bacillus subtilis, Bacillus megaterium, Escherichia coli* Nissle 1917, *Clostridium acetobutlyicum, Streptomyces coelicolor, Lactococcus lactis, Pseudomonas putida, Streptomyces clavuligerus*, and *Streptomyces venezuelae.*

17 Claims, 40 Drawing Sheets

Specification includes a Sequence Listing.

(56) References Cited

OTHER PUBLICATIONS

International Search Report of PCT/US2020/051543, dated Feb. 9, 2021.
Written Opinion of PCT/US2020/051543, dated Feb. 9, 2021.
Notice of Publication with EN Translation for TH 2201002486, dated Mar. 6, 2026.
Office Action with EN Translation for CN 202080089926.6, dated Jan. 13, 2026.
Office Action for CA 3158505, dated Mar. 3, 2026.
Office Action for AU Application No. 2020374768, dated Oct. 15, 2025.
Office Action for PH Application No. 1-2022-550990 dated Nov. 7, 2025.
Notice of Allowance for PH 1-2022-550990, dated Mar. 10, 2026.
Notice of Acceptance for AU 2020374768, dated Feb. 16, 2026.
Office Action for MX/a/2022/004976 with English Translation, dated May 4, 2026.
Janis Fricke et al., “Enzymatic Synthesis of Psilocybin”, Angew. Chem. Int. Ed. 2017, vol. 56, pp. 12352-12355.
Janis Fricke et al., “Enzymatic Synthesis of Psilocybin”, Angewandte Chemie, Supporting Information, pp. 1-30.

* cited by examiner

Norbaeocystin

Baeocystin

Psilocybin

4OH-Trm

METHODS FOR THE PRODUCTION OF PSILOCYBIN AND INTERMEDIATES OR SIDE PRODUCTS

FIELD

The general inventive concepts relate to the field of medical therapeutics and more particularly to methods for the production of psilocybin and intermediates or side products, and methods for the production of norbaeocystin.

CROSS-REFERENCE TO RELATED APPLICATIONS

The instant application is a National Phase application of PCT/US2020/051543, filed Sep. 18, 2020, which is entitled to priority under 35 U.S.C. § 119 (e) to U.S. Provisional Application No. 62/926,875, filed Oct. 28, 2019 and to U.S. Provisional Application No. 62/990,633, filed Mar. 17, 2020, each of which is hereby incorporated by reference in its entirety.

SEQUENCE LISTING

The instant application contains a Sequence Listing which is submitted in ASCII format via EFS-Web and is hereby incorporated by reference in its entirety. The ASCII copy, created on Apr. 27, 2022, is named 315691-00038 Sequence Listing ST25.txt and is 39,701 bytes in size.

BACKGROUND

Because of its potential for treatment for a number of anxiety and mental-health related conditions, interest in psilocybin is significant. However, due to roadblocks in routing methods of obtaining drug targets (synthesis and/or extraction from a known biological source), large amounts are not currently available.

Psilocybin (4-phosphoryloxy-N,N-dimethyltryptamine) has gained attention in pharmaceutical markets as a result of recent clinical studies. The efficacy of psilocybin has been demonstrated for the treatment of anxiety in terminal cancer patients and alleviating the symptoms of post-traumatic stress disorder (PTSD). Most recently, the FDA has approved the first Phase IIb clinical trial for the use of psilocybin as a treatment for depression that is not well controlled with currently available interventions such as antidepressants and cognitive behavioral therapies.

Psilocybin was first purified from the Psilocybe *mexicana* mushroom by the Swiss chemist, Albert Hoffmann, in 1958. The first reports of the complete chemical synthesis of psilocybin were published in 1959; however, large-scale synthesis methods were not developed until the early 2000's by Shirota and colleagues at the National Institute of Sciences in Tokyo. Despite significant improvements over early synthetic routes, current methods remain tedious and costly, involving numerous intermediate separation and purification steps resulting in an overall yield of 49% from 4-hydroxyindole, incurring an estimated cost of $2 USD per milligram for pharmaceutical-grade psilocybin.

Much of the interest in psilocybin is due to its biosynthetic precursors—norbaeocystin and baeocystin. These compounds have structural similarity to the neurotransmitter serotonin and sparked the interest of researchers who were curious to understand the mechanism behind their hallucinogenic properties. After being named a Schedule I compound in the US with implementation of the Controlled Substance Act of 1970, research efforts involving psilocybin were abandoned for other less regulated bioactive molecules; however, experts in the field have suggested a reclassification to schedule IV would be appropriate if a psilocybin-containing medicine were to be approved in the future.

Clinical trials with psilocybin as a medication for individuals struggling with treatment-resistant depression are ongoing.

There remains a need for methods for the production of psilocybin and intermediates or side products thereof.

SUMMARY

The general inventive concepts relate to and contemplate methods and compositions for producing psilocybin or an intermediate or a side product thereof.

Provided is a method for the production of psilocybin or an intermediate or a side product thereof comprising contacting a prokaryotic host cell with one or more expression vectors, wherein each expression vector comprises a psilocybin production gene selected from the group consisting of psiD, psiK and psiM and combinations thereof; and culturing the host cell. In certain embodiments, the prokaryotic host cell is selected from the group consisting of *Escherichia coli, Corynebacterium glutamicum, Vibrio natriegens, Bacillus subtilis, Bacillus megaterium, Escherichia coli* Nissle 1917, *Clostridium* acetobutlyicum, *Streptomyces coelicolor, Lactococcus lactis, Pseudomonas putida, Streptomyces clavuligerus*, and *Streptomyces venezuelae.*

In some embodiments, the intermediate or side product of psilocybin is norbaeocystin, baeocystin, 4-hydroxytryptophan, 4-hydroxytryptamine, aeruginascin, psilocin, norpsilocin, or 4-hydroxy-N,N,N-trimethyltryptamonium (4-OH-TMT). In some embodiments the intermediate of psilocybin is norbaeocystin, baeocystin, 4-hydroxytryptophan, or 4-hydroxytryptamine. In some embodiments, the side product of psilocybin is aeruginascin, psilocin, norpsilocin, or 4-hydroxy-N,N,N-trimethyltryptamonium (4-OH-TMT).

Also provided is a recombinant prokaryotic cell comprising one or more expression vectors, wherein each expression vector comprises a psilocybin production gene selected from the group consisting of psiD, psiK and psiM and combinations thereof. Provided is a vector for introducing at least one gene associated with psilocybin production; the gene may be selected from: psiD, psiK, and psiM and combinations thereof. Also provided is a transfection kit comprising an expression vector as described herein.

Provided is a method for the production of norbaeocystin comprising contacting a prokaryotic host cell with one or more expression vectors, wherein each expression vector comprises a psilocybin production gene selected from the group consisting of psiD, psiK and combinations thereof; and culturing the host cell. In certain embodiments, none of the expression vectors comprises psiM. In certain embodiments, the prokaryotic host cell is selected from the group consisting of *Escherichia coli, Corynebacterium glutamicum, Vibrio natriegens, Bacillus subtilis, Bacillus megaterium, Escherichia coli* Nissle 1917, *Clostridium* acetobutlyicum, *Streptomyces coelicolor, Lactococcus lactis, Pseudomonas putida, Streptomyces clavuligerus*, and *Streptomyces venezuelae.*

Also provided is a recombinant prokaryotic cell comprising one or more expression vectors, wherein each expression vector comprises a psilocybin production gene selected from the group consisting of psiD, psiK, and combinations thereof. Provided is a vector for introducing at least one gene associated with psilocybin production; the gene may be selected from: psiD, psiK, and combinations thereof. Also provided is a transfection kit comprising an expression vector as described herein.

DESCRIPTION OF THE FIGURES

FIG. 1A shows a copy number library consisting of three plasmids with high (H), medium (M), and low (L) copy number. FIG. 1B shows a Pseudooperon library consisting of a promoter in front of each gene with a single terminator on the high copy number plasmid. FIG. 1C shows a basic operon library consisting of one promoter in front of all three genes on the high copy number plasmid. FIG. 1D shows Psilocybin biosynthesis pathway consisting of three heterologous enzymes, PsiD, PsiK, and PsiM, and highlighting the media supplements in yellow of serine and methionine (as described in the Examples). PsiD: L-tryptophan decarboxylase; PsiK: kinase; PsiM: S-adenosyl-L-methionine (SAM)-dependent N-methyltransferase; TrpB: tryptophan synthase beta subunit; Ser: serine; Met: methioinine; 1:4-hydroxyindole; 2: 4-hydroxytryptophan; 3: 4-hydroxytryptamine; 4: norbaeocystin; 5: baeocystin; 6: psilocybin.

FIG. 2A: Defined copy number library screening. The biosynthesis genes psiD, psiK, and psiM were expressed at either a high (H), medium (M), or low (L) copy number as indicated in the Examples. FIG. 2B: Pseudooperon library screening. The library provided very few mutant constructs with enhanced ability to produce psilocybin over levels previously achieved in the defined copy number library. FIG. 2C: Basic operon library screening. Significant enhancement of library performance was observed under the pseudooperon library. FIG. 2D: Additional screening of top mutants from operon library. The top 10 mutants from the operon library study were subjected to recloning and rescreening under standard conditions. Operon library clones #13 and #15 (FIG. 2D) demonstrated a large reduction in product titer and were identified as false positives in the original screen. Operon clone #16 (pPsilo16, purple) was selected for further study. All combinations were screened in 48-well plates under standard screening conditions and quantified using HPLC analysis. Error bars represent ±1 standard deviation from the mean of replicate samples. *Psilocybin not detected.

FIG. 3A shows induction point and temperature screening. The timing of IPTG induction was varied from 1 to 5 hours post inoculation. The data suggest reduced sensitivity to induction point but high sensitiviety to production phase temperature with increased production occurring at 37° C. FIG. 3B shows media, carbon source, and inducer concentration screening. A significant preference was shown for AMM with glucose as the carbon source. FIG. 3C shows effects of media supplementation on psilocybin titer. High sensitivity was observed for changes in the supplement concentration for 4-hydroxyindole, serine, and methionine. Error bars represent ±1 standard deviation from the mean of replicate samples.

FIG. 4A shows a comparison of intermediate and final product titers at various stages of optimization. Stage 1—Initial proof-of-concept All-High control, Stage 2—pPsilo16 post genetic optimization, Stage 3—pPsilo16 post genetic and fermentation optimization. Each additional screening stage further improved final production titer, mainly through reduction of intermediate product buildup. 4OH Ind: 4-hydroxyndole, 4OH-Trp: 4-hydroxytryptophan, 4OH Trm: 4-hydroxytryptamine. FIG. 4B shows fed-batch bioreactor scale up. Through careful monitoring of 4-hydroxyindole feed rate, the concentration of all intermediate products could be kept low resulting in improved growth and psilocybin titers. Error bars represent ±1 standard deviation from the mean of replicate samples.

FIG. 9B: Norbaeocystin. FIG. 9C: Baeocystin. FIG. 9D: Psilocybin. FIG. 9E: 4OH-Trm. FIG. 9F: 4OH-Trp. FIG. 9G: 4OH-Ind.

FIG. 17A: Measurement of dissolved oxygen (DO), pH, temperature, and agitation rate. FIG. 17B: Total cumulative glucose and ammonium phosphate dibasic fed. OD600 is also shown for reference. FIG. 17C: Total cumulative 4-hydroxyindole fed and 4-hydroxyindole feed rate for the bioreactor scale-up study. The feed rate represents the derivative for the cumulative amount fed. FIG. 17D: Total cumulative 4-hydroxyindole fed compared to psilocybin production for the bioreactor scale-up study. Transient product molar yield shows a maximum molar yield of 60% at roughly 48 hours and a final molar yield of 38% at the end of the scale-up study.

DETAILED DESCRIPTION

Figure 1A:
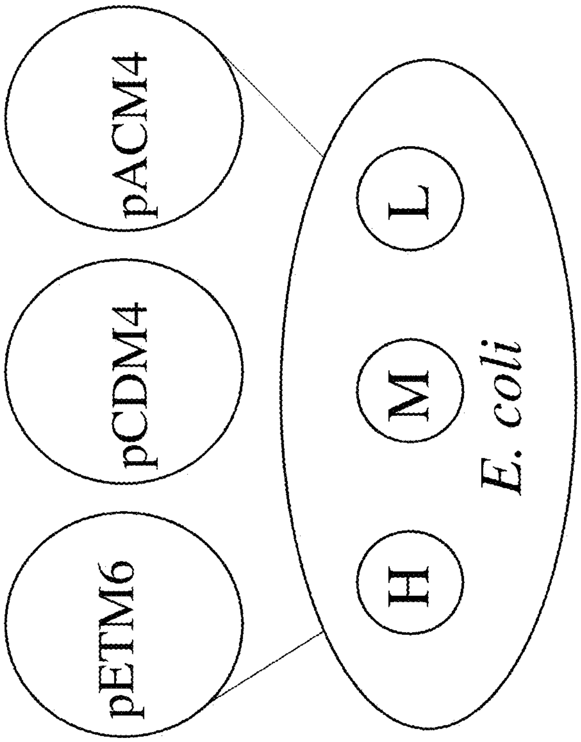
FIGS. 1A-1D show a summary of library configurations and biosynthesis pathway.

While the general inventive concepts are susceptible of embodiment in many forms, there are shown in the drawings, and will be described herein in detail, specific embodiments thereof with the understanding that the present disclosure is to be considered an exemplification of the principles of the general inventive concepts. Accordingly, the general inventive concepts are not intended to be limited to the specific embodiments illustrated herein.

It is also to be understood that the terminology used herein is for the purpose of describing particular embodiments only, and is not intended to be limiting.

The articles "a" and "an" are used herein to refer to one or more than one (i.e., to at least one) of the grammatical object of the article. By way of example, "a cell" means one cell or more than one cell.

"About" as used herein when referring to a measurable value such as an amount, a temporal duration, and the like, is meant to encompass variations of ±5%, preferably ±1%, and still more preferably ±0.1% from the specified value, as such variations are appropriate to perform the disclosed methods.

As used herein, the term "prokaryotic host cell" means a prokaryotic cell that is susceptible to transformation, transfection, transduction, or the like, with a nucleic acid construct or expression vector comprising a polynucleotide. The term "prokaryotic host cell" encompasses any progeny that is not identical due to mutations that occur during replication.

As used herein, the term "recombinant cell" or "recombinant host" means a cell or host cell that has been genetically modified or altered to comprise a nucleic acid sequence that is not native to the cell or host cell. In some embodiments the genetic modification comprises integrating the polynucleotide in the genome of the host cell. In further embodiments the polynucleotide is exogenous in the host cell.

As used herein, the term "intermediate" of psilocybin means an intermediate in the production or biosynthesis of psilocybin, e.g., norbaeocystin, baeocystin, 4-hydroxytryptophan, 4-hydroxytryptamine.

As used herein, the term "side product" of psilocybin means a side product in the production or biosynthesis of psilocybin, e.g., aeruginascin, psilocin, norpsilocin, or 4-hydroxy-N,N,N-trimethyltryptamonium (4-OH-TMT).

The materials, compositions, and methods described herein are intended to be used to provide novel routes for the production of psilocybin and intermediates or side products, and methods for the production of norbaeocystin.

Despite advances in the chemical synthesis of psilocybin, current methodologies struggle to provide sufficient material in a cost-effective manner. New advancements fueled Applicant's interest in developing a more cost-effective and easily manipulated host for the biosynthetic production of psilocybin.

Figure 1B:
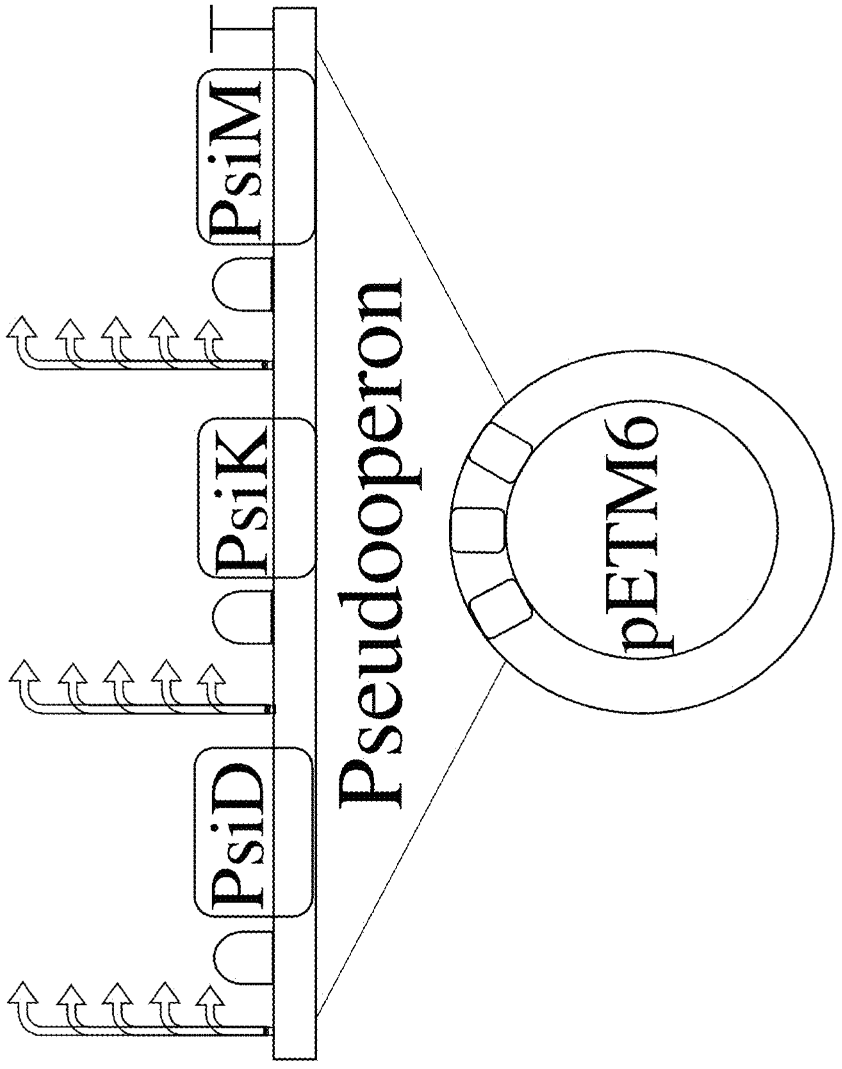
Figure 1C:
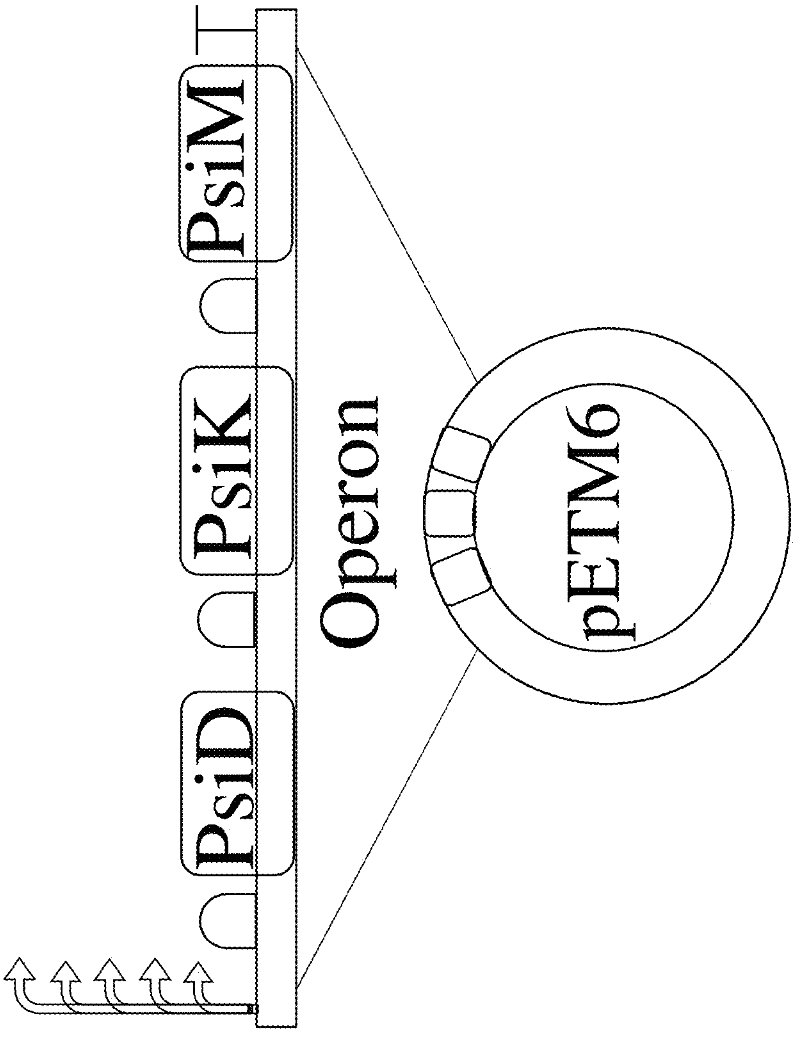
Figure 1D:
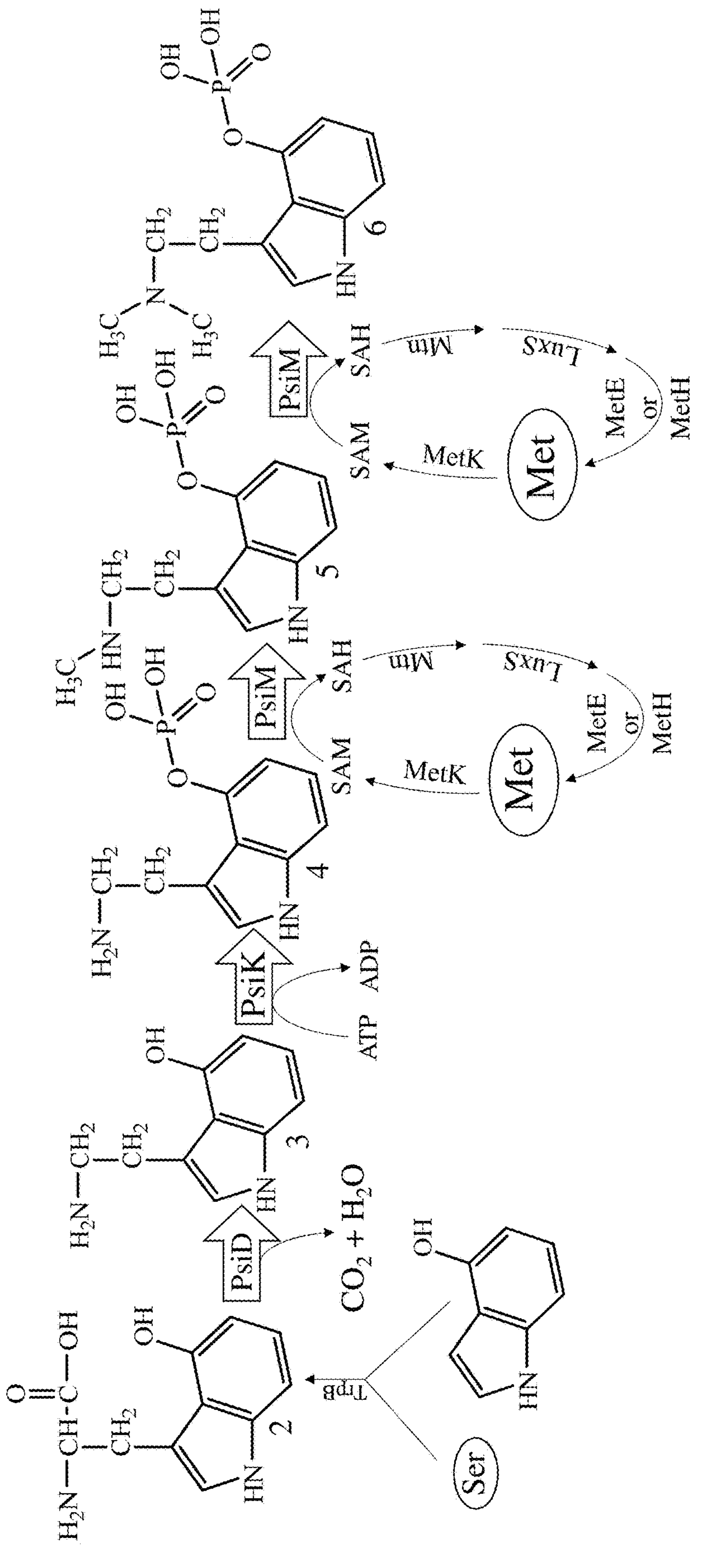

Utilizing the recently identified gene sequences from *P. cubensis* encoding an L-tryptophan decarboxylase (PsiD), a kinase (PsiK), and an S-adenosyl-L-methionine (SAM)-dependent N-methyltransferase (PsiM), together with the promiscuity of the native *Escherichia coli* tryptophan synthase (TrpAB), the biosynthesis pathway capable of psilocybin production from 4-hydroxyindole, was expressed in the prokaryotic model organism *E. coli* BL21 Star™ (DE3) (FIG. 1D).

There is an unmet need for large scale production and isolation of psilocybin. To address these limitations, a series of 3 parallel genetic screening methods were utilized, including: (1) a defined three-level copy number library, (2) a random 5-member operon library, and (3) a random 125-member pseudooperon library. After transcriptional optimization methods were employed, the best strain, pPsilo16, underwent a thorough review and revision of fermentation conditions, resulting in the production of ~139±2.7 mg/L of psilocybin from 4-hydroxyindole. Upon further work, a fed-batch bioreactor scale-up resulted in the production of 1160 mg/L of psilocybin, the highest titer reported to date from a recombinant host. Accordingly, the general inventive concepts relate to a novel production pathway and new cell line according to this procedure.

I. Methods, Vectors, Host Cells and Kits for the Production of Psilocybin or an Intermediate or a Side Product Thereof Methods Provided herein are the first known methods of in vivo psilocybin production using a prokaryotic host. Furthermore, the general inventive concepts are based, in part, on the surprising synergy between increased production through genetic and fermentation means to quickly identify key process parameters required to enable successful scale-up studies culminating in gram scale production of a high-value chemical product.

Provided is a method for the production of psilocybin or an intermediate or a side product thereof. The method comprises contacting a host cell with at least one psilocybin production gene selected from: psiD, psiK, psiM, and combinations thereof to form a recombinant cell; culturing the recombinant cell; and obtaining the psilocybin. In certain embodiments, the host cell is a prokaryotic cell. In certain exemplary embodiments, the host cell is an *E. coli* cell.

Provided is a method for the production of psilocybin or an intermediate or a side product thereof comprising contacting a prokaryotic host cell with one or more expression vectors, wherein each expression vector comprises a psilocybin production gene selected from the group consisting of psiD, psiK and psiM and combinations thereof; and culturing the host cell. In certain embodiments, the prokaryotic host cell is selected from the group consisting of *Escherichia*

*coli*, *Corynebacterium glutamicum*, *Vibrio natriegens*, *Bacillus subtilis*, *Bacillus megaterium*, *Escherichia coli* Nissle 1917, *Clostridium* acetobutlyicum, *Streptomyces coelicolor*, *Lactococcus lactis*, *Pseudomonas putida*, *Streptomyces clavuligerus*, and *Streptomyces venezuelae*.

In certain embodiments, the psiD comprises the amino acid sequence of SEQ ID NO: 8 or a sequence having at least 60%, at least 70%, at least 80%, at least 90%, at least 95%, at least 96%, at least 97%, at least 98%, or at least 99% sequence identity thereto. In certain embodiments, the psiD comprises the amino acid sequence of Genbank accession number KY984101.1 or a sequence having at least 60%, at least 70%, at least 80%, at least 90%, at least 95%, at least 96%, at least 97%, at least 98%, or at least 99% sequence identity thereto. In certain embodiments, the psiD is encoded by a nucleotide sequence comprising SEQ ID NO: 5 or a sequence having at least 60%, at least 70%, at least 80%, at least 90%, at least 95%, at least 96%, at least 97%, at least 98%, or at least 99% sequence identity thereto.

In certain embodiments, the psiK comprises the amino acid sequence of SEQ ID NO: 9 or a sequence having at least 60%, at least 70%, at least 80%, at least 90%, at least 95%, at least 96%, at least 97%, at least 98%, or at least 99% sequence identity thereto. In certain embodiments, the psiK comprises the amino acid sequence of Genbank accession number KY984099.1 or a sequence having at least 60%, at least 70%, at least 80%, at least 90%, at least 95%, at least 96%, at least 97%, at least 98%, or at least 99% sequence identity thereto. In certain embodiments, the psiK is encoded by a nucleotide sequence comprising SEQ ID NO: 6 or a sequence having at least 60%, at least 70%, at least 80%, at least 90%, at least 95%, at least 96%, at least 97%, at least 98%, or at least 99% sequence identity thereto.

In certain embodiments, the psiM comprises the amino acid sequence of SEQ ID NO: 10 or a sequence having at least 60%, at least 70%, at least 80%, at least 90%, at least 95%, at least 96%, at least 97%, at least 98%, or at least 99% sequence identity thereto. In certain embodiments, the psiM comprises the amino acid sequence of Genbank accession number KY984100.1 or a sequence having at least 60%, at least 70%, at least 80%, at least 90%, at least 95%, at least 96%, at least 97%, at least 98%, or at least 99% sequence identity thereto. In certain embodiments, the psiM is encoded by a nucleotide sequence comprising SEQ ID NO: 7 or a sequence having at least 60%, at least 70%, at least 80%, at least 90%, at least 95%, at least 96%, at least 97%, at least 98%, or at least 99% sequence identity thereto.

In certain embodiments, the prokaryotic cell is contacted with an expression vector comprising a psiD gene, a psiK gene and a psiM gene all under control of a single promoter in operon configuration. In certain embodiments, the prokaryotic cell is contacted with an expression vector comprising a psiD gene, a psiK gene and a psiM gene, wherein each gene is under control of a separate promoter in pseudooperon configuration. In certain embodiments, each gene is in monocistronic configuration, wherein each gene has a promoter and a terminator. Any configuration or arrangement of promoters and terminators is envisaged.

In some embodiments, the promoter is selected from the group consisting of G6 mutant T7, H9 mutant T7, H10 mutant T7, C4 mutant T7, consensus T7, Lac, Lac UV5, tac, trc, GAP, and xylA promoter.

It is envisaged that any intermediate or side product of psilocybin may be produced by any of the methods described herein. In some embodiments, the intermediate or side product of psilocybin is norbaeocystin, baeocystin, 4-hydroxytryptophan, 4-hydroxytryptamine, aeruginascin, psilocin, norpsilocin, or 4-hydroxy-N,N,N-trimethyltryptamonium (4-OH-TMT). In some embodiments the intermediate of psilocybin is norbaeocystin, baeocystin, 4-hydroxytryptophan, or 4-hydroxytryptamine. In some embodiments, the side product of psilocybin is aeruginascin, psilocin, norpsilocin, or 4-hydroxy-N,N,N-trimethyltryptamonium (4-OH-TMT).

In certain embodiments, the host cell is cultured with a supplement independently selected from the group consisting of 4-hydroxyindole, serine, methionine, 4-hydroxytryptophan, 4-hydroxytryptamine, and combinations thereof. In certain exemplary embodiments, the supplement is fed continuously to the host cell. In further embodiments, the host cell is grown in an actively growing culture. Continuous feeding is accomplished by using a series of syringe and/or peristaltic pumps whose outlet flow is directly connected to the bioreactor. The set point of these supplement addition pumps is adjusted in response to real-time measurement of cell biomass and specific metabolic levels using UV-vis absorption and HPLC analysis, respectively. The fed-batch fermentation process is focused on maximizing production of target metabolites through harnessing the ability of an actively growing and replicating cell culture to regenerate key co-factors and precursors which are critical to the biosynthesis of target metabolites. This process notably does not involve the centrifugal concentration and reconstitution of cell biomass to artificially higher cell density and/or into production media that was not used to build the initial biomass. The production process involves the inoculation of the reactor from an overnight preculture at low optical density, followed by exponential phase growth entering into a fed-batch phase of production, culminating in a high cell density culture.

The psilocybin and intermediate or side products are found extracellularly in the fermentation broth. In certain embodiments, the psilocybin and intermediate or side products are isolated. These target products can be collected through drying the fermentation broth after centrifugation to remove the cell biomass. The resulting dry product can be extracted to further purify the target compounds. Alternatively, the products can be extracted from the liquid cell culture broth using a solvent which is immiscible with water and partitions psilocybin or any of the intermediate or side products into the organic phase. Furthermore, contaminants from the fermentation broth can be removed through extraction leaving the psilocybin and/or intermediate or side products in the aqueous phase for collection after drying or crystallization procedures.

In certain embodiments, the methods described herein result in a titer of psilocybin of about 0.5 to about 50 g/L. In some embodiments, the methods described herein result in a titer of psilocybin of about 0.5 to about 10 g/L. In yet further embodiments, the methods described herein result in a titer of psilocybin of about 0.5 to about 2 g/L. In certain embodiments, the methods described herein result in a titer of psilocybin of about 1.0 to about 1.2 g/L. In further embodiments, the methods described herein result in a titer of psilocybin of about 1.16 g/L.

In certain embodiments, the methods described herein result in a molar yield of psilocybin of about 10% to about 100%. In some embodiments, the methods described herein result in a molar yield of psilocybin of about 20% to about 80%. In yet further embodiments, the methods described herein result in a molar yield of psilocybin of about 30% to about 70%. In certain embodiments, the methods described herein result in a molar yield of psilocybin of about 40% to about 60%. In further embodiments, the methods described herein result in a molar yield of psilocybin of about 50%.

Recombinant Prokaryotic Cells for the Production of Psilocybin or an Intermediate or a Side Product Thereof Provided is a recombinant prokaryotic cell comprising one or more expression vectors, wherein each expression vector comprises a psilocybin production gene selected from the group consisting of psiD, psiK and psiM and combinations thereof.

In certain embodiments, the recombinant prokaryotic cell is selected from the group consisting of *Escherichia coli, Corynebacterium glutamicum, Vibrio natriegens, Bacillus subtilis, Bacillus megaterium, Escherichia coli* Nissle 1917, *Clostridium* acetobutlyicum, *Streptomyces coelicolor, Lactococcus lactis, Pseudomonas putida, Streptomyces clavuligerus*, and *Streptomyces venezuelae*.

In certain embodiments, the psiD comprises the amino acid sequence of SEQ ID NO: 8 or a sequence having at least 60%, at least 70%, at least 80%, at least 90%, at least 95%, at least 96%, at least 97%, at least 98%, or at least 99% sequence identity thereto. In certain embodiments, the psiD comprises the amino acid sequence of Genbank accession number KY984101.1 or a sequence having at least 60%, at least 70%, at least 80%, at least 90%, at least 95%, at least 96%, at least 97%, at least 98%, or at least 99% sequence identity thereto. In certain embodiments, the psiD is encoded by a nucleotide sequence comprising SEQ ID NO: 5 or a sequence having at least 60%, at least 70%, at least 80%, at least 90%, at least 95%, at least 96%, at least 97%, at least 98%, or at least 99% sequence identity thereto.

In certain embodiments, the psiK comprises the amino acid sequence of SEQ ID NO: 9 or a sequence having at least 60%, at least 70%, at least 80%, at least 90%, at least 95%, at least 96%, at least 97%, at least 98%, or at least 99% sequence identity thereto. In certain embodiments, the psiK comprises the amino acid sequence of Genbank accession number KY984099.1 or a sequence having at least 60%, at least 70%, at least 80%, at least 90%, at least 95%, at least 96%, at least 97%, at least 98%, or at least 99% sequence identity thereto. In certain embodiments, the psiK is encoded by a nucleotide sequence comprising SEQ ID NO: 6 or a sequence having at least 60%, at least 70%, at least 80%, at least 90%, at least 95%, at least 96%, at least 97%, at least 98%, or at least 99% sequence identity thereto.

In certain embodiments, the psiM comprises the amino acid sequence of SEQ ID NO: 10 or a sequence having at least 60%, at least 70%, at least 80%, at least 90%, at least 95%, at least 96%, at least 97%, at least 98%, or at least 99% sequence identity thereto. In certain embodiments, the psiM comprises the amino acid sequence of Genbank accession number KY984100.1 or a sequence having at least 60%, at least 70%, at least 80%, at least 90%, at least 95%, at least 96%, at least 97%, at least 98%, or at least 99% sequence identity thereto. In certain embodiments, the psiM is encoded by a nucleotide sequence comprising SEQ ID NO: 7 or a sequence having at least 60%, at least 70%, at least 80%, at least 90%, at least 95%, at least 96%, at least 97%, at least 98%, or at least 99% sequence identity thereto.

In certain embodiments, the prokaryotic cell is contacted with an expression vector comprising a psiD gene, a psiK gene and a psiM gene all under control of a single promoter in operon configuration. In certain embodiments, the prokaryotic cell is contacted with an expression vector comprising a psiD gene, a psiK gene and a psiM gene, wherein each gene is under control of a separate promoter in pseudooperon configuration. In certain embodiments, each gene is in monocistronic configuration, wherein each gene has a promoter and a terminator. Any configuration or arrangement of promoters and terminators is envisaged.

In some embodiments, the promoter is selected from the group consisting of G6 mutant T7, H9 mutant T7, H10 mutant T7, C4 mutant T7, consensus T7, Lac, Lac UV5, tac, trc, GAP, and xylA promoter.

Expression Vectors

Provided is a vector for introducing at least one gene associated with psilocybin production; the gene may be selected from: psiD, psiK, and psiM and combinations thereof.

In certain embodiments, the psiD comprises the amino acid sequence of SEQ ID NO: 8 or a sequence having at least 60%, at least 70%, at least 80%, at least 90%, at least 95%, at least 96%, at least 97%, at least 98%, or at least 99% sequence identity thereto. In certain embodiments, the psiD comprises the amino acid sequence of Genbank accession number KY984101.1 or a sequence having at least 60%, at least 70%, at least 80%, at least 90%, at least 95%, at least 96%, at least 97%, at least 98%, or at least 99% sequence identity thereto. In certain embodiments, the psiD is encoded by a nucleotide sequence comprising SEQ ID NO: 5 or a sequence having at least 60%, at least 70%, at least 80%, at least 90%, at least 95%, at least 96%, at least 97%, at least 98%, or at least 99% sequence identity thereto.

In certain embodiments, the psiK comprises the amino acid sequence of SEQ ID NO: 9 or a sequence having at least 60%, at least 70%, at least 80%, at least 90%, at least 95%, at least 96%, at least 97%, at least 98%, or at least 99% sequence identity thereto. In certain embodiments, the psiK comprises the amino acid sequence of Genbank accession number KY984099.1 or a sequence having at least 60%, at least 70%, at least 80%, at least 90%, at least 95%, at least 96%, at least 97%, at least 98%, or at least 99% sequence identity thereto. In certain embodiments, the psiK is encoded by a nucleotide sequence comprising SEQ ID NO: 6 or a sequence having at least 60%, at least 70%, at least 80%, at least 90%, at least 95%, at least 96%, at least 97%, at least 98%, or at least 99% sequence identity thereto.

In certain embodiments, the psiM comprises the amino acid sequence of SEQ ID NO: 10 or a sequence having at least 60%, at least 70%, at least 80%, at least 90%, at least 95%, at least 96%, at least 97%, at least 98%, or at least 99% sequence identity thereto. In certain embodiments, the psiM comprises the amino acid sequence of Genbank accession number KY984100.1 or a sequence having at least 60%, at least 70%, at least 80%, at least 90%, at least 95%, at least 96%, at least 97%, at least 98%, or at least 99% sequence identity thereto. In certain embodiments, the psiM is encoded by a nucleotide sequence comprising SEQ ID NO: 7 or a sequence having at least 60%, at least 70%, at least 80%, at least 90%, at least 95%, at least 96%, at least 97%, at least 98%, or at least 99% sequence identity thereto.

In certain embodiments, the expression vector comprises a psiD gene, a psiK gene and a psiM gene all under control of a single promoter in operon configuration. In certain embodiments, the expression vector comprises a psiD gene, a psiK gene and a psiM gene, wherein each gene is under control of a separate promoter in pseudooperon configuration. In certain embodiments, each gene is in monocistronic configuration, wherein each gene has a promoter and a terminator. Any configuration or arrangement of promoters and terminators is envisaged.

In certain embodiments, the expression vector comprises the nucleic acid sequence of SEQ ID NO: 22 or a sequence having at least 60%, at least 70%, at least 80%, at least 90%, at least 95%, at least 96%, at least 97%, at least 98%, or at least 99% sequence identity thereto. In certain embodiments, the expression vector is pPsilo16 or a vector having at least 60%, at least 70%, at least 80%, at least 90%, at least 95%, at least 96%, at least 97%, at least 98%, or at least 99% sequence identity thereto.

In some embodiments, the promoter is selected from the group consisting of G6 mutant T7, H9 mutant T7, H10 mutant T7, C4 mutant T7, consensus T7, Lac, Lac UV5, tac, trc, GAP, and xylA promoter.

Kits

Provided is a transfection kit comprising an expression vector as described herein. Such a kit may comprise a carrying means being compartmentalized to receive in close confinement one or more container means such as, e.g., vials or test tubes. Each of such container means comprises components or a mixture of components needed to perform a transfection. Such kits may include, for example, one or more components selected from vectors, cells, reagents, lipid-aggregate forming compounds, transfection enhancers, or biologically active molecules.

II. Methods, Vectors, Host Cells and Kits for the Production of Norbaeocystin

Methods

Provided is a method for the production of norbaeocystin comprising contacting a prokaryotic host cell with one or more expression vectors, wherein each expression vector comprises a psilocybin production gene selected from the group consisting of psiD, psiK and combinations thereof; and culturing the host cell. In certain embodiments, none of the expression vectors comprises psiM.

In certain embodiments, the psiD comprises the amino acid sequence of SEQ ID NO: 8 or a sequence having at least 60%, at least 70%, at least 80%, at least 90%, at least 95%, at least 96%, at least 97%, at least 98%, or at least 99% sequence identity thereto. In certain embodiments, the psiD comprises the amino acid sequence of Genbank accession number KY984101.1 or a sequence having at least 60%, at least 70%, at least 80%, at least 90%, at least 95%, at least 96%, at least 97%, at least 98%, or at least 99% sequence identity thereto. In certain embodiments, the psiD is encoded by a nucleotide sequence comprising SEQ ID NO: 5 or a sequence having at least 60%, at least 70%, at least 80%, at least 90%, at least 95%, at least 96%, at least 97%, at least 98%, or at least 99% sequence identity thereto.

In certain embodiments, the psiK comprises the amino acid sequence of SEQ ID NO: 9 or a sequence having at least 60%, at least 70%, at least 80%, at least 90%, at least 95%, at least 96%, at least 97%, at least 98%, or at least 99% sequence identity thereto. In certain embodiments, the psiK comprises the amino acid sequence of Genbank accession number KY984099.1 or a sequence having at least 60%, at least 70%, at least 80%, at least 90%, at least 95%, at least 96%, at least 97%, at least 98%, or at least 99% sequence identity thereto. In certain embodiments, the psiK is encoded by a nucleotide sequence comprising SEQ ID NO: 6 or a sequence having at least 60%, at least 70%, at least 80%, at least 90%, at least 95%, at least 96%, at least 97%, at least 98%, or at least 99% sequence identity thereto.

In certain embodiments, the recombinant prokaryotic cell is selected from the group consisting of *Escherichia coli, Corynebacterium glutamicum, Vibrio natriegens, Bacillus subtilis, Bacillus megaterium, Escherichia coli* Nissle 1917, *Clostridium* acetobutlyicum, *Streptomyces coelicolor, Lactococcus lactis, Pseudomonas putida, Streptomyces clavuligerus*, and *Streptomyces venezuelae.*

In certain embodiments, the prokaryotic cell is contacted with an expression vector comprising a psilocybin production gene selected from the group consisting of a psiD gene, a psiK gene, and combinations thereof, all under control of a single promoter in operon configuration. In certain embodiments, the prokaryotic cell is contacted with an expression vector comprising a psiD gene and a psiK gene, wherein each gene is under control of a separate promoter in pseudooperon configuration. In certain embodiments, each gene is in monocistronic configuration, wherein each gene has a promoter and a terminator. Any configuration or arrangement of promoters and terminators is envisaged. In certain embodiments, none of the expression vectors comprises a psiM gene.

In some embodiments, the promoter is selected from the group consisting of G6 mutant T7, H9 mutant T7, H10 mutant T7, C4 mutant T7, consensus T7, Lac, Lac UV5, tac, trc, GAP, and xylA promoter.

In certain embodiments, the host cell is cultured with a supplement independently selected from the group consisting of 4-hydroxyindole, serine, methionine, 4-hydroxytryptophan, 4-hydroxytryptamine, and combinations thereof. In certain exemplary embodiments, the supplement is fed continuously to the host cell. In further embodiments, the host cell is grown in an actively growing culture. Continuous feeding is accomplished by using a series of syringe and/or peristaltic pumps whose outlet flow is directly connected to the bioreactor. The set point of these supplement addition pumps is adjusted in response to real-time measurement of cell biomass and specific metabolic levels using UV-vis absorption and HPLC analysis, respectively. The fed-batch fermentation process is focused on maximizing production of target metabolites through harnessing the ability of an actively growing and replicating cell culture to regenerate key co-factors and precursors which are critical to the biosynthesis of target metabolites. This process notably does not involve the centrifugal concentration and reconstitution of cell biomass to artificially higher cell density and/or into production media that was not used to build the initial biomass. The production process involves the inoculation of the reactor from an overnight preculture at low optical density, followed by exponential phase growth entering into a fed-batch phase of production, culminating in a high cell density culture.

The norbaeocystin is found extracellularly in the fermentation broth. In certain embodiments, the norbaeocystin is isolated. Norbaeocystin can be collected through drying the fermentation broth after centrifugation to remove the cell biomass. The resulting dry product can be extracted to further purify the norbaeocystin. Alternatively, the norbaeocystin can be extracted from the liquid cell culture broth using a solvent which is immiscible with water and partitions norbaeocystin into the organic phase. Furthermore, contaminants from the fermentation broth can be removed through extraction leaving the norbaeocystin in the aqueous phase for collection after drying or crystallization procedures.

In certain embodiments, the methods described herein result in a titer of norbaeocystin of about 0.1 to about 50 g/L. In some embodiments, the methods described herein result in a titer of norbaeocystin of about 0.1 to about 10 g/L. In yet further embodiments, the methods described herein result in a titer of norbaeocystin of about 0.1 to about 2 g/L. In certain embodiments, the methods described herein result in a titer of norbaeocystin of about 0.1 to about 1.0 g/L. In further embodiments, the methods described herein result in a titer of norbaeocystin of about 0.4 to about 0.8 g/L. In further embodiments, the methods described herein result in a titer of norbaeocystin of about 0.7 g/L.

In certain embodiments, the methods described herein result in a molar yield of norbaeocystin of about 10% to about 100%. In some embodiments, the methods described herein result in a molar yield of norbaeocystin of about 20% to about 80%. In yet further embodiments, the methods described herein result in a molar yield of norbaeocystin of about 30% to about 70%. In certain embodiments, the methods described herein result in a molar yield of norbaeocystin of about 40% to about 60%. In further embodiments, the methods described herein result in a molar yield of norbaeocystin of about 50%.

Recombinant Prokaryotic Cells for the Production of Norbaeocystin

Provided is a recombinant prokaryotic cell comprising one or more expression vectors, wherein each expression vector comprises a psilocybin production gene selected from the group consisting of psiD, psiK, and combinations thereof. In certain embodiments, none of the expression vectors comprises psiM.

In certain embodiments, the recombinant prokaryotic cell is selected from the group consisting of *Escherichia coli, Corynebacterium glutamicum, Vibrio natriegens, Bacillus subtilis, Bacillus megaterium, Escherichia coli* Nissle 1917, *Clostridium* acetobutlyicum, *Streptomyces coelicolor, Lactococcus lactis, Pseudomonas putida, Streptomyces clavuligerus*, and *Streptomyces venezuelae.*

In certain embodiments, the psiD comprises the amino acid sequence of SEQ ID NO: 8 or a sequence having at least 60%, at least 70%, at least 80%, at least 90%, at least 95%, at least 96%, at least 97%, at least 98%, or at least 99% sequence identity thereto. In certain embodiments, the psiD comprises the amino acid sequence of Genbank accession number KY984101.1 or a sequence having at least 60%, at least 70%, at least 80%, at least 90%, at least 95%, at least 96%, at least 97%, at least 98%, or at least 99% sequence identity thereto. In certain embodiments, the psiD is encoded by a nucleotide sequence comprising SEQ ID NO: 5 or a sequence having at least 60%, at least 70%, at least 80%, at least 90%, at least 95%, at least 96%, at least 97%, at least 98%, or at least 99% sequence identity thereto.

In certain embodiments, the psiK comprises the amino acid sequence of SEQ ID NO: 9 or a sequence having at least 60%, at least 70%, at least 80%, at least 90%, at least 95%, at least 96%, at least 97%, at least 98%, or at least 99% sequence identity thereto. In certain embodiments, the psiK comprises the amino acid sequence of Genbank accession number KY984099.1 or a sequence having at least 60%, at least 70%, at least 80%, at least 90%, at least 95%, at least 96%, at least 97%, at least 98%, or at least 99% sequence identity thereto. In certain embodiments, the psiK is encoded by a nucleotide sequence comprising SEQ ID NO: 6 or a sequence having at least 60%, at least 70%, at least 80%, at least 90%, at least 95%, at least 96%, at least 97%, at least 98%, or at least 99% sequence identity thereto.

In certain embodiments, the prokaryotic cell is contacted with an expression vector comprising a psiD gene and a psiK gene all under control of a single promoter in operon configuration. In certain embodiments, the prokaryotic cell is contacted with an expression vector comprising a psiD gene and a psiK gene, wherein each gene is under control of a separate promoter in pseudooperon configuration. In certain embodiments, each gene is in monocistronic configuration, wherein each gene has a promoter and a terminator. Any configuration or arrangement of promoters and terminators is envisaged. In certain embodiments, none of the expression vectors comprises a psiM gene.

In some embodiments, the promoter is selected from the group consisting of G6 mutant T7, H9 mutant T7, H10 mutant T7, C4 mutant T7, consensus T7, Lac, Lac UV5, tac, trc, GAP, and xylA promoter.

Expression Vectors

Provided is a vector for introducing at least one gene associated with psilocybin production; the gene may be selected from: psiD, psiK, and combinations thereof.

In certain embodiments, the psiD comprises the amino acid sequence of SEQ ID NO: 8 or a sequence having at least 60%, at least 70%, at least 80%, at least 90%, at least 95%, at least 96%, at least 97%, at least 98%, or at least 99% sequence identity thereto. In certain embodiments, the psiD comprises the amino acid sequence of Genbank accession number KY984101.1 or a sequence having at least 60%, at least 70%, at least 80%, at least 90%, at least 95%, at least 96%, at least 97%, at least 98%, or at least 99% sequence identity thereto. In certain embodiments, the psiD is encoded by a nucleotide sequence comprising SEQ ID NO: 5 or a sequence having at least 60%, at least 70%, at least 80%, at least 90%, at least 95%, at least 96%, at least 97%, at least 98%, or at least 99% sequence identity thereto.

In certain embodiments, the psiK comprises the amino acid sequence of SEQ ID NO: 9 or a sequence having at least 60%, at least 70%, at least 80%, at least 90%, at least 95%, at least 96%, at least 97%, at least 98%, or at least 99% sequence identity thereto. In certain embodiments, the psiK comprises the amino acid sequence of Genbank accession number KY984099.1 or a sequence having at least 60%, at least 70%, at least 80%, at least 90%, at least 95%, at least 96%, at least 97%, at least 98%, or at least 99% sequence identity thereto. In certain embodiments, the psiK is encoded by a nucleotide sequence comprising SEQ ID NO: 6 or a sequence having at least 60%, at least 70%, at least 80%, at least 90%, at least 95%, at least 96%, at least 97%, at least 98%, or at least 99% sequence identity thereto.

In certain embodiments, the prokaryotic cell is contacted with an expression vector comprising a psiD gene and a psiK gene all under control of a single promoter in operon configuration. In certain embodiments, the prokaryotic cell is contacted with an expression vector comprising a psiD gene and a psiK gene, wherein each gene is under control of a separate promoter in pseudooperon configuration. In certain embodiments, each gene is in monocistronic configuration, wherein each gene has a promoter and a terminator. Any configuration or arrangement of promoters and terminators is envisaged. In certain embodiments, none of the expression vectors comprises a psiM gene.

In some embodiments, the promoter is selected from the group consisting of G6 mutant T7, H9 mutant T7, H10 mutant T7, C4 mutant T7, consensus T7, Lac, Lac UV5, tac, trc, GAP, and xylA promoter.

In certain embodiments, the expression vector comprises the nucleic acid sequence of SEQ ID NO: 23 or a sequence having at least 60%, at least 70%, at least 80%, at least 90%, at least 95%, at least 96%, at least 97%, at least 98%, or at least 99% sequence identity thereto. In certain embodiments, the expression vector is pETM6-C4-psiDK or a vector having at least 60%, at least 70%, at least 80%, at least 90%, at least 95%, at least 96%, at least 97%, at least 98%, or at least 99% sequence identity thereto.

Kits

Provided is a transfection kit comprising an expression vector as described herein. Such a kit may comprise a carrying means being compartmentalized to receive in close confinement one or more container means such as, e.g., vials or test tubes. Each of such container means comprises components or a mixture of components needed to perform a transfection. Such kits may include, for example, one or more components selected from vectors, cells, reagents, lipid-aggregate forming compounds, transfection enhancers, or biologically active molecules

EXAMPLES

The following examples describe various compositions and methods for genetic modification of cells to aid in the production of psilocybin, according to the general inventive concepts.

Example 1

Materials and Methods

Bacterial Strains, Vectors, and Media

*E. coli* DH5α was used to propagate all plasmids, while BL21 Star™ (DE3) was used as the host for all chemical production experiments. Plasmid transformations were completed using standard electro and chemical competency protocols as specified. Unless noted otherwise, Andrew's Magic Media (AMM) was used for both overnight growth and production media, while Luria Broth (LB) was used for plasmid propagation during cloning. The antibiotics ampicillin (80 μg/mL), chloramphenicol (25 μg/mL), and streptomycin (50 μg/mL) were added at their respective concentrations to the culture media when using pETM6, pACM4, and pCDM4-derived vectors, respectively. The exogenous pathway genes encoding the enzymes PsiD, PsiK, and PsiM contained on plasmids pJF24, pJF23, and pFB13, respectively, were obtained from the Hoffmeister group of Friedrich-Schiller University, in Jena, Germany.

Plasmid construction: The original ePathBrick expression vectors, #4, #5, and #6 (Table 2) were modified through two rounds of site directed mutagenesis with primers 1 through 4 (Table 3) to result in the corresponding 'SDM2x' series of vectors: #7, #8, and #9 (Table 2). This mutagenesis was performed to swap the positions of the isocaudomer restriction enzyme pair XmaJI/XbaI in the vector. This change allows for the monocistronic and pseudooperon pathway configurations to be constructed more cost efficiently by avoiding the use of the costly XmaJI restriction enzyme. This series of vectors was then used to construct the vectors used in the defined copy number library study #10-#27 (Table 2).

Plasmids #1-#3 containing psiD, psiK, and psiM, respectively, were restriction enzyme digested with NdeI and HindIII, gel extracted, and ligated into the pETM6-SDM2x (#7, Table 2) plasmid backbone, resulting in plasmids #10, #11, and #12 (Table 2). All multigene expression plasmids were constructed in pseudooperon configuration using a modified version of the previously published ePathBrick methods as described above, while all transcriptional libraries were constructed using standard ePathOptimize methods.

Standard screening conditions: Standard screening was performed in 2 mL working volume cultures in 48-well plates at 37° C. AMM supplemented with serine (1 g/L), 4-hydroxyindole (350 mg/L), and appropriate antibiotics were used unless otherwise noted. Overnight cultures were grown from either an agar plate or freezer stock culture in AMM with appropriate antibiotics and supplements for 14-16 hours in a shaking 37° C. incubator. Induction with 1 mM isopropyl β-D-1-thiogalactopyranoside (IPTG) occurred four hours after inoculation, unless otherwise noted. Cultures were then sampled 24 hours post inoculation and subjected to HPLC analysis as described in analytical methods below.

Figure 2A:
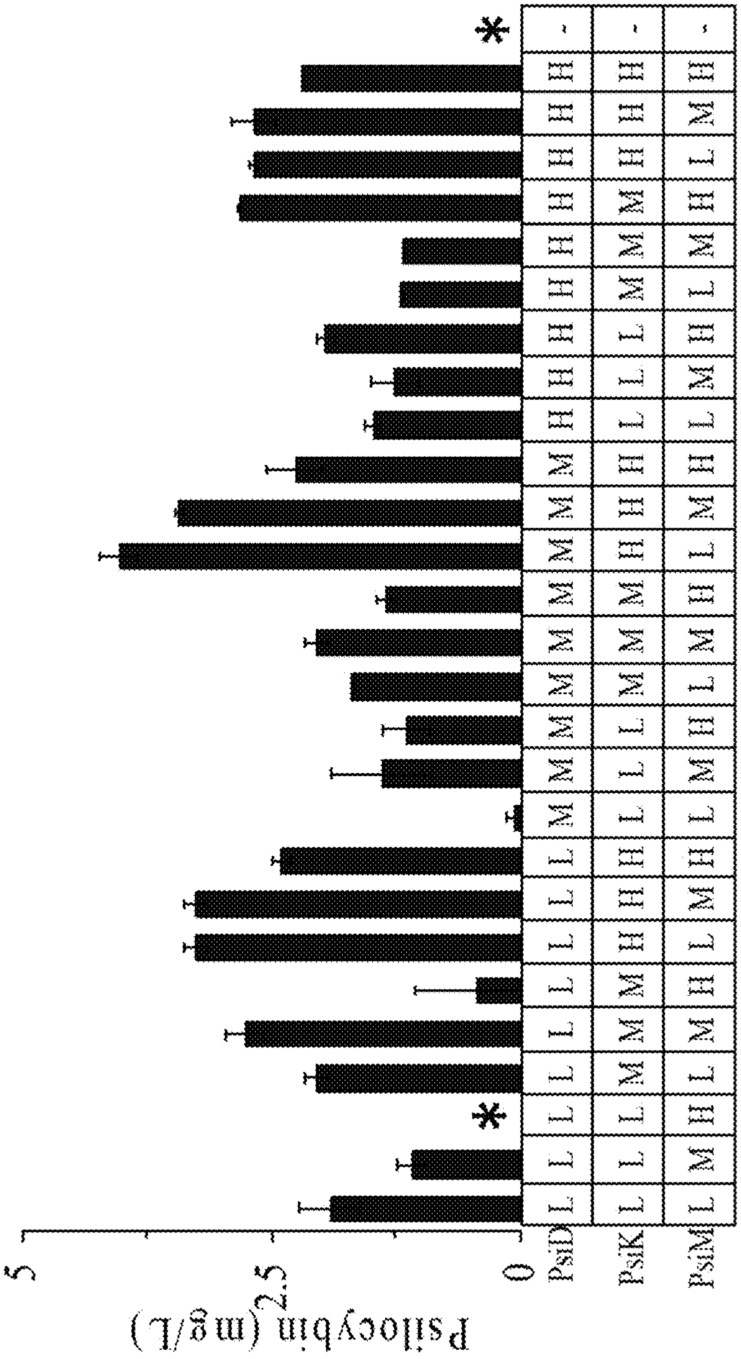
FIGS. 2A-2D show a summary of genetic strategies for increasing production.
Figure 2B:
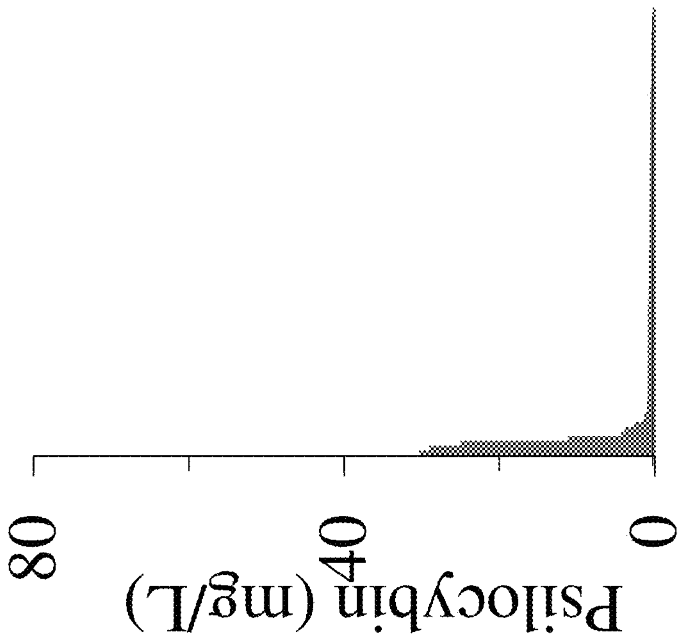

Library construction: The defined copy number library was constructed using plasmid #7 (High), #8 (Medium), and #9 (Low). The pathway genes were modulated in either the high, medium, and low copy number vectors, as shown in FIG. 2A. The BL21 Star™ (DE3) production host was transformed with the appropriate plasmids such that each strain had all three vectors, even if some were empty, to enable the same antibiotic resistance burden to be present in all defined library members (FIG. 1A). In the cases where multiple genes were present at a single expression level, the plasmids were constructed in pseudooperon configuration as described above.

Random promoter libraries were assembled using standard ePathOptimize methods with the five original mutant T7 promoters: G6, H9, H10, C4, and consensus. Random libraries were built in pseudooperon (FIG. 1B) and basic operon (FIG. 1C) forms, maintaining a sufficient number of colonies at each cloning step as to not limit library size.

Fermentation Optimization: Once a genetically superior production strain, pPsilo16 (#28, Table 2) was identified, fermentation conditions were optimized to further enhance psilocybin production. The effect of varying induction timing was first investigated under standard screening conditions, then further evaluated under other conditions that have been shown to affect cellular growth rate and subsequently optimal induction timing including: 1. base media identity (AMM, LB), 2. media carbon source (glucose, glycerol), 3. production temperature (30° C., 37° C., 40° C., 42° C.), 4. inducer concentration (1 mM, 0.5 mM, 0.1 mM), 5. concentration of media supplements: serine and methionine (0 g/L, 1 g/L, 5 g/L), and 6. concentration of 4-hydroxyindole substrate (150 mg/L, 350 mg/L, 500 mg/L). All screening was completed in 48-well plates under standard screening conditions unless otherwise noted.

Figure 17A:
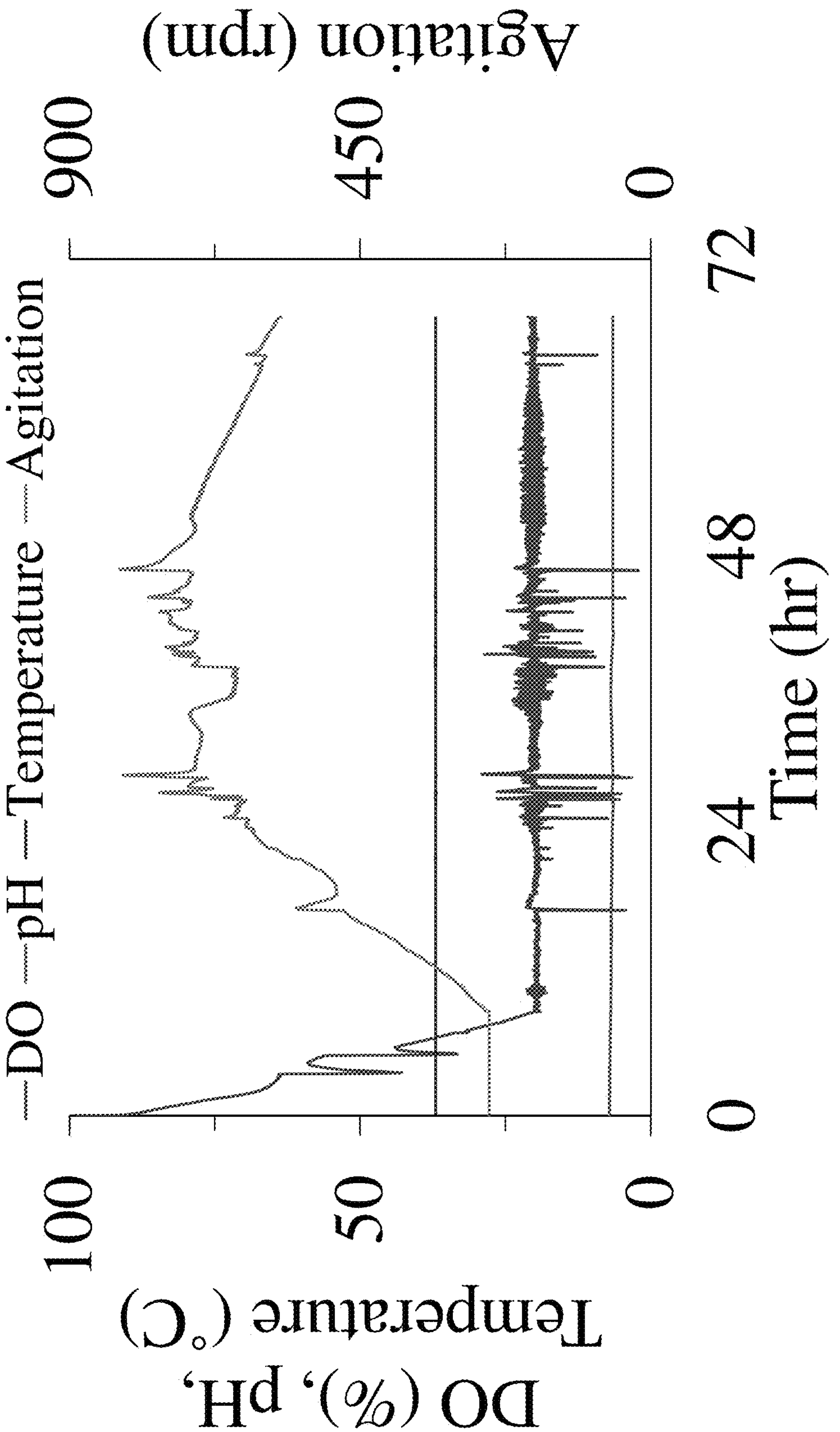
FIGS. 17A-17D show data for fed-batch bioreactor study.
Figure 17B:
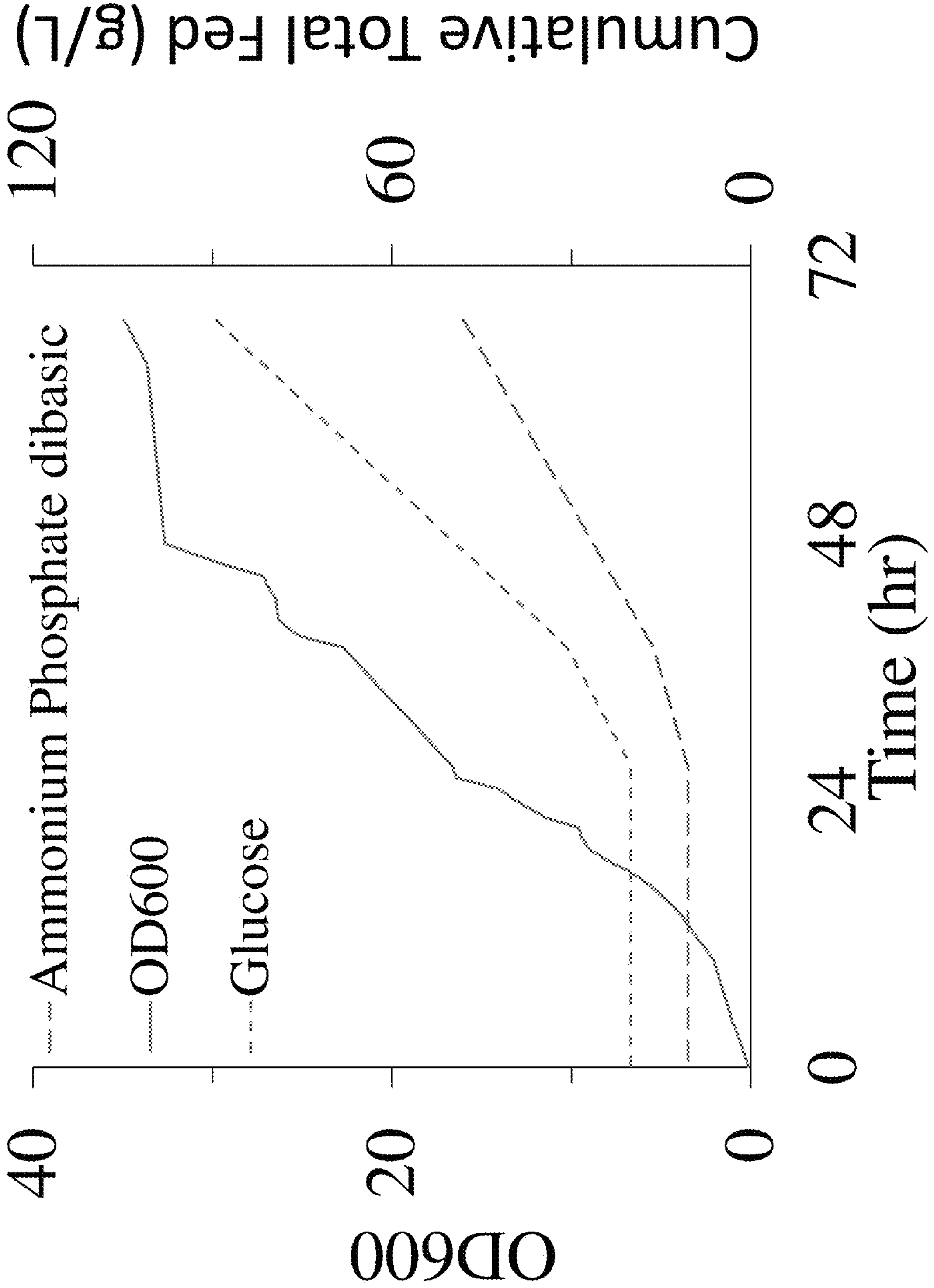
Figure 17C:
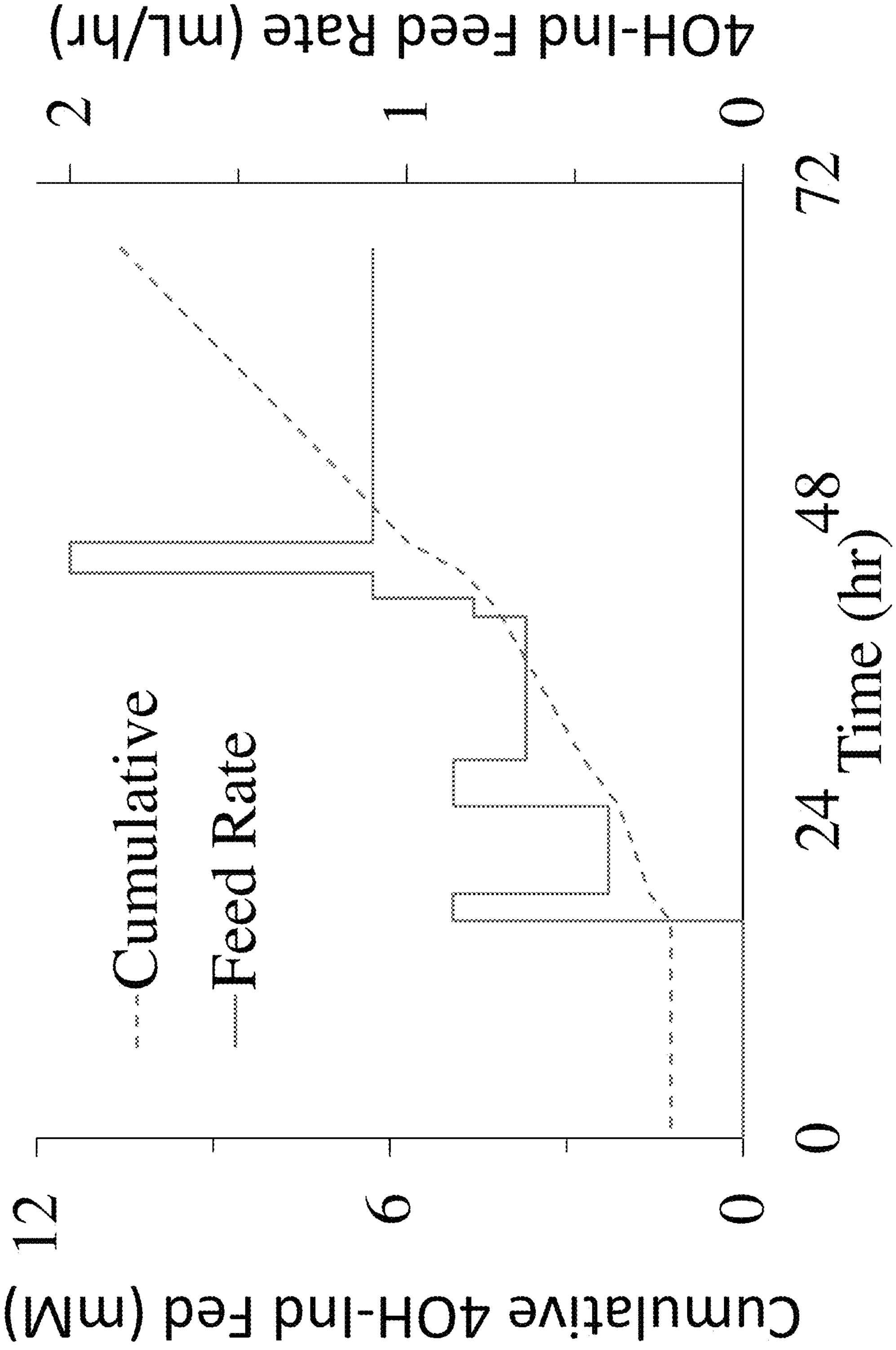

Scale-up study: In order to demonstrate the scalability of our selected production host and process, a scale-up study was performed in an Eppendorf BioFlo120 bioreactor with 1.5 L working volume. The cylindrical vessel was mixed by a direct drive shaft containing two Rushton-type impellers positioned equidistance under the liquid surface. The overnight culture of pPsilo16 was grown for 14 hours at 37° C. in AMM supplemented with serine (5 g/L), methionine (5 g/L), and appropriate antibiotics. The bioreactor was inoculated at 2% v/v to an initial $OD_{600}$ of approximately 0.09. The bioreactor was initially filled with AMM media (1.5 L) supplemented with 150 mg/L 4-hydroxyindole, 5 g/L serine, and 5 g/L methionine. Temperature was held constant at 37° C. with a heat jacket and recirculating cooling water, pH was automatically controlled at 6.5 with the addition of 10 M NaOH, and dissolved oxygen (DO) was maintained at 20% of saturation through agitation cascade control (250-1000 rpm). Full oxygen saturation was defined under the conditions of 37° C., pH 7.0, 250 rpm agitation, and 3 lpm of standard air. The zero-oxygen set point was achieved by a nitrogen gas flush. Samples were collected periodically for measurement of $OD_{600}$ and metabolite analysis. The bioreactor was induced with 1 mM IPTG 4 hours post inoculation. Once the initial 20 g/L of glucose was exhausted, as identified by a DO spike, separate feed streams of 500 g/L glucose and 90 g/L $(NH_4)_2HPO_4$ were fed at a flow rate ranging from 2.0 to 4.0 mL/L/hr (FIG. 17B). Beginning 12 hours post inoculation, a continuous supply of 4-hydroxyindole was supplied by external syringe pump to the bioreactor. The feed rate of 4-hydroxyindole was manually varied from 11 to 53 mg/L/hr according to the observed buildup of the key pathway intermediate 4-hydroxytryptophan (FIG. 17C). The concentration of psilocybin and all intermediate compounds were immediately analyzed via HPLC on an approximate 45-minute delay and were used as feedback into the feeding strategy described above.

Analytical Methods: Samples were prepared by adding an equal volume of 100% ethanol or 100% deionized water and fermentation broth, vortexed briefly, and then centrifuged at 12000×g for 10 minutes. 2 μL of the resulting supernatant was then injected for HPLC or LC-MS analysis. Analysis was performed on a Thermo Scientific Ultimate 3000 High-Performance Liquid Chromatography (HPLC) system equipped with Diode Array Detector (DAD) and Refractive Index Detector (RID). Authentic standards were purchased for glucose (Sigma), psilocybin (Cerilliant), and 4-hydroxyindole (BioSynth). Standards for baeocystin, norbaeocystin, 4-hydroxytryptamine, and 4-hydroxytryptophan were quantified using a standard for a similar analog due to limited commercial availability and extremely high cost, approx. $2000 USD for 1 mg of the authentic standard. Baeocystin and norbaeocystin were quantified on the psilocybin standard curve, while 4-hydroxytryptamine and 4-hydroxytryptophan were quantified on the standard curves of 5-hydroxytryptamine (Alfa Aesar, Haverhill Massachusetts) and 5-hydroxytryptophan (Alfa Aesar, Haverhill Massachusetts), respectively (FIG. 7). No significant intracellular accumulation of target metabolites was observed upon analysis with and without cell lysis. Transport across the cell membrane was assumed to be passive, however, specific investigation into this phenomenon was not undertaken for this work.

Glucose analysis was performed using an Aminex HPX-87H column maintained at 30° C. followed by a refractive index detector (RID) held at 35° C. The mobile phase was 5 mM $H_2SO_4$ in water at a flow rate of 0.6 mL/min. Glucose was quantified using a standard curve with a retention time of 8.8 min.

UV absorbance at 280 nm was used to quantify all aromatic compounds. Analysis was performed using an Agilent ZORBAX Eclipse XDB-C18 analytical column (3.0 mm×250 mm, 5 μm) with mobile phases of acetonitrile (A) and water (B) both containing 0.1% formic acid at a flow rate of 1 mL/min: 0 min, 5% A; 0.43 min, 5% A; 5.15 min, 19% A; 6.44 min, 100% A; 7.73 min 100% A; 7.73 min, 5% A; 9.87 min, 5% A. This method resulted in the following observed retention times: psilocybin (2.2 min), baeocystin (1.9 min), norbaeocystin (1.7 min), 4-hydroxytryptamine (3.4 min), 4-hydroxytryptophan (3.6 min), and 4-hydroxyindole (6.6 min). High Resolution Liquid Chromatography Mass Spectrometry (LC-MS) and Mass Spectrometry-Mass Spectrometry (LC-MS/MS) data were measured on a Thermo Scientific LTQ Orbitrap XL mass spectrometer equipped with an Ion Max ESI source using the same mobile phases and column described above. The flow rate was adjusted to 0.250 mL/min resulting in a method with the following gradient: 0 min, 5% A; 1 min, 5% A; 24 min, 19% A; 30 min, 100% A; 36 min 100% A; 36 min, 5% A; 46 min, 5% A. This method resulted in the following observed retention times: psilocybin (8.7 min), baeocystin (7.6 min), norbaeocystin (6.4 min), 4-hydroxytryptamine (13.3 min), 4-hydroxytryptophan (14.2 min), and 4-hydroxyindole (27 min). The Orbitrap was operated in positive mode using direct infusion from a syringe at 5 μl/min for optimization of tuning parameters and for external calibration. A 5-hydroxytryptamine sample was prepared at ~0.1 mg/ml (570 uM) in 50% ethanol/50% water for tuning. External calibration was performed using the Pierce LTQ ESI Positive Ion Calibration Solution, allowing for a less than 5 ppm mass accuracy.

Mass spectrometry parameters in positive mode were spray voltage 3.5 kV, capillary temperature 275° C., capillary voltage 23 V and tube lens voltage 80 V (optimized by tuning on 5-hydroxytryptamine), nitrogen sheath, auxiliary, and sweep gas were 15, 30, 1 a.u., full scan mode (m/z 100-500) at a resolution of 60,000 and an AGC target of 1e6.

LC-MS/MS data was collected in the data-dependent acquisition mode, where the full MS scan was followed by fragmentation of the three most abundant peaks by higher energy collisional dissociation (HCD). Data was collected in the Orbitrap with a minimum m/z of 50 at 30,000 resolution, AGC target of 1e5, and intensity threshold of 200K using normalized collision energy of 40, default charge state of 1, activation time of 30 ms, and maximum injection times of 200 msec for both MS and MS/MS scans. All data were processed using Xcalibur/Qual Browser 2.1.0 SP1 build (Thermo Scientific). MS/MS fragmentation data can be found in FIG. 9.

Results

Psilocybin production genes (psiD, psiK, and psiM) from *P. cubensis* were heterologously expressed in *E. coli* using the strong T7 promoter system. Induction with IPTG allowed for the production of 2.19±0.02 mg/L psilocybin. To confirm compound identities, culture media from the psilocybin production host was subjected to liquid chromatography-mass spectroscopy analysis on a Thermo Orbitrap XL LC-MS system. Psilocybin, as well as all precursor and intermediate compounds in the biosynthetic pathway, were identified with better than 5 ppm mass accuracy. The sample was then subjected to additional MS/MS fragmentation analysis to further support structural identification of all indole derived intermediates and final products. In each case, fragmentation products for the deamination, dephosphorylation (if applicable), and loss of both functional groups were observed, confirming the identification of psilocybin, and its intermediates: 4-hydroxytryptophan, 4-hydroxytryptamine, norbaeocystin, and baeocystin, with better than 5 ppm mass accuracy. Additionally, expected retention times and order of elution were consistent with previously published efforts. The overexpression of the native tryptophan synthase (TrpAB) was also performed in an attempt to push flux through the heterologous production pathway. The native expression level was determined to be sufficient to maintain the necessary pathway flux, as supported by the buildup of 4-hydroxytryptophan in nearly all fermentation studies performed.

Defined Copy Number Library: A defined 27-member copy number library consisting of the 3 heterologous biosynthesis genes (psiD, psiK, and psiM) each expressed on 3 different copy number plasmids was constructed and screened in 48-well plates as shown in FIG. 2A. Each member of the library contained each of the three genes spread across a low (pACM4-SDM2X), medium (pCDM4-SDM2x), or high (pETM6-SDM2x) copy number plasmid (FIG. 1A). This library screen realized minor improvements over the original All-High construct (2.19±0.02 mg/L), where final titers of 4.0±0.2 mg/L were achieved with the combination of psiK expressed from the pETM6-SDM2x vector, psiD expressed from the pCDM4-SDM2x vector, and psiM expressed from the pACM4-SDM2X vector in the BL21 Star™ (DE3) expression host.

FIGS. 2A-2D show a summary of genetic strategies for increasing production.

Pseudooperaon Library: The pseudooperon library were constructed having a different mutant promoter in front of each of the three enzyme encoding sequences, psiD, psiK, and psiM, while having a single terminator at the end of the 3-gene synthetic operon (FIG. 1B). This configuration resulted in a widely variable transcriptional landscape in which each promoter resulted in a distinct mRNA capable of encoding translation of either 1, 2, or 3 of the pathway enzymes. In this configuration, a possible library size of 125 pathway configurations existed, and 231 random colonies were screened. The large majority of variants demonstrated low (30%) or no production (65%); however, a small population of mutants demonstrated significant improvements in production (FIG. 2B) over the previous defined library screen (FIG. 2A). Additional analysis of the HPLC data revealed a significant accumulation of the intermediate, 4-hydroxytryptophan, suggesting that poor functional activity from the PsiD enzyme led to the underperformance of the majority of the members in the pseudooperon library.

Figure 2C:
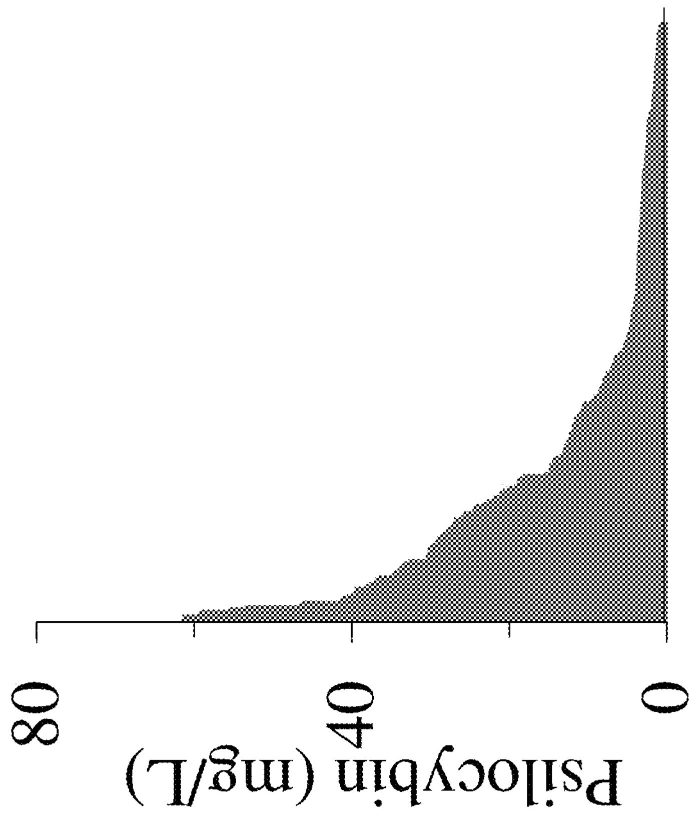
Figure 2D:
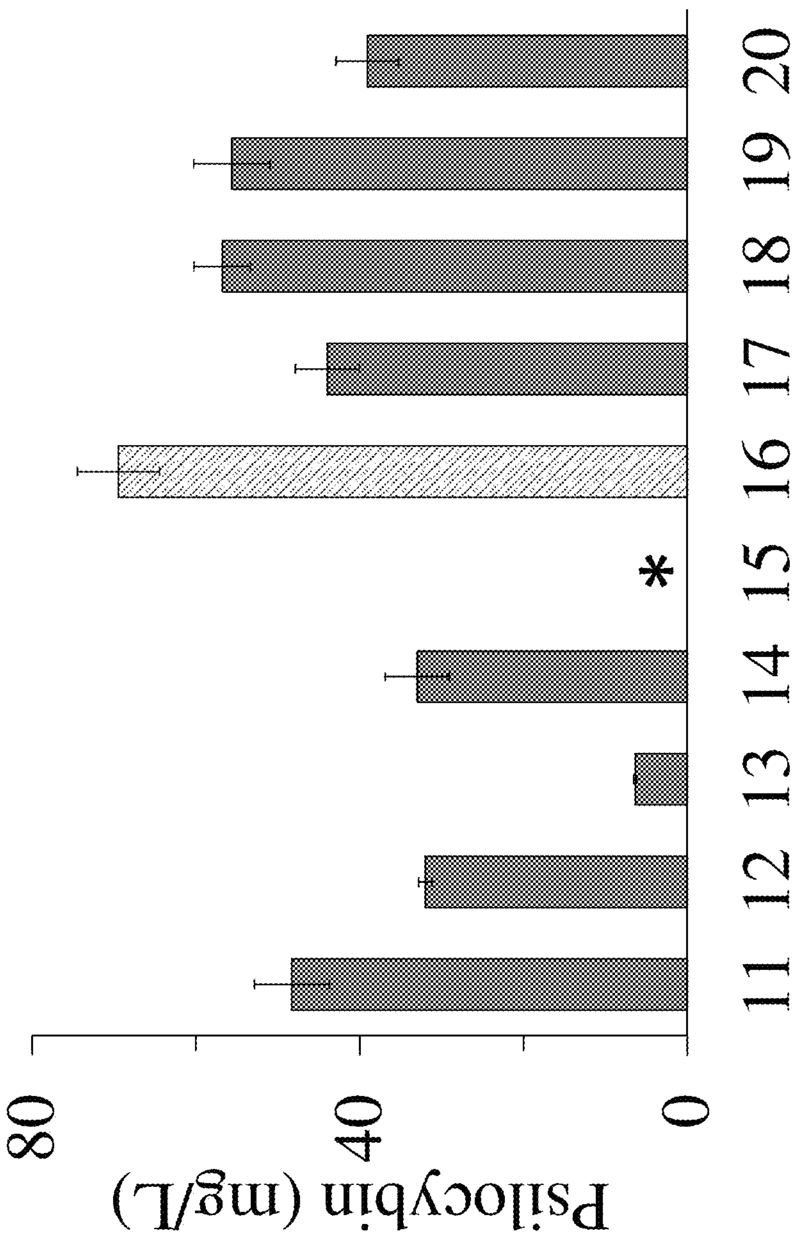

Basic Operon Library: In the operon configuration, the three-gene pathway was expressed from a single high-copy plasmid under the control of a single promoter and terminator where each gene has an identical ribosome binding site (RBS) (FIG. 1C). The promoter sequence was randomized to one of five mutant T7 promoters (G6, H9, H10, C4, Consensus) using the ePathOptimize approach, resulting in a library that contained 5 potential promoter combinations (FIG. 2C). After screening nearly 50X the library size, the top 10 variants were selected for further screening. These top variants were re-cloned into an empty plasmid backbone and transformed to eliminate the possibility of spurious plasmid or strain mutations (FIG. 2D). Mutant #16 (pPsilo16) was selected for further investigation due to its top production and high reproducibility across multiple fermentations. The sequencing results revealed that pPsilo16 contained the H10 mutant promoter which has been previously characterized as a medium strength promoter, with between 40% and 70% of the effective expression strength of the consensus T7 sequence. The top mutants from the basic operon screen showed a 17-fold improvement in titer over the best performing mutants from the defined copy number library study.

Figure 3A:
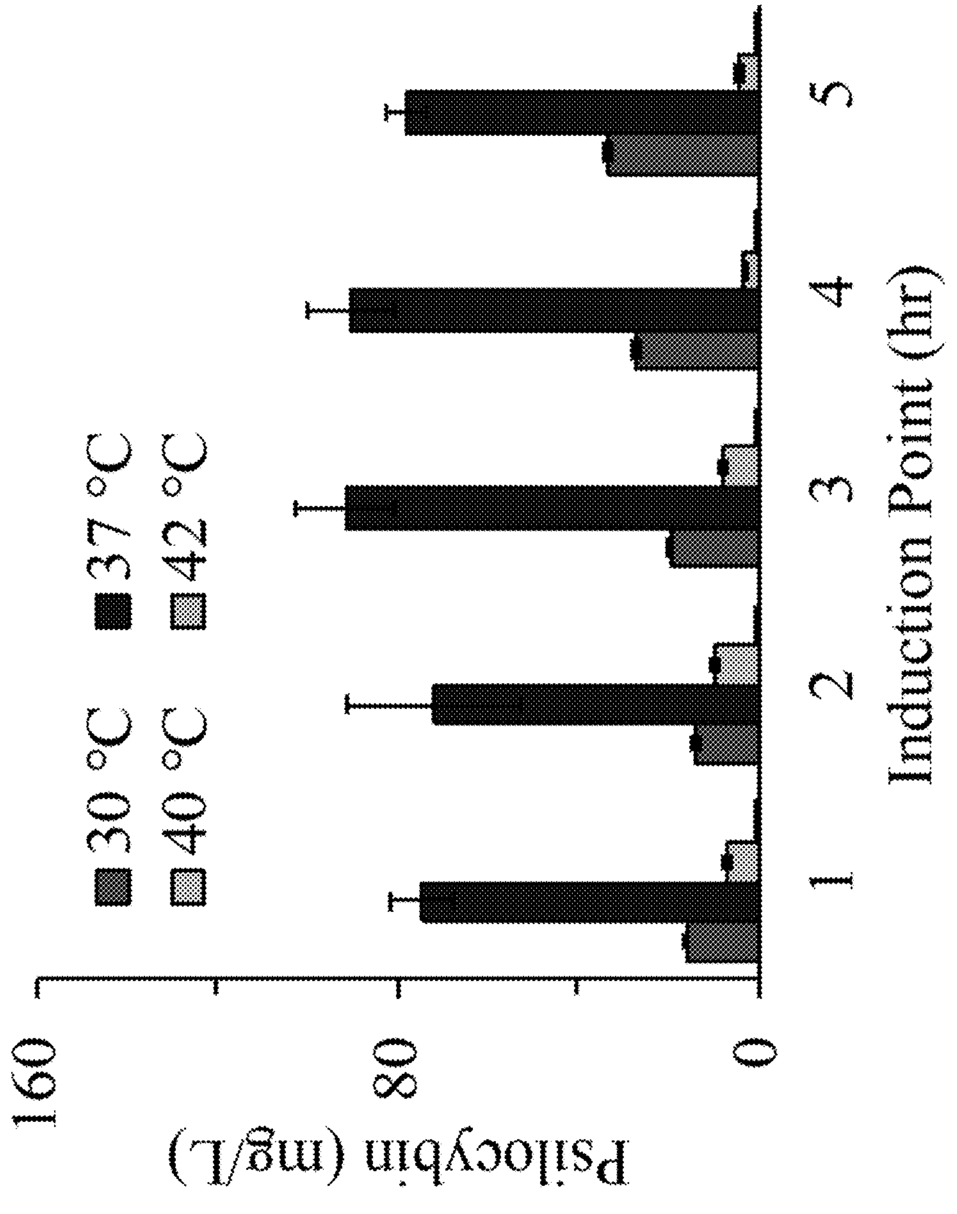
FIGS. 3A-3C show a summary of fermentation conditions optimization studies.

Fermentation Conditions: After identifying pPsilo16 as the best strain with respect to the highest psilocybin production, low buildup of intermediate products, and consistent reproducibility, the strain underwent a series of experiments to determine the best fermentation conditions for the production of psilocybin. All genetic optimization experiments were conducted under standard conditions (as described in the Materials and Methods) determined from initial screening. Many studies in the metabolic engineering literature have demonstrated high sensitivity to variations in induction point for pathways controlled by the T7-lac inducible promoter. Additionally, induction timing can have a large impact on overall cell growth and can lead to difficulties achieving reproducible production upon scale-up. Upon evaluation of induction sensitivity for pPsilo16, it was found that the cells demonstrate low sensitivity to induction point, with the maximum production achieved with induction 3 to 4 hours post inoculation (FIG. 3A). No psilocybin production was observed in the non-induced controls.

Figure 3B:
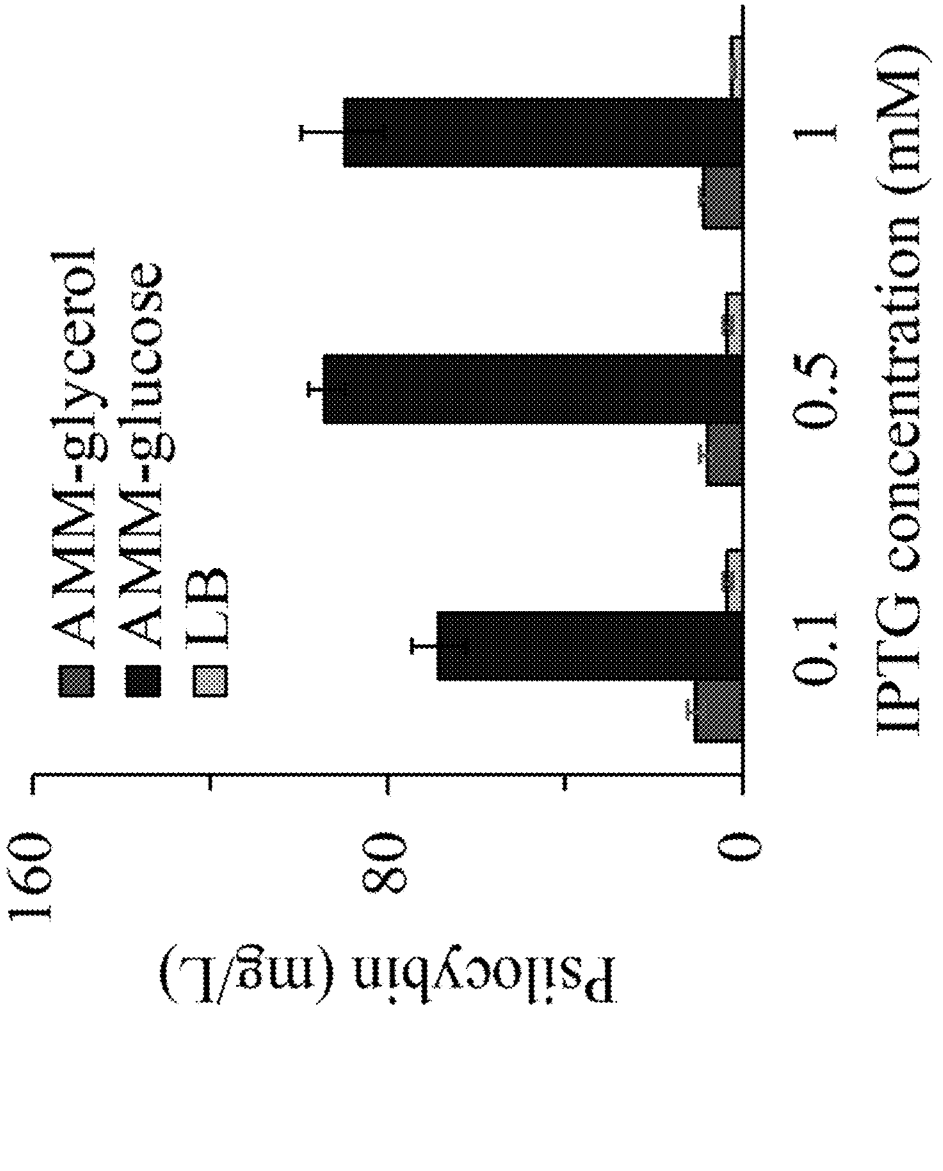
Figure 3C:
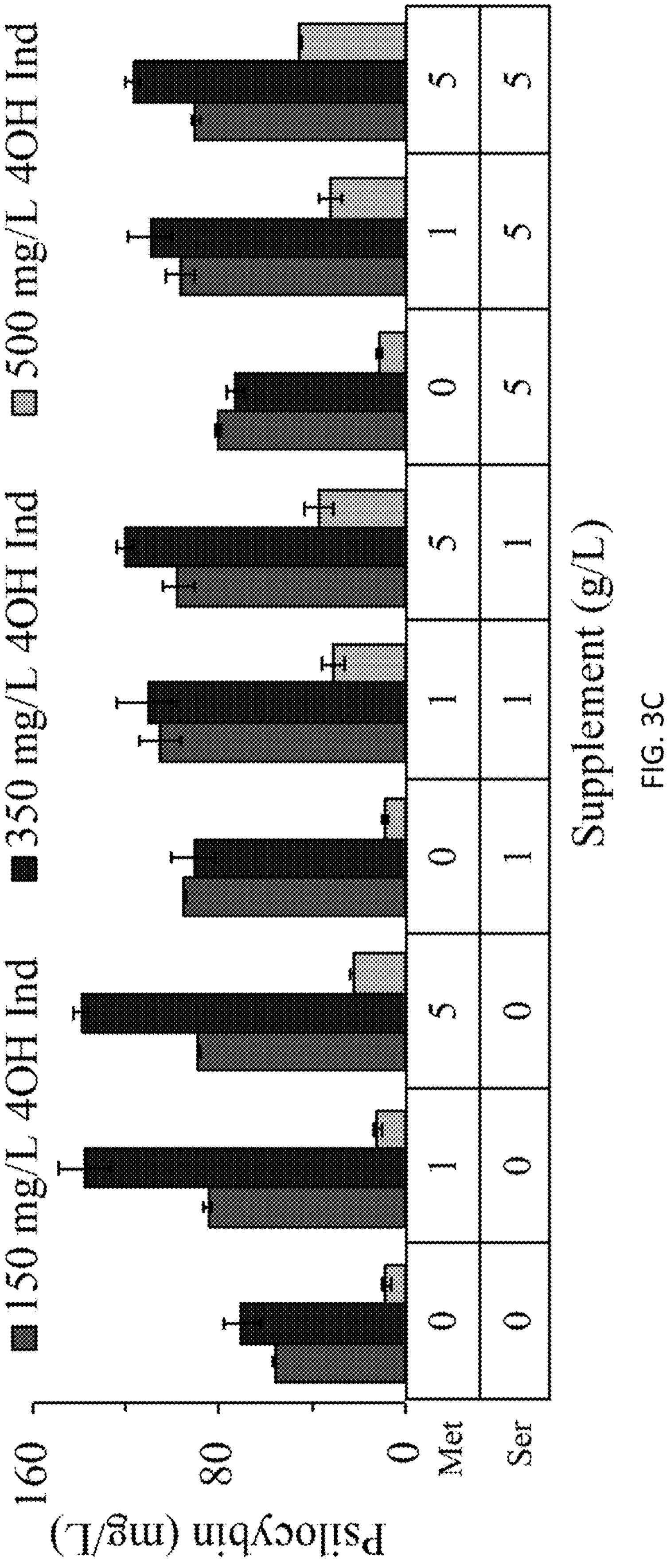

FIGS. 3A-3C show a summary of fermentation conditions screening studies.

Next, base media, carbon source identity, and inducer concentration was evaluated. Since these variables can affect cellular growth rate and corresponding optimal induction points, each of these variables was evaluated across a range of induction points from 1 to 6 hours. As demonstrated in FIG. 3B, psilocybin production was very sensitive to both media and carbon source selection ($p<0.05$). When production was attempted in a rich undefined media such as LB, a dark colored insoluble product was observed along with low psilocybin production. Similarly, low production was also observed when grown on glycerol, however no colored products were observed. pPsilo16 demonstrated moderate sensitivity to IPTG concentration, with higher final concentrations of 0.5 and 1.0 mM over a range of induction time conditions ($p<0.05$) (FIG. 3B). This trend is likely influenced by the initial library screening, which was performed at 1.0 mM IPTG.

Production temperatures of 30° C., 37° C., 40° C., and 42° C. were also evaluated for their effect on psilocybin production (FIG. 3A). In an attempt to minimize the effect on changing induction points, all fermentations were started at 37° C. through the growth phase of the fermentation before being shifted to the production temperature 1 hour prior to induction. A significant preference ($p<0.05$) was seen for maintaining an isothermal fermentation temperature of 37° C. throughout both growth and production phases (FIG. 3A).

The fermentation screening was completed by evaluating the effects of the targeted media supplements: 4-hydroxyindole, serine, and methionine (FIG. 3C). Each media supplement was provided at high, medium, and low levels: 4-hydroxyindole (150, 350, and 500 mg/L), serine and methionine (0, 1, and 5 g/L). At high concentrations of 4-hydroxyindole, the cells demonstrated noticeable growth decline due to presumed cellular toxicity leading to reduced productivity. Serine addition showed minimal effects on psilocybin production, however, the addition of methionine in the presence of greater than 350 mg/L of 4-hydroxyindole resulted in a significant enhancement of psilocybin titer ($p<0.05$). Under the identified optimal screening conditions, psilocybin was produced at 139±2.7 mg/L, which represents a 63-fold improvement through the synergistic efforts of genetic and fermentation optimization.

Figure 4A:
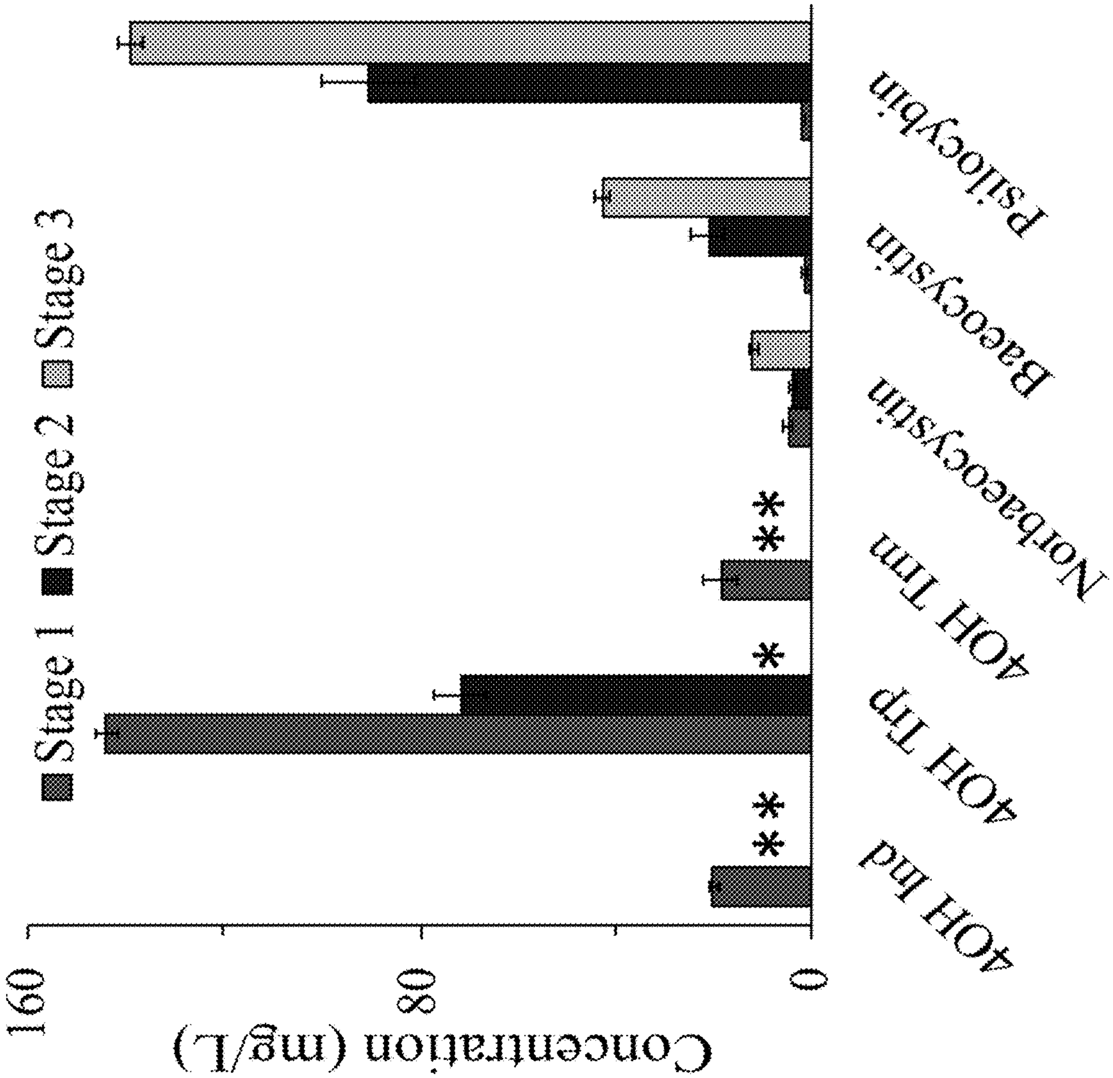
FIGS. 4A-4B show the screening evaluation and bioreactor scale up.
Figure 4B:
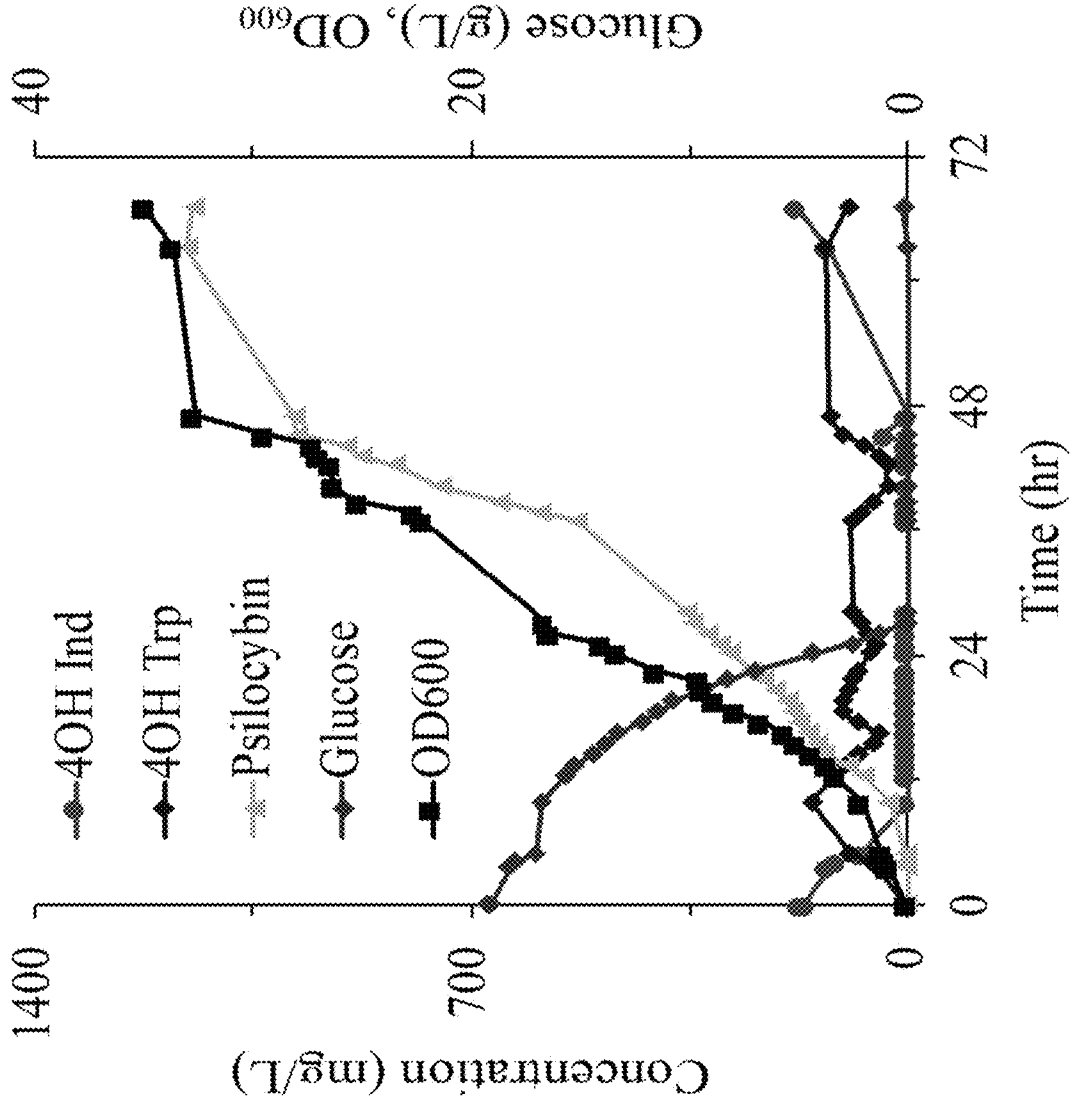

Scale-up: After identification of preferred production conditions for pPsilo16 strain, a fed-batch scale up study was completed as described in the Materials and Methods. This study resulted in the production of 1.16 g/L of psilocybin which represents an 8.3-fold improvement over the top conditions screening case in 48-well plates and a 528-fold improvement over the original construct. Precursor and intermediate product titers remained low throughout the fermentation enabling the culture to achieve a final $OD_{600}$ of 35 (FIG. 4B). Pathway intermediate concentrations were maintained at a low level through the use of a HPLC informed feeding strategy which enabled the substrate feed rate to be tailored to specific pathway bottleneck flux within 45 min of sampling. This led to an oscillatory concentration profile for the key pathway intermediate 4-hydroxytryptophan (FIG. 4B). The initial 20 g/L of glucose was completely consumed from the media after 25 hours and was then externally fed such that the culture maintained robust growth with low residual sugar content in the media to maximize product yield on glucose.

The production of psilocybin and all pathway intermediates were confirmed through the use of high mass accuracy LC-MS (FIG. 9). HPLC analysis of fermentation broth from strains containing incomplete pathways (i.e. psiDM and psiDK) was consistent with the conclusions of previous studies aimed at identifying the order of specific biosynthetic steps in the synthesis pathway.

Multiple genetic screening methods were utilized in parallel to identify a genetically superior mutant. Starting with the copy-number based approach, a 27-member library of 3 pathway genes, each at 3 discrete copy numbers (FIG. 2A) was constructed. Of the three genetic optimization screens presented, this method was the most tedious to construct, requiring each plasmid to be independently cloned and verified prior to screening. This defined library approach also yielded the lowest product titers with the best mutants demonstrating small but statistically significant ($p<0.05$) improvements over the All-High initial construct. Without wishing to be bound by theory, the limited titer improvement from this approach may be due to the increased metabolic burden associated with selection for and propagation of three independent plasmids.

Subsequent screening of two independent single-plasmid transcriptionally-varied promoter libraries with pathway genes in basic operon (FIG. 2C) and pseudooperon (FIG. 2B) configuration yielded considerably improved results over the initial copy number library. In each case, the library was screened using a medium-throughput HPLC-based screen. Each of these transcriptionally varied libraries were constructed using the high copy pETM6 plasmid vector. This enabled a wide range of expression levels to be screened, resulting in greater coverage of the psilocybin transcriptional landscape. The pseudooperon library screen demonstrated that a large majority of mutants (~95%) showed low or no psilocybin production. The reason for this widespread underperformance is unknown; however, it does motivate the use of random libraries coupled with variant screening for the identification of genetically superior mutants as the current predictive power of a priori pathway design is still lacking for most applications. Surprisingly, the simplistic basic-operon pathway design yielded the highest titer psilocybin production in this study. This coupled with the smallest library size of only 5 mutants, enabled rapid screening of several times the theoretical library size, resulting in high confidence of complete coverage of the full transcriptional landscape. Upon recloning and rescreening the top mutants from the operon library screen, several false positives were identified as shown in FIG. 2D. The source of error for these false positive mutants was not investigated as the false positive rate was at an acceptable level for the study design.

Additional increases in titer and yield were achieved through careful optimization of fermentation conditions (FIGS. 3A-3C). The genetically superior strain, pPsilo16, demonstrated low sensitivity to induction timing as compared to that of other amino acid derived high-value products; however, this could also be due to the supplementation of both 4-hydroxyindole and serine to the fermentation media, reducing the requirement for high flux through amino acid metabolism. Therefore, all additional fermentation optimization experiments were performed under a range of induction times. Little variation from the induction optimum of 4 hours post inoculation was observed, strengthening the observation of reduced sensitivity to induction timing.

The psilocybin production host demonstrated high sensitivity to media composition, carbon source identity, fermentation temperature, and inducer concentration (FIGS. 3A-3B). In each case, this preferred level was similar to that of the standard screening conditions. This is likely not a coincidence, as some basic initial screening was performed to identify conditions under which our proof-of-principle strain best performed. Furthermore, the initial genetic screening studies were performed under standard screening conditions, which also self-selects for mutants with top performance under the test conditions.

The largest gains in the fermentation optimization aspect of this study were achieved through the media supplementation studies (FIG. 3C). In this study, the concentrations of 4-hydroxyindole, serine, and methionine were varied. These supplements were selected specifically for their direct effect on the psilocybin production pathway (FIG. 1D). 4-hydroxyindole and serine are condensed by TrpAB in the first dedicated step of the pathway to form the intermediate 4-hydroxytryptophan. Although *E. coli* can produce serine and indole naturally, it lacks the ability to express the P450 hydroxylase that oxidizes indole into 4-hydroxyindole. Additionally, with the high fluxes through our engineered pathway, it was hypothesized that the cellular supply of serine would be quickly depleted, requiring additional supplementation to not limit pathway flux. Finally, methionine was supplemented to enhance intercellular pools of the activated methyl donor, SAM. The final two biosynthetic steps are both catalyzed by the SAM-dependent methyltransferase, PsiM. Previous studies with SAM-dependent methylations in *E. coli* have documented SAM-limited flux to final products.

Analysis of intermediate product concentrations was performed to evaluate the success of each study. A comparison is presented (FIG. 4A) between the initial proof-of-principle 'All-High' strain (Stage 1) and the top production strain, both post genetic optimization (Stage 2) and post genetic and fermentation optimization (Stage 3). Each additional optimization stage resulted in further enhanced psilocybin titers, accomplished through a reduction in intermediate product concentrations, and generally enhanced flux towards the final product.

The information gained from the genetic and fermentation optimization studies was applied in a scale-up study for the production of psilocybin in a fed-batch bioreactor. In this study, many of the optimization parameters such as temperature, inducer concentration, and induction timing were applied as previously optimized. Information from the supplement addition studies was used but applied with modification from the 2 mL batch studies. In the fed-batch studies, both serine and methionine were supplemented at the high level of 5 g/L to account for higher cellular demand due to enhanced cell growth. Furthermore, in the small-scale studies a growth deficit was observed at higher concentrations of 4-hydroxyindole and 4-hydroxytryptophan. To counter this, a low amount of 4-hydroxyindole (150 mg/L) was added initially to the media, while a low-flow syringe pump, containing a 40 mg/mL 4-hydroxyindole solution, was connected for slow external supplementation. To determine the optimal feed rate, the pathway flux through the bottleneck point, PsiD, was estimated through frequent HPLC analysis of the fermentation broth. As 4-hydroxytryptophan titers fell, the flux of 4-hydroxyindole was increased to meet the high flux demand, and vise-versa. This strategy resulted in an oscillatory concentration profile for 4-hydroxytryptophan and maintained all intermediates at low levels, enabling robust and extended growth and psilocybin production (FIG. 4B).

In small batch fermentation studies, the work presented above resulted in a similar titer of psilocybin to that presented previously in the *A. nidulans* host. This indicates that both bacterial and fungal hosts show potential as production platforms for this important chemical. However, upon scale-up to a fed batch reactor our bacterial host demonstrated greatly enhanced psilocybin production resulting in a 10-fold enhancement over previously published results.

Figure 17D:
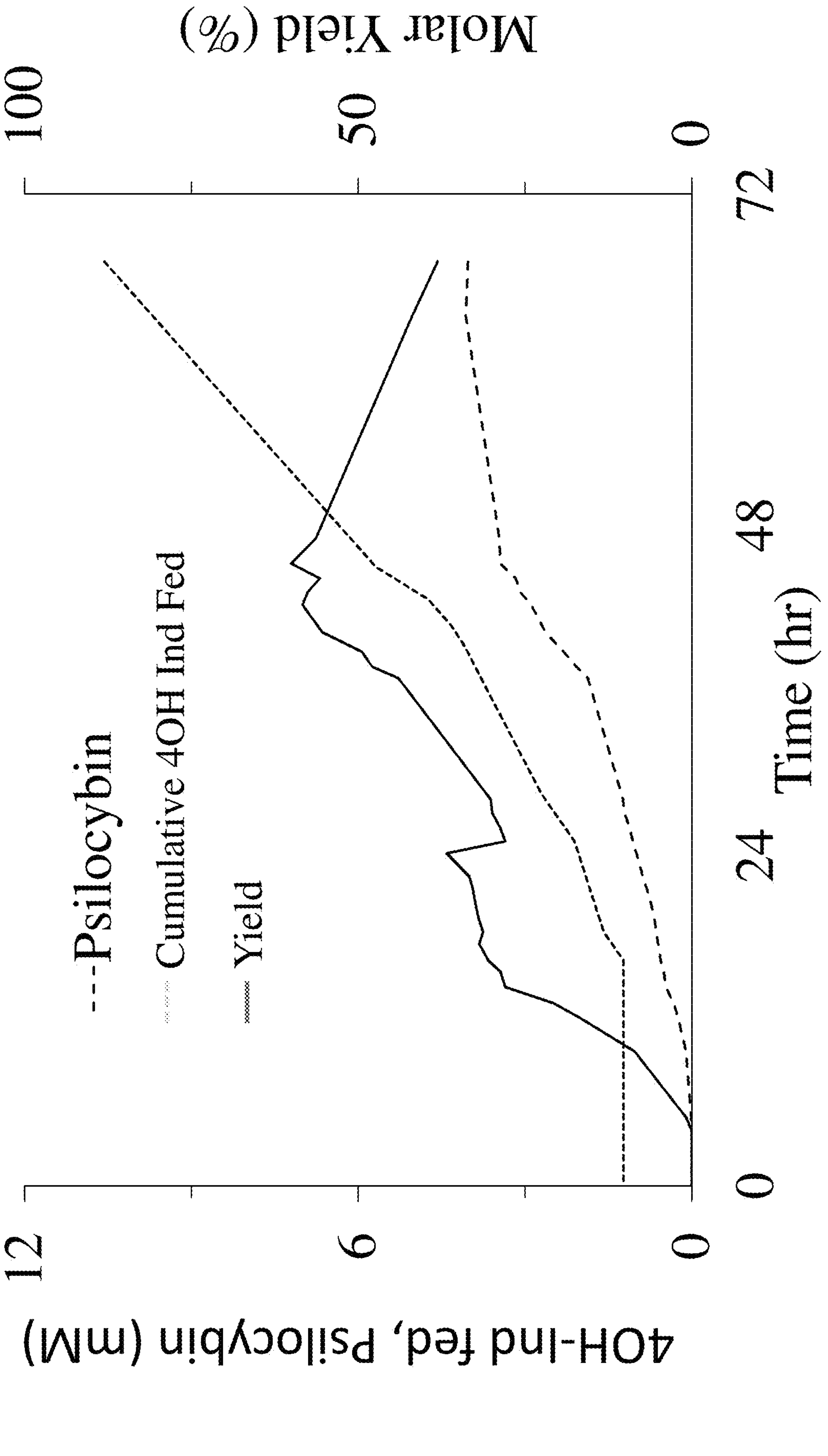

Provided is the first example of effective psilocybin production in a prokaryotic organism and the highest psilocybin titer to date from a recombinant host from any kingdom. This was accomplished through the combination of increased genetic and fermentation production in small scale, coupled with a scaled-up fed-batch study utilizing a unique HPLC informed substrate feeding strategy. The fed-batch study resulted in a psilocybin titer of 1.16 g/L with maximum and final molar yields from the 4-hydroxyindole substrate of 0.60 and 0.38 mol/mol, respectively (FIG. 17D).

Example 2: Production of Norbaeocystin

Materials and Methods

A transcriptional library comprised of five IPTG-inducible T7 promoter mutants of varied strength (G6, H9, H10, C4, and consensus) were used to construct two independently pooled libraries capable of norbaeocystin production: pETM6-xx5-psiDK (operon form, 5 member) and pETM6-xx5-psiD-xx5-psiDK (pseudooperon form, 25 members). These libraries were constructed using standard molecular cloning and ePathOptimize techniques analogous to those used for the construction of the psilocybin production plasmid libraries discussed above. The plasmid DNA libraries were then transformed into the production host strain BL21 Star™ (DE3) and screened in a medium throughput fermentation assay in 48-well plates. Andrew's Magic Media (AMM) supplemented with 20 g/L glucose, 350 mg/L of 4-hydroxyindole, and 1 g/L of serine was used as the microbial growth media and the fermentation screening and HPLC sample preparation was performed as described elsewhere herein. Andrew's Magic Media (AMM) is rich semi-defined media containing: 3.5 g/L $KH_2PO_4$, 5.0 g/L $K_2HPO_4$, 3.5 g/L $(NH4)_2HPO_4$, 2 g/L casamino acids, 100 mL of 10× MOPS Mix, 1 mL of 1M MgSO4, 0.1 mL of 1M CaCl2, 1 mL of 0.5 g/L thiamine HCL, supplemented with 20 g/L glucose). 10× MOPS Mix consisted of 83.72 g/L MOPS, 7.17 g/L Tricine, 28 mg/L $FeSO_4.7H_2O$, 29.2 g/L NaCl, 5.1 g/L $NH_4Cl$, 1.1 g/L $MgCl_2$, 0.48 g/L $K_2SO_4$, 0.2 mL Micronutrient Stock. Micronutrient Stock consisted of 0.18 g/L $(NH_4)_6Mo_7O_{24}$, 1.24 g/L $H_3BO_3$, 0.12 g/L $CuSO_4$, 0.8 g/L $MnCl_2$, 0.14 g/L $ZnSO_4$.

All norbaeocystin titers were quantified using a psilocybin standard curve due to the lack of a commercially available analytical standard.

Upon identification of top mutants from both the operon and pseudooperon libraries, the plasmids were purified, retransformed in the plasmid storage strain, DH5 a. A single DH5α colony was grown overnight, plasmid was purified, retransformed into BL21 Star™ (DE3) for additional screening, and sequenced to identify the mutant promoters controlling transcription of the exogenous pathway genes, psiD and psiK. The retransformed production strains were subjected to additional screening identical to that of the initial screen and with an additional 350 mg/L of 4-hydroxyindole added approximately 24 hours after inoculation. Final samples for HPLC analysis were taken 48 hours post inoculation.

Results

Figure 5:
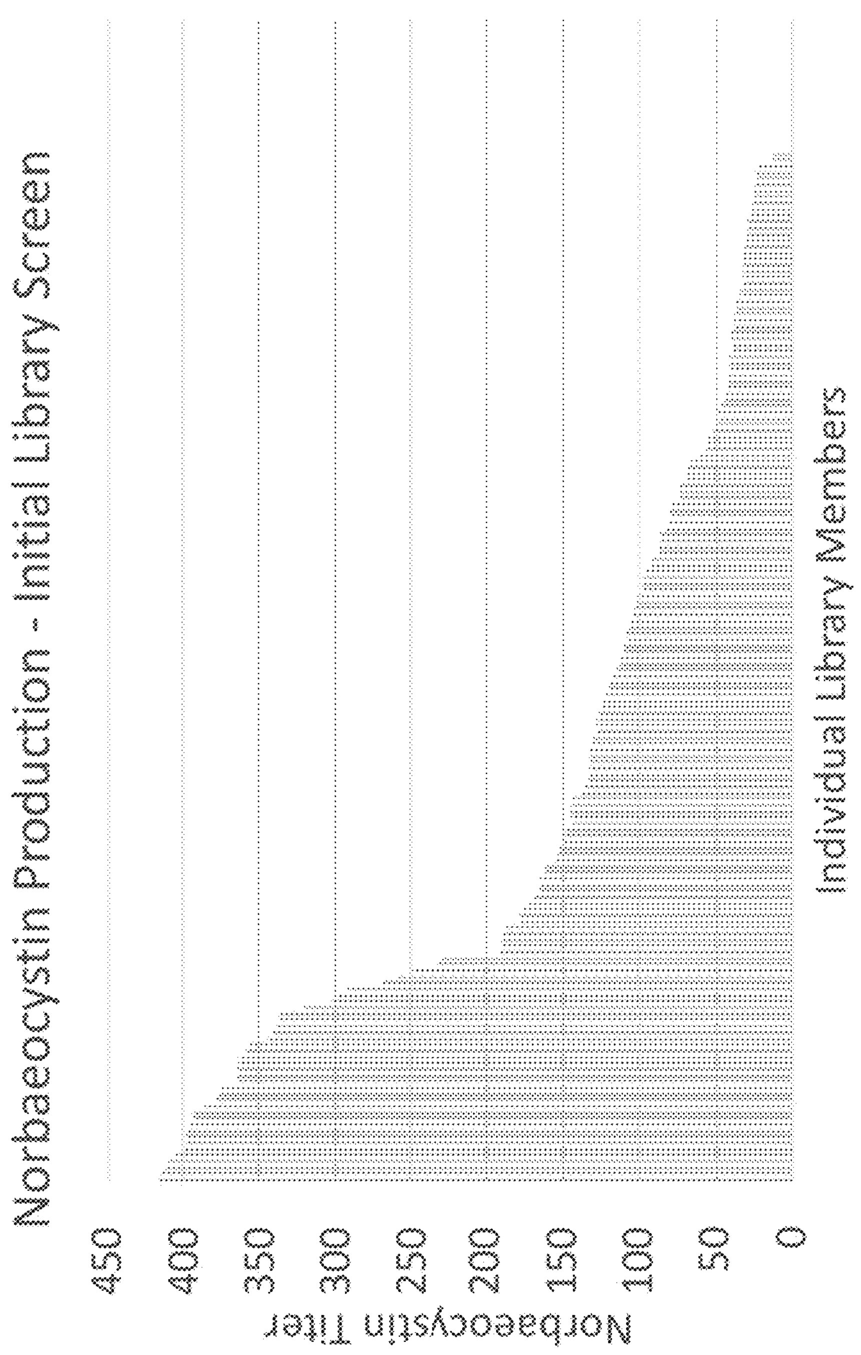
FIG. 5 is a graph showing norbaeocystin production from initial library screen in 48-well plates.

The initial screening resulted in a range of production levels in both the operon and pseudooperon libraries. 47 random mutants from the operon and 143 random mutants from pseudooperon library were screened. This represents 9.4× and 5.7× their respective library sizes. The top mutants from both libraries demonstrated complete consumption of the 4-hydroxyindole, no endpoint buildup of the 4-hydroxytryptophan, and produced approximately 400 mg/L of norbaeocystin (FIG. 5). This is a significant observation as the production of norbaeocystin in the top mutants is roughly 400% higher than the production of psilocybin from the optimized pPsilo16 mutant under similar conditions. Without wishing to be bound by theory, this indicates that regeneration of the methyl donor, SAM, is likely limiting in the psilocybin production case and supports the need for further studies targeted at alleviating this bottleneck.

Seven mutants from this initial screen at a variety of production levels were selected for additional testing and sequencing (Table 1). The sequencing results revealed an interesting trend of the top producing strains having the exogenous pathway controlled by the strong mutant promoter, C4, in both top producing mutants deriving from the operon and pseudooperon libraries. The data also supports a trend of reduced strength promoters leading to reduced norbaeocystin production. This is in contrast with the similarly performed psilocybin production work which resulted in the best performance from the medium strength, H10, mutant promoter.

Additionally, production of another tryptophan derived compound, violacein, found weakened promoters to produce significantly more product than strong promoters. Taken together, this data supports the discovery of a non-obvious and interesting solution for the biological production of norbaeocystin.

TABLE 1

| Strain # | Original Library | Plasmid Name | Norbaeocystin Titer | Promoter(s) Strength |
|---|---|---|---|---|
| O-H1 | Operon | pETM6-C4-psiDK | 415 mg/L | High |
| P3-D4 | Pseudooperon | pETM6-C4-psiD-C4-psiK | 398 mg/L | High |
| O-B1 | Operon | pETM6-H9-psiDK | 192 mg/L | Medium/Low |
| P2-E1 | Pseudooperon | pETM6-T7-psiD-H10-psiK | 152 mg/L | Medium/High |
| O-F1 | Operon | pETM6-G6-psiDK | 32 mg/L | Low |

Figure 6:
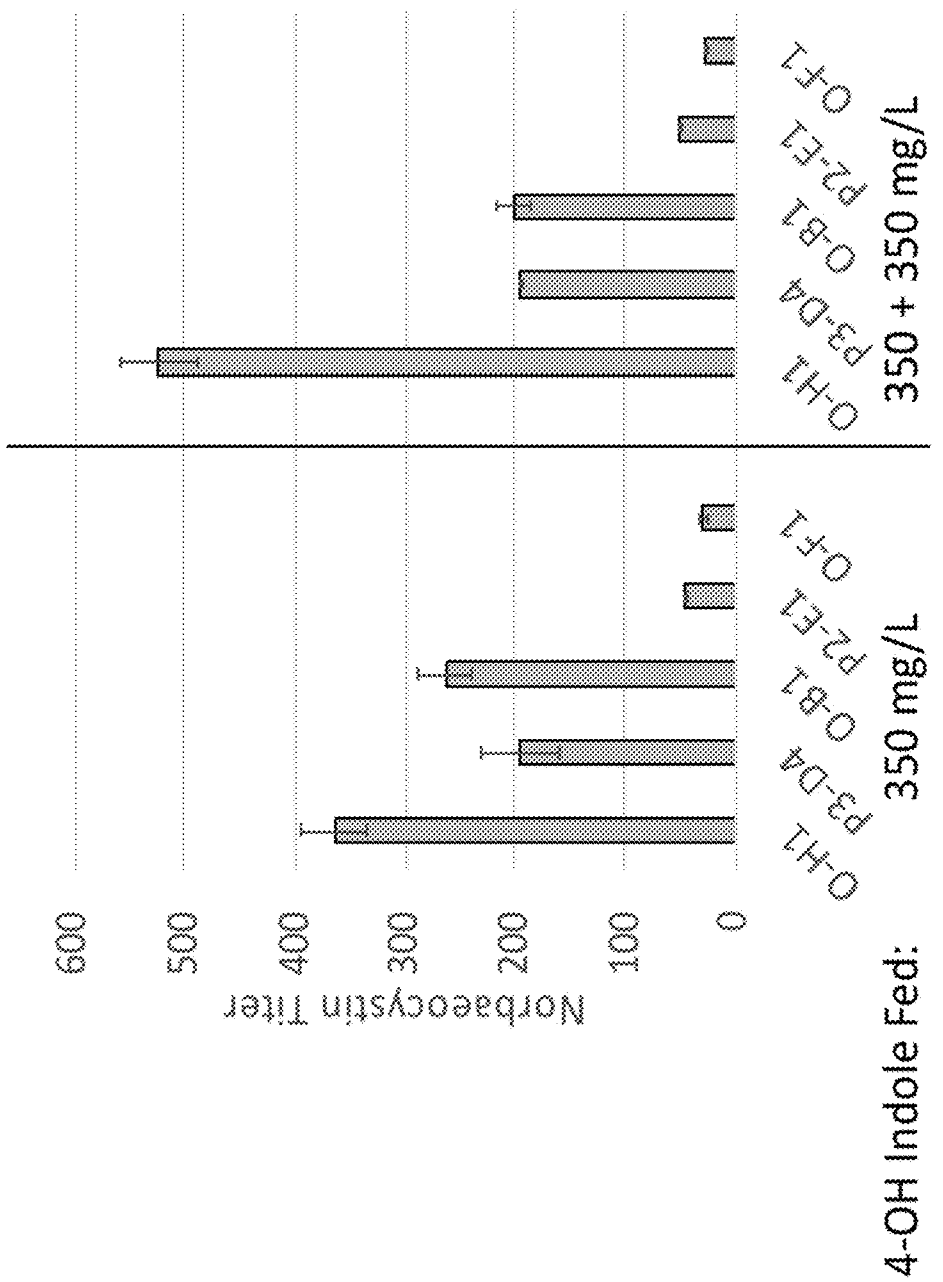
FIG. 6 is a graph showing norbaeocystin production after additional 4-hydroxyindole exposure to evaluate production in a non-substrate limited environment.
Figure 7A:
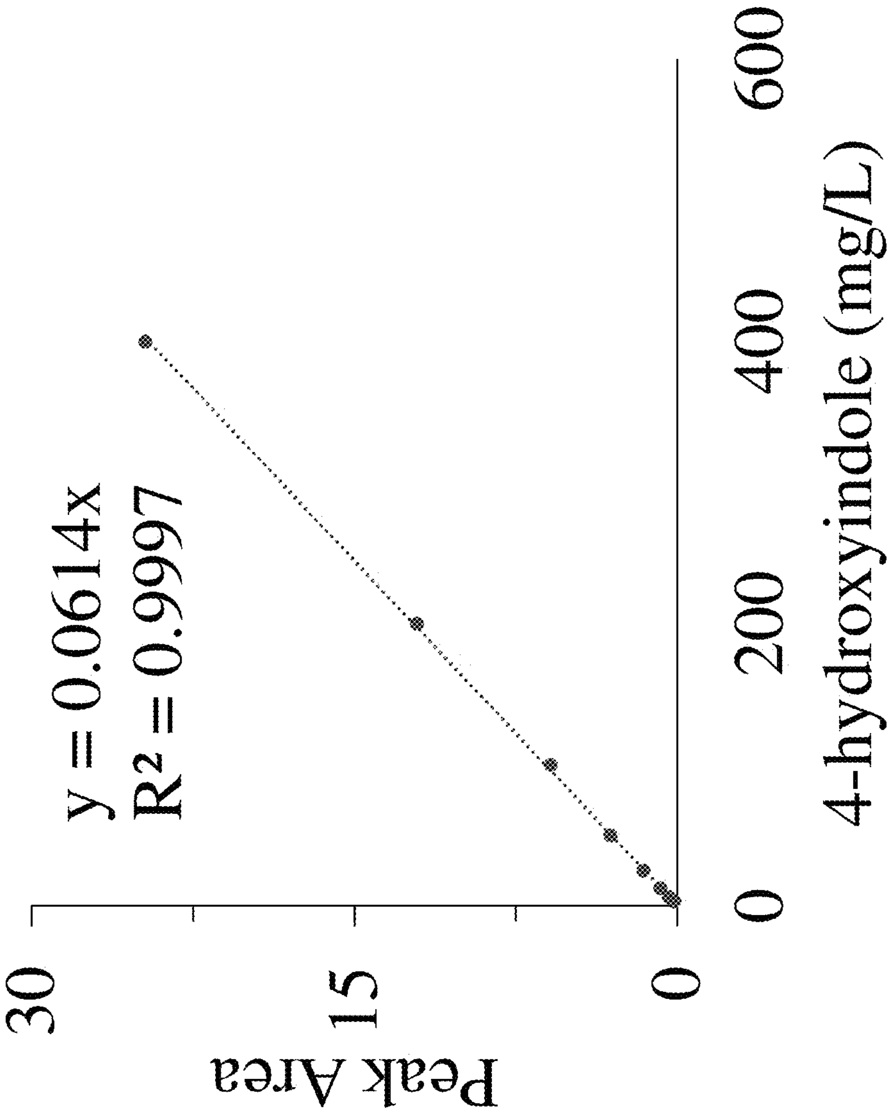
FIGS. 7A-7D show HPLC standard curves used for metabolite quantification: 4-hydroxyindole (FIG. 7A), 5-hydroxytryptophan (FIG. 7B), 5-hydroxytryptamine (FIG. 7C), psilocybin (FIG. 7D).
Figure 7B:
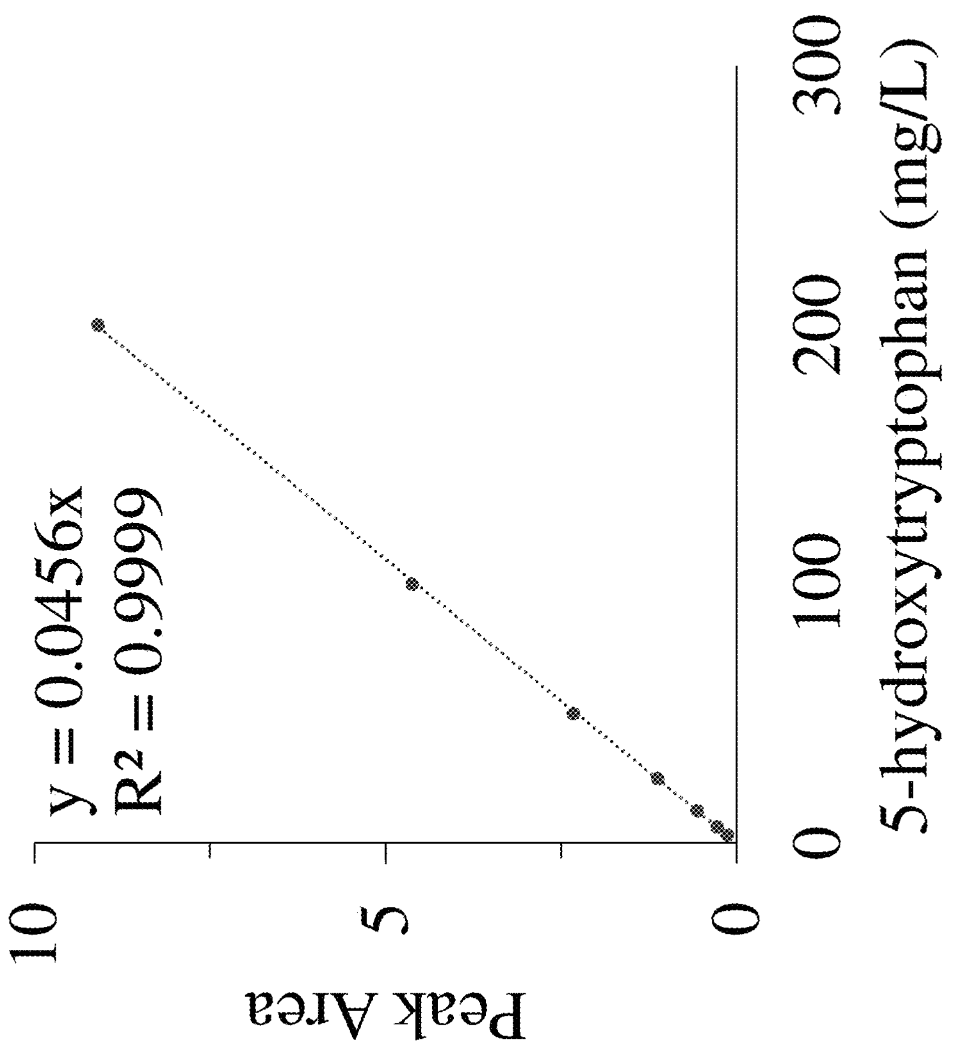
Figure 7C:
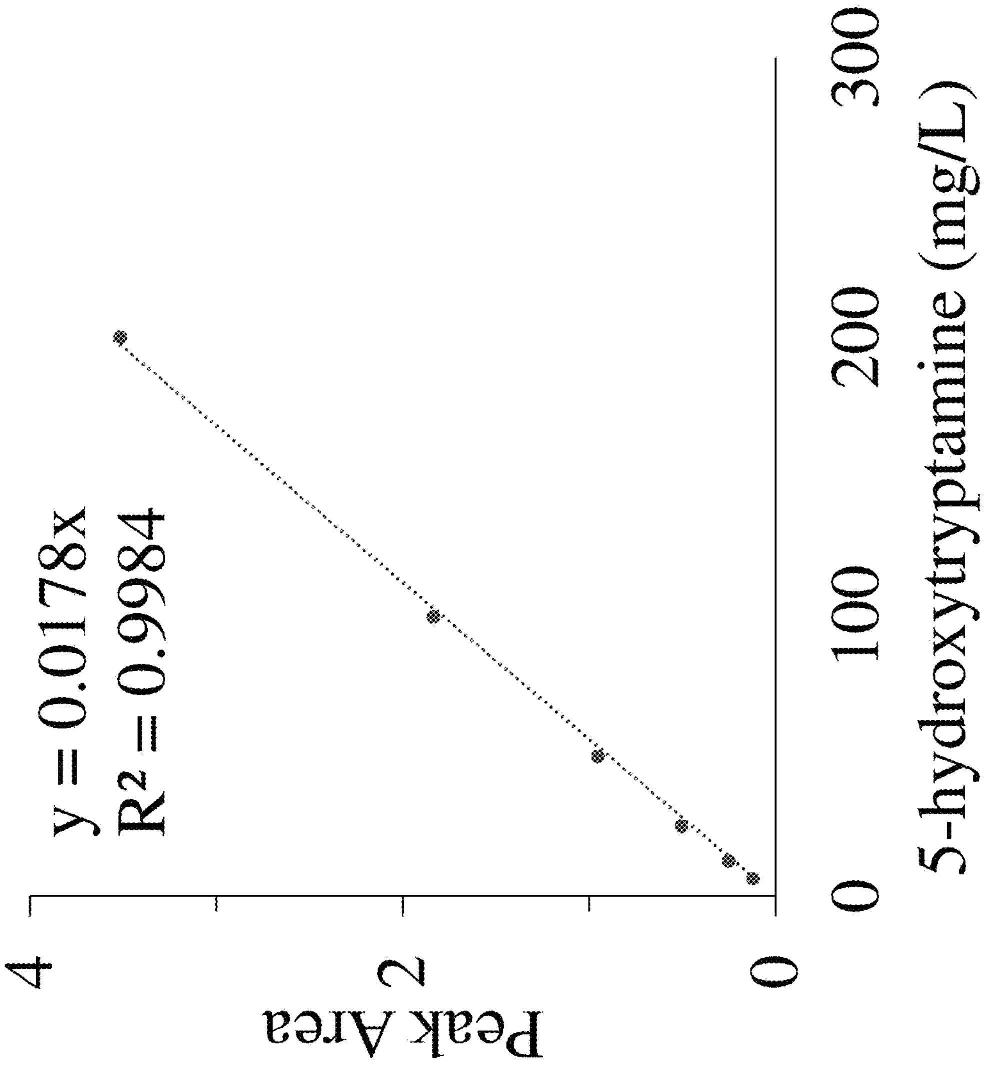
Figure 7D:
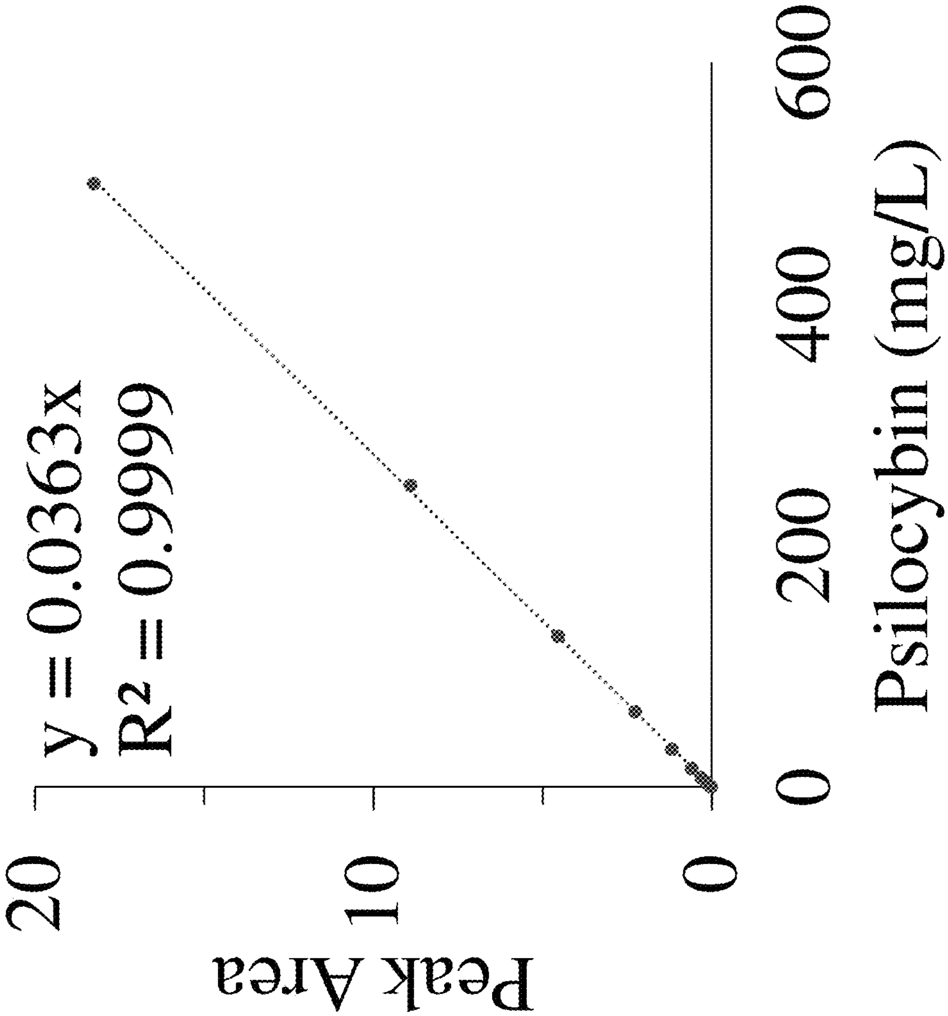
Figure 8:
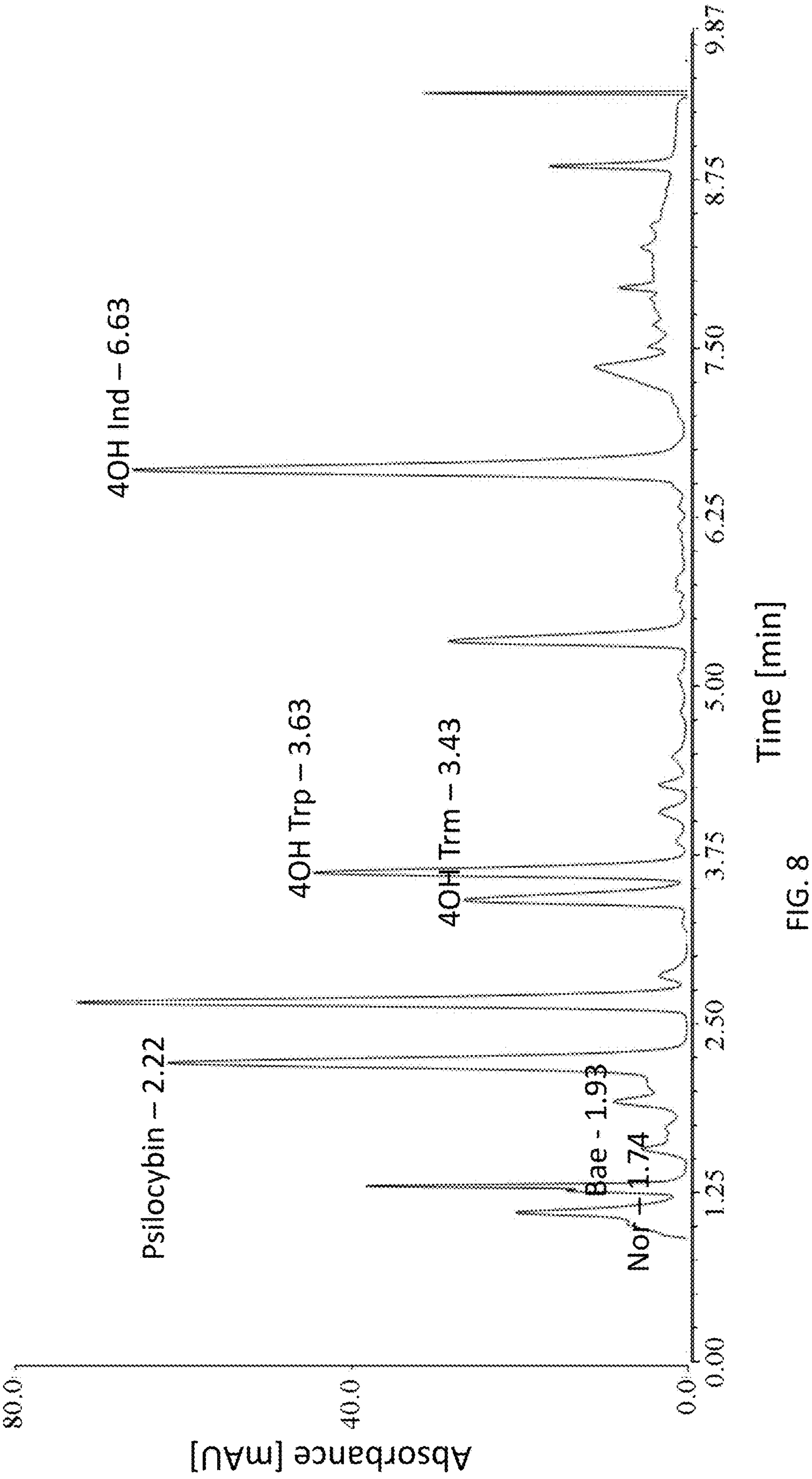
FIG. 8 shows an example chromatogram (280 nm) for HPLC method (1 mL/min) with retention times listed. The data was obtained from a sample of cell-free broth supernatant from an optimized psilocybin production host selected to have major peaks for all relevant metabolites.
Figure 9A:
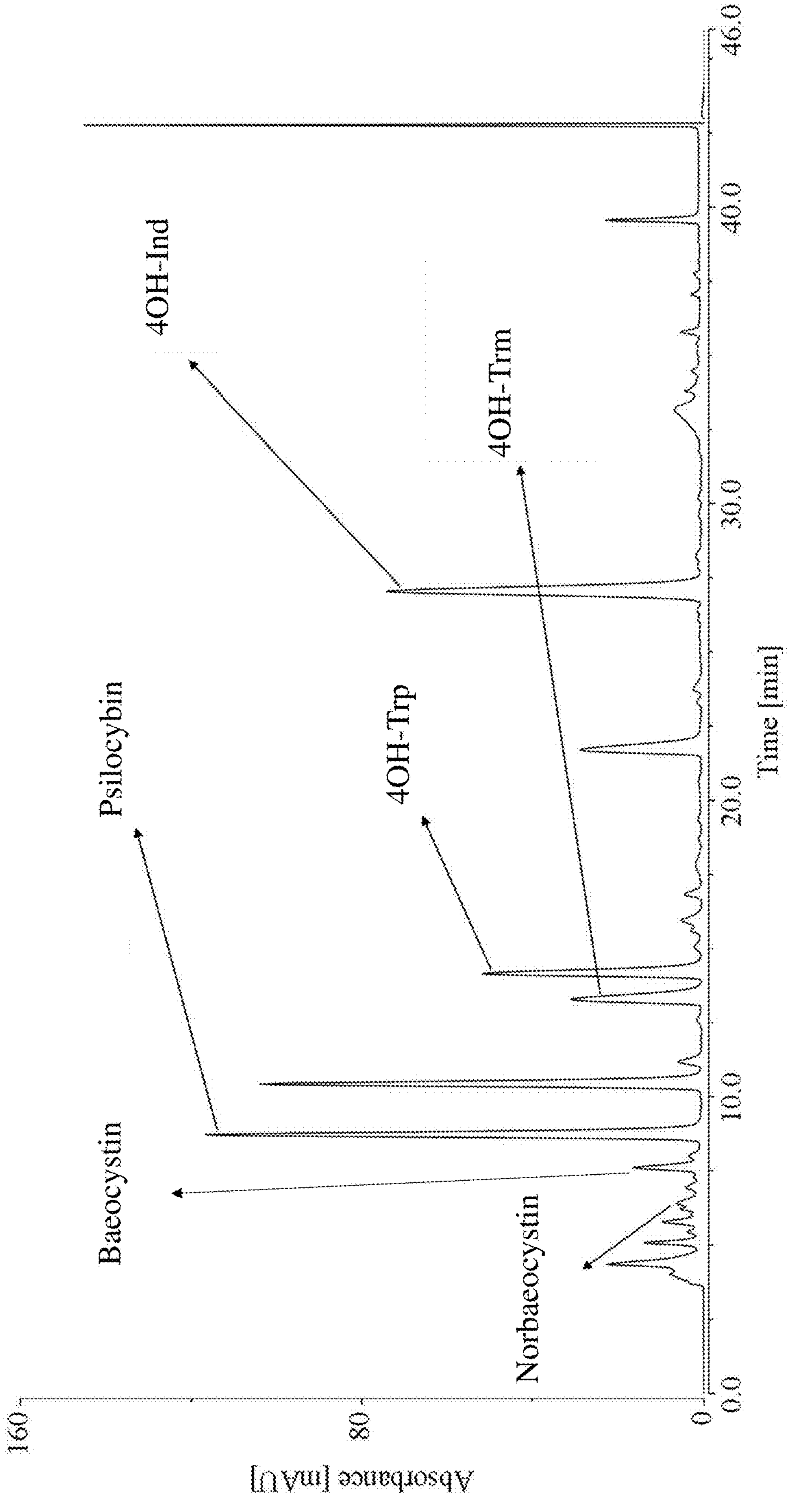
FIGS. 9A-9G show an example chromatogram (280 nm) for LC-MS method (0.25 mL/min) with retention times, MS and MS/MS fragmentation shown. The data was obtained from a sample of cell-free broth supernatant from an optimized psilocybin production host selected to have major peaks for all relevant metabolites (FIG. 9A).
Figure 9B:
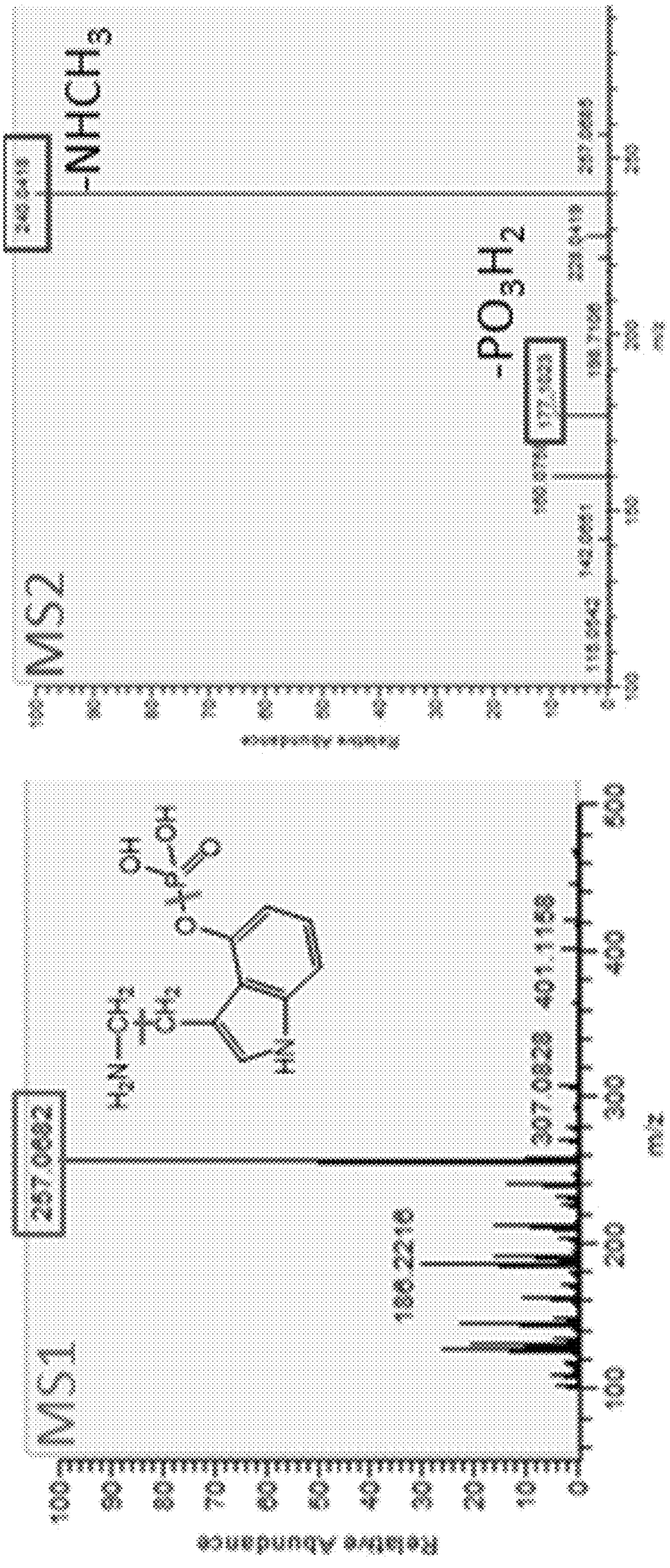
Figure 9C:
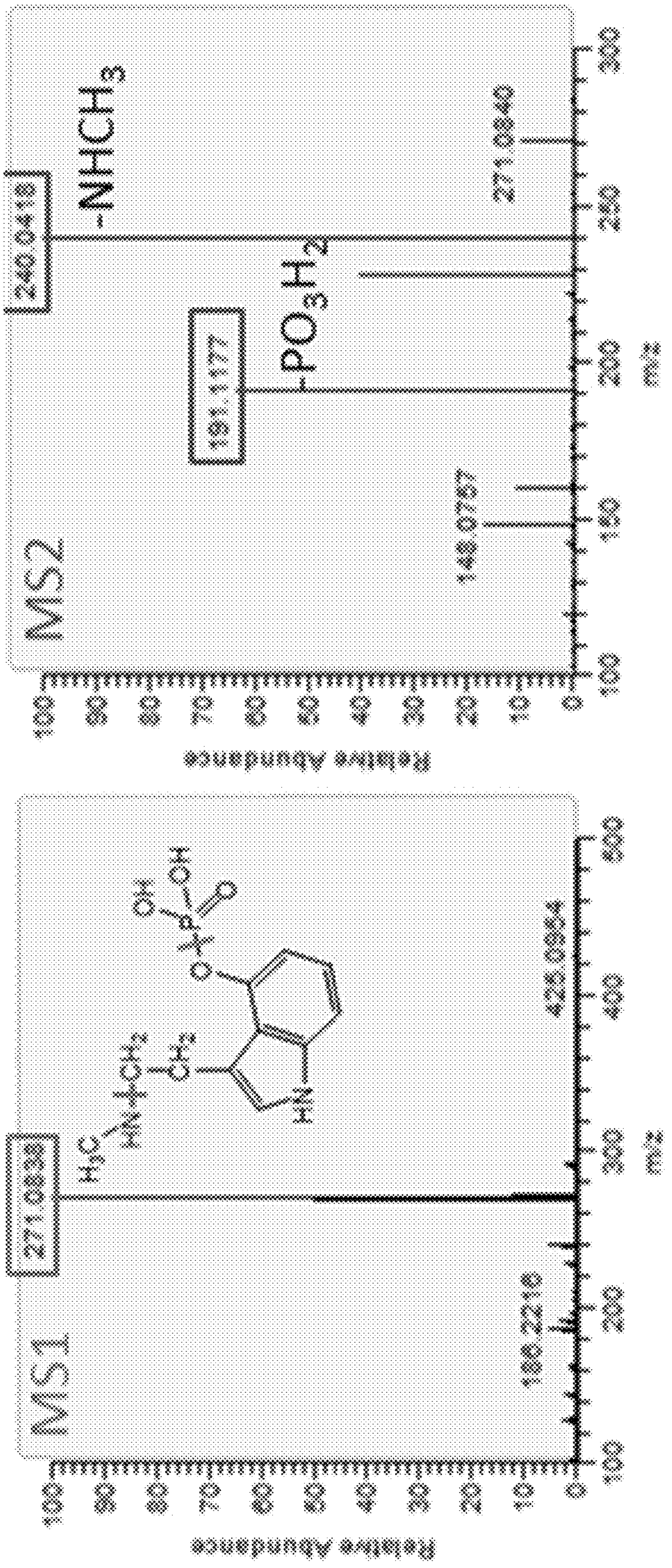
Figure 9D:
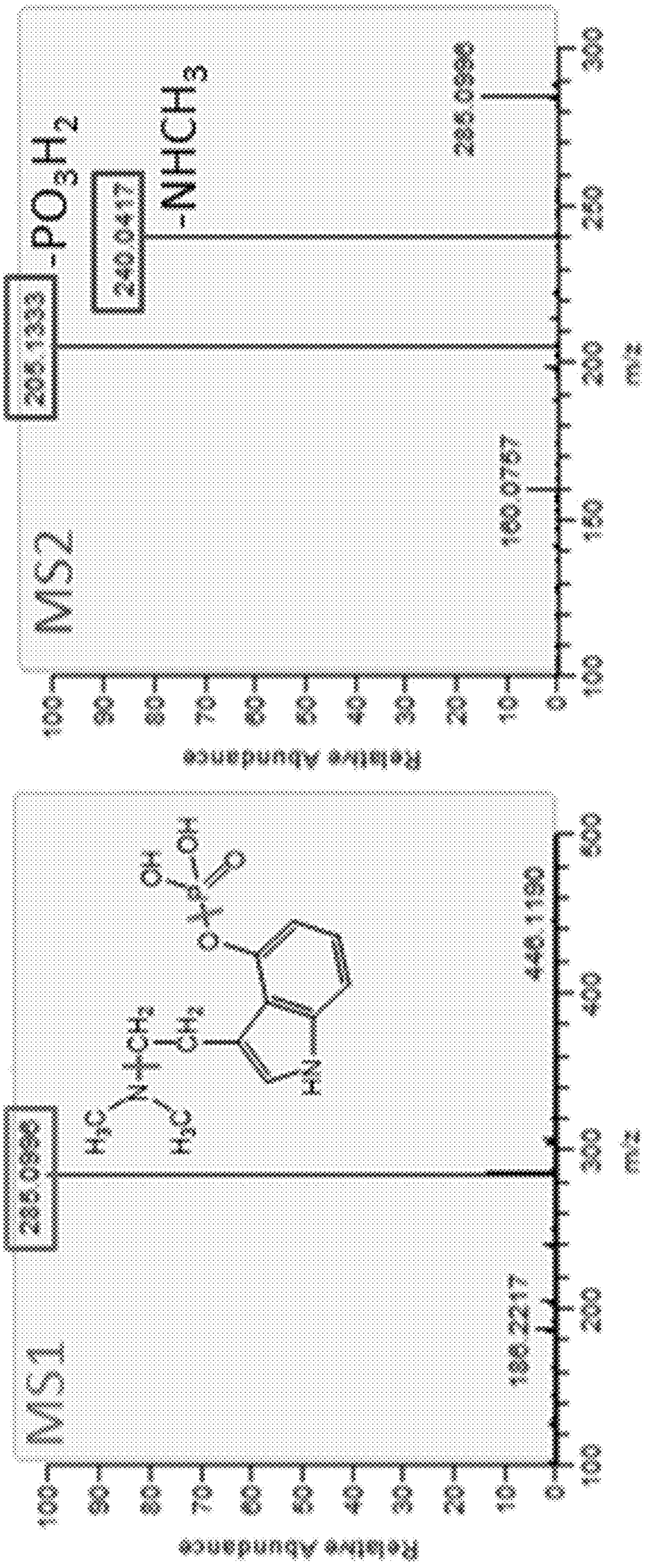
Figure 9E:
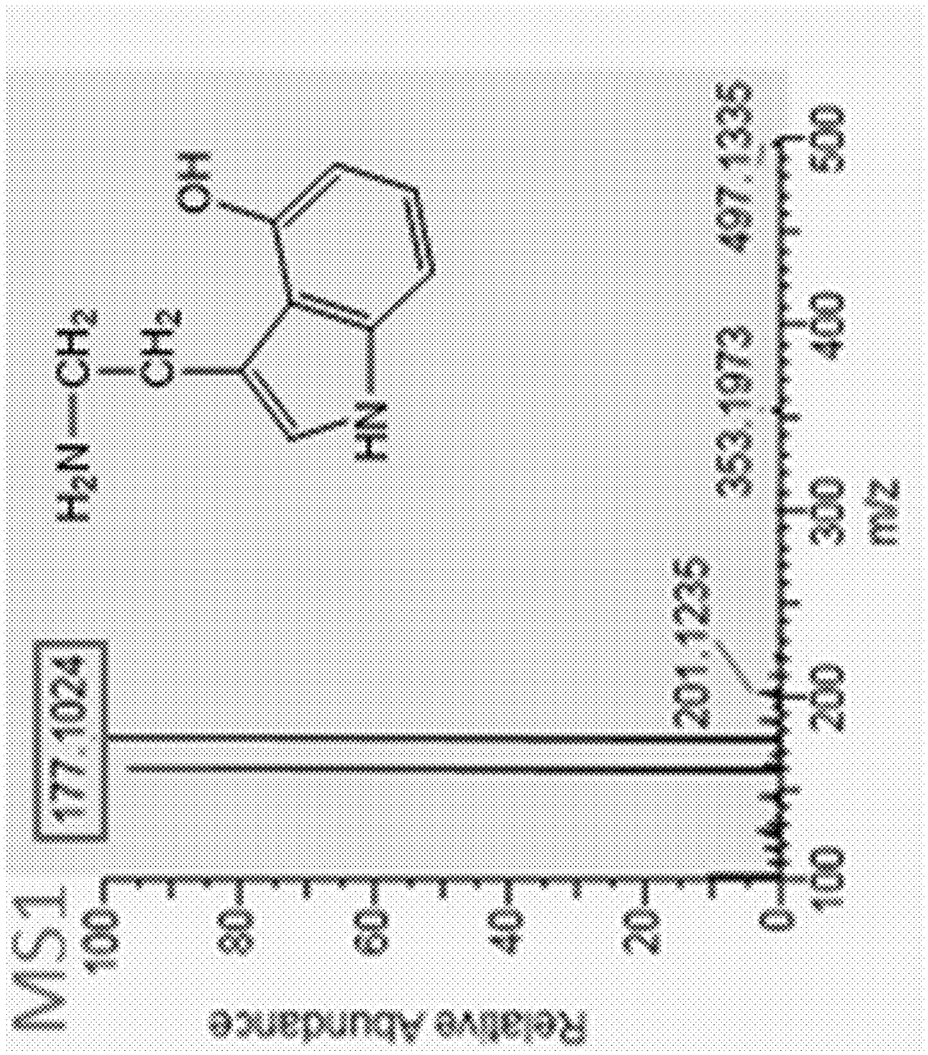
Figure 9F:
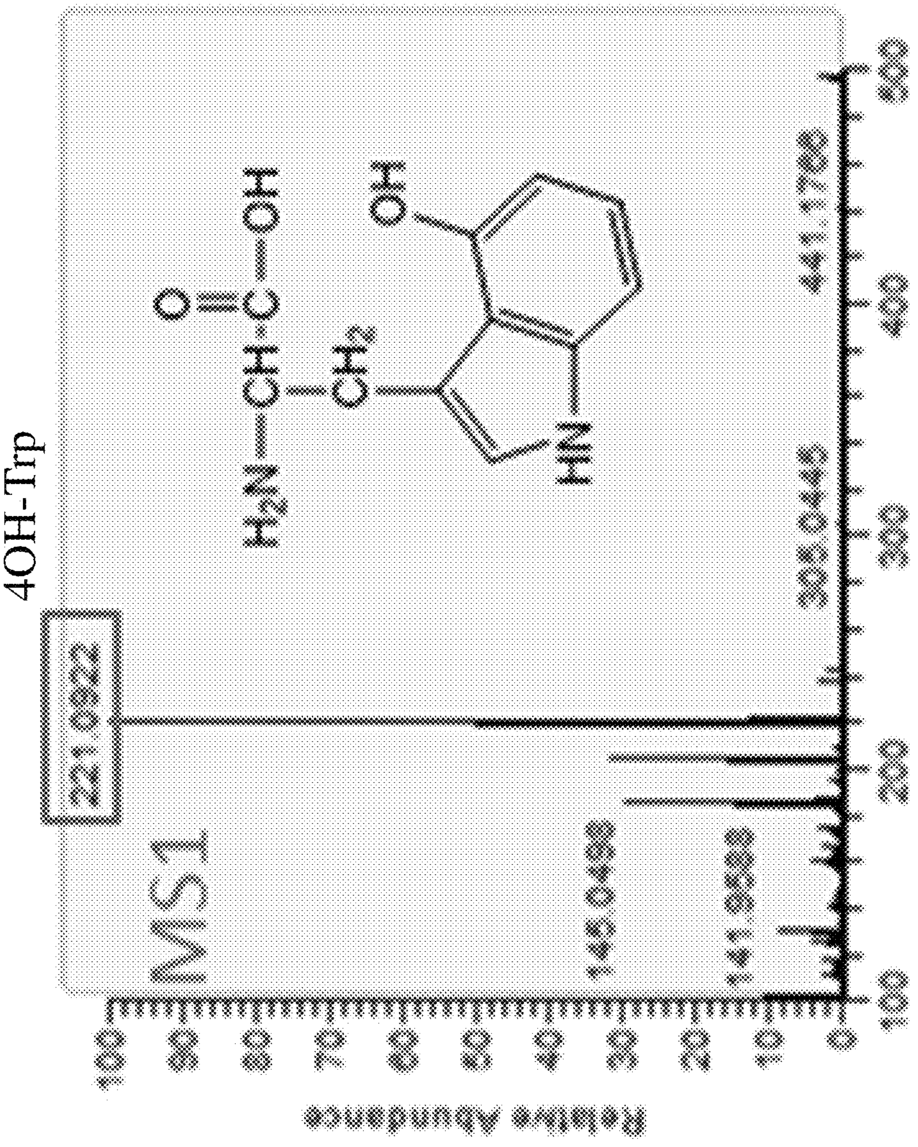
Figure 9G:
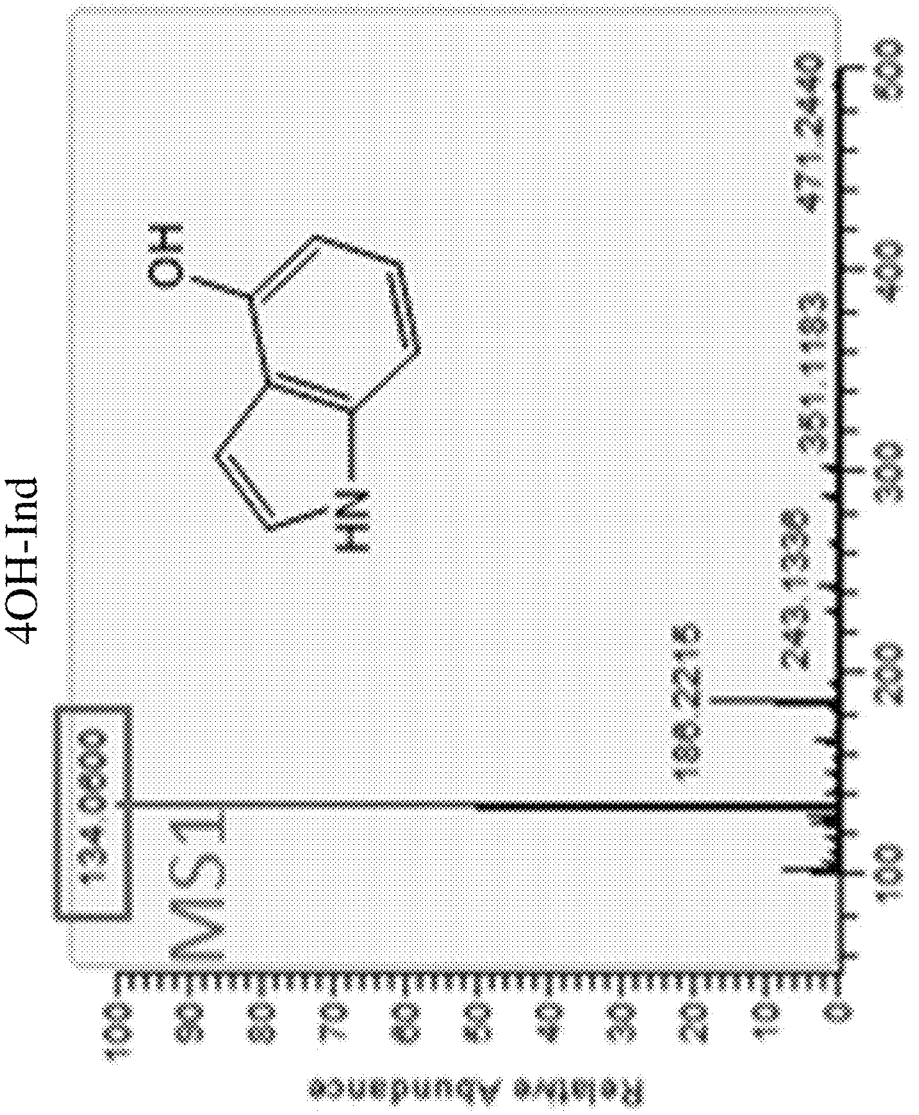
Figure 10:
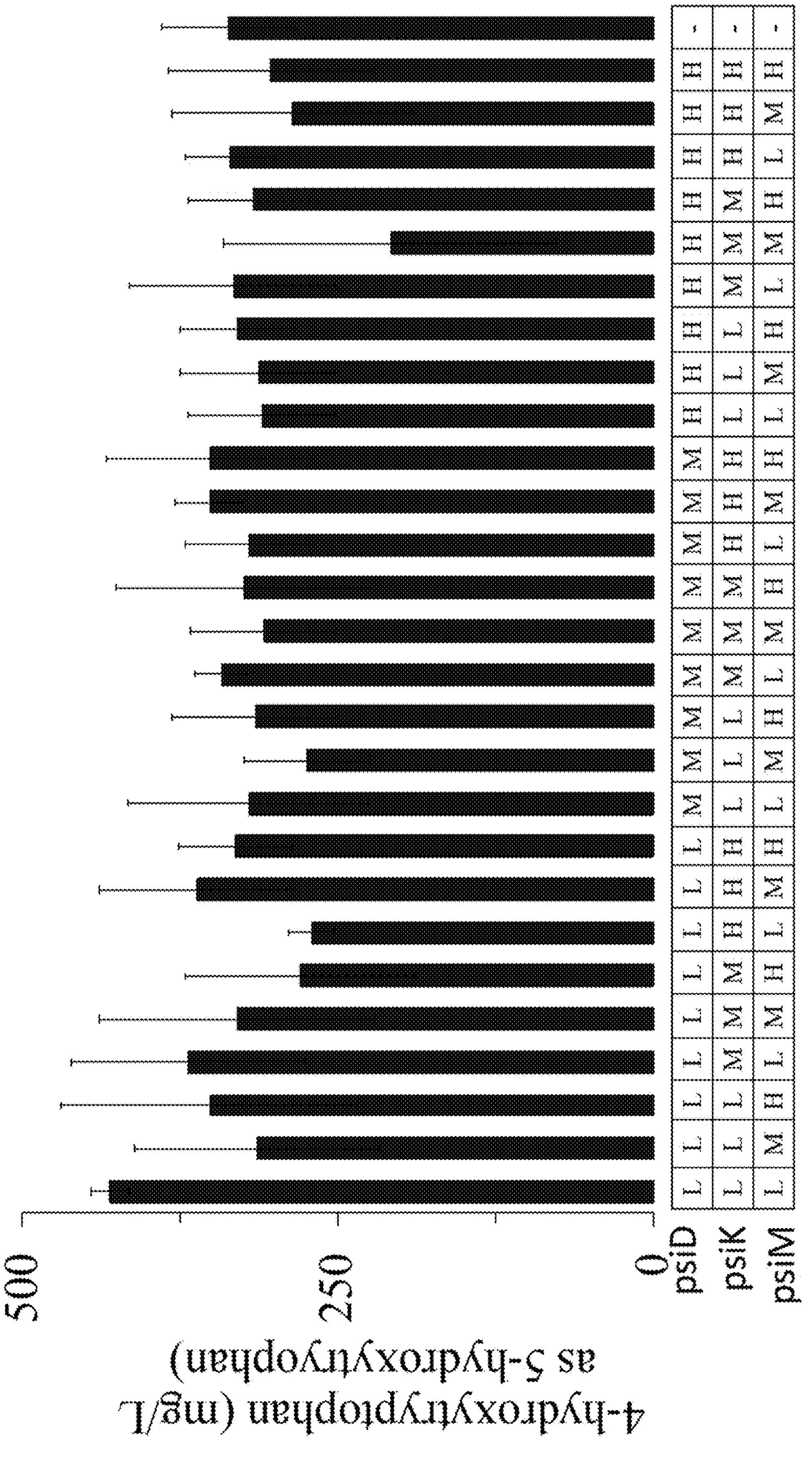
FIG. 10 shows 4-hydroxytryptophan analysis in copy number library. 4-hydroxytryptophan was quantified based on the standard curve of 5-hydroxytryptophan due to limited commercial availability and high cost of the authentic standard. Error bars represent ±1 standard deviation from the mean of triplicate samples.
Figure 11:
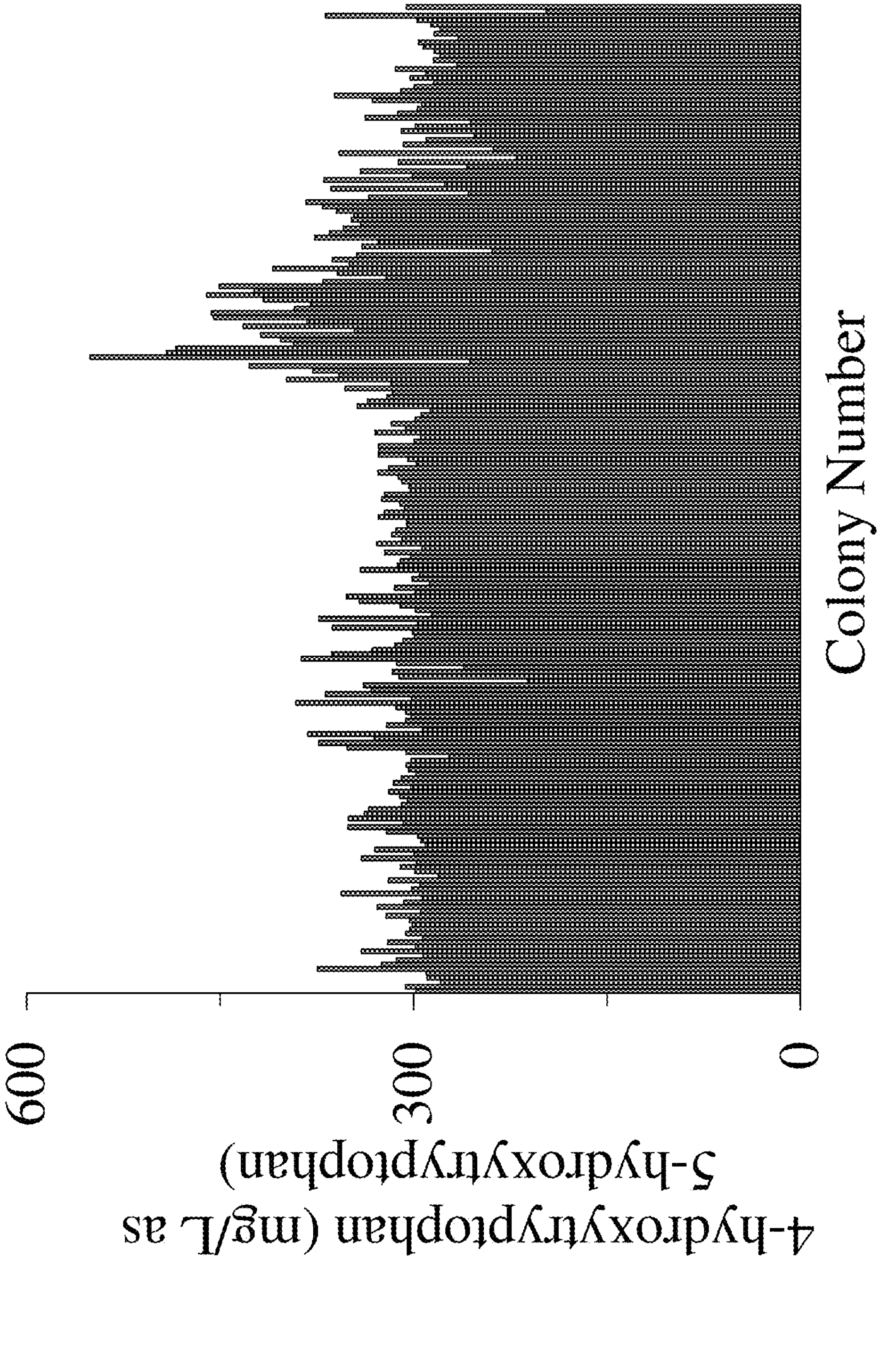
FIG. 11 shows 4-hydroxytryptophan analysis in pseudooperon library. Variants are presented in order of decreasing psilocybin production to enable comparison with FIG. 2B. 4-hydroxytryptophan was quantified based on the standard curve of 5-hydroxytryptophan due to limited commercial availability and high cost of the authentic standard.
Figure 12:
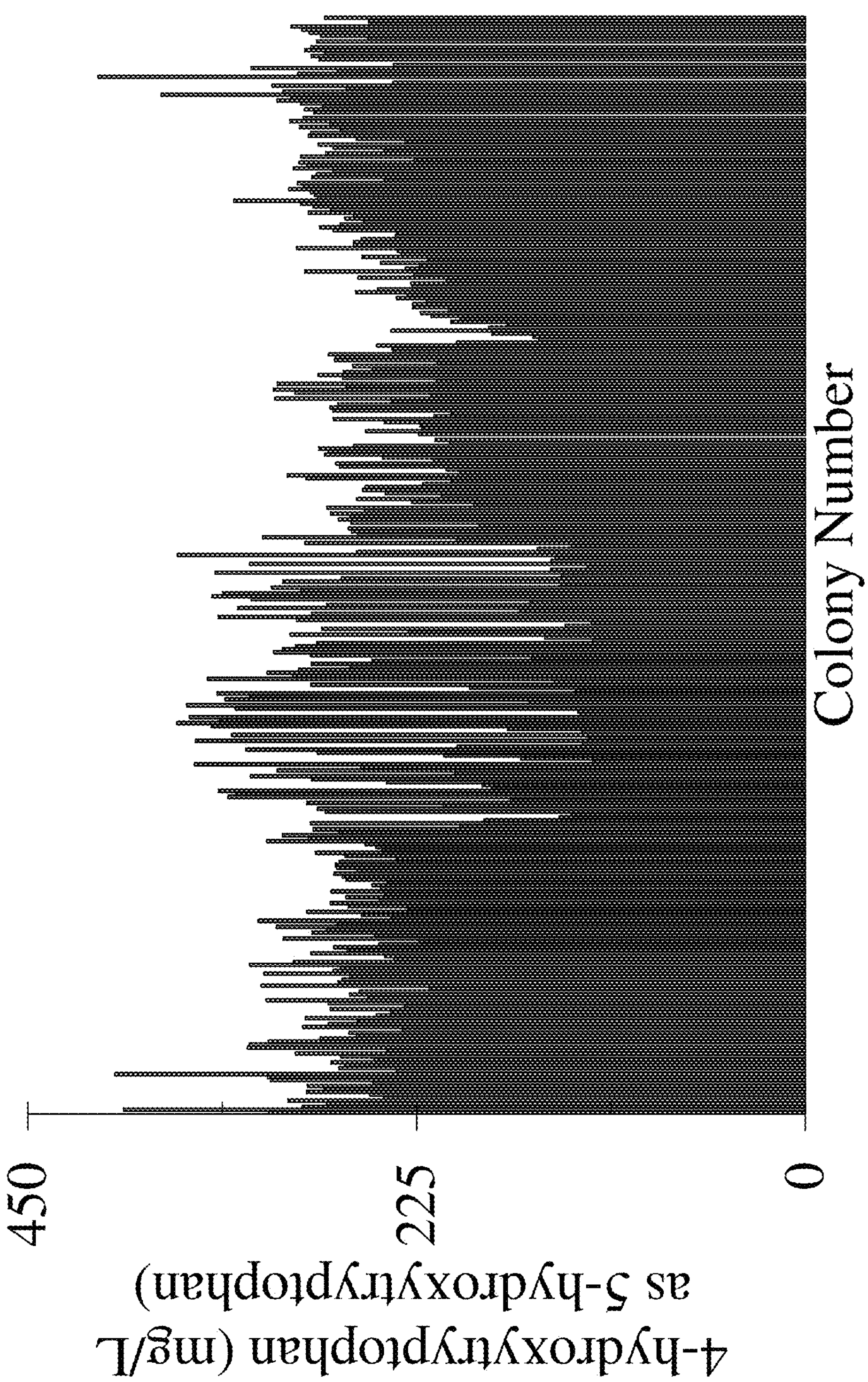
FIG. 12 shows 4-hydroxytryptophan analysis in basic operon library. Variants are presented in order of decreasing psilocybin production to enable comparison with FIG. 2C. 4-hydroxytryptophan was quantified based on the standard curve of 5-hydroxytryptophan due to limited commercial availability and high cost of the authentic standard.
Figure 13:
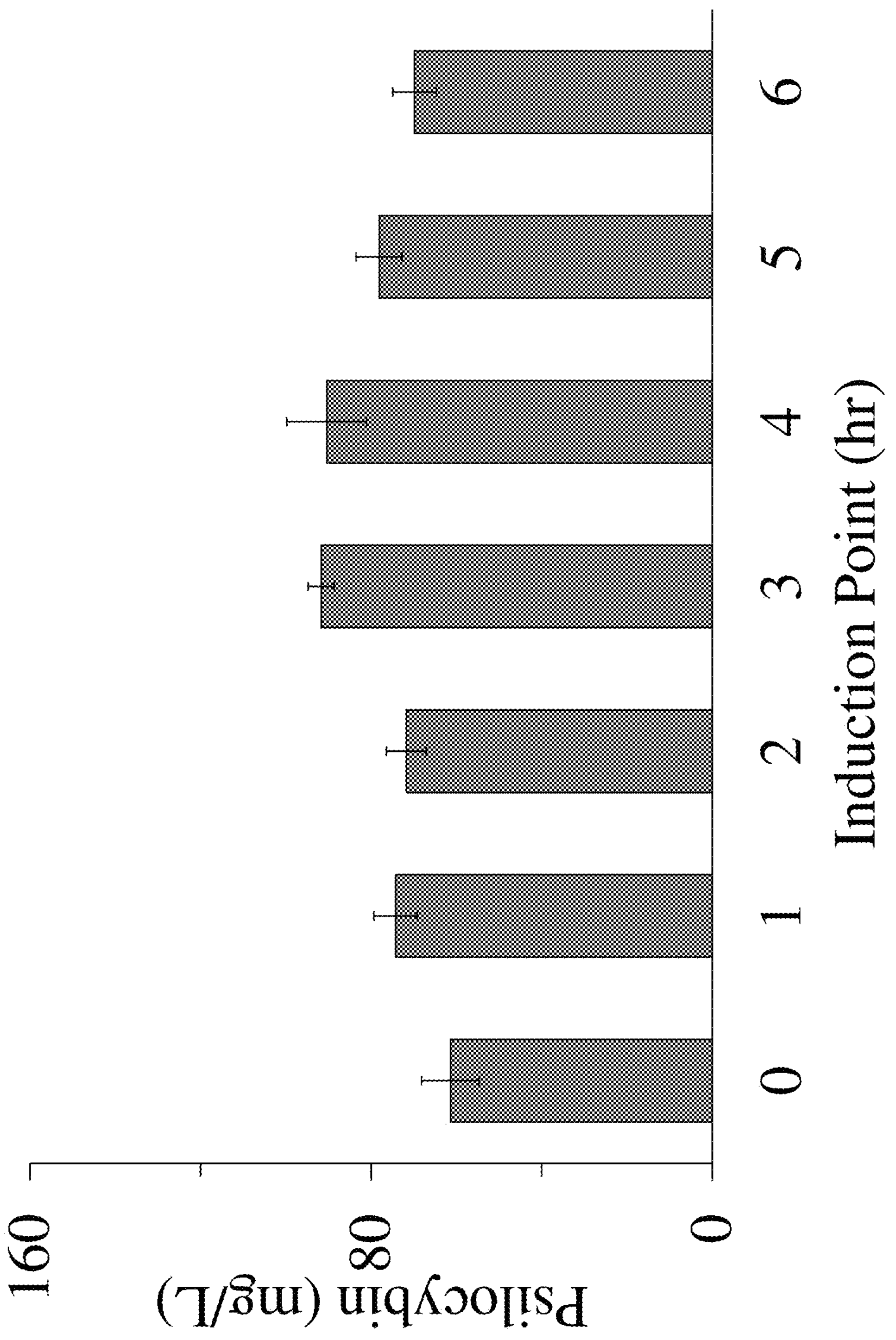
FIG. 13 shows induction sensitivity of pPsilo16 at 37° C. from 0 to 6 hours. Error bars represent ±1 standard deviation from the mean of duplicate samples.
Figure 14:
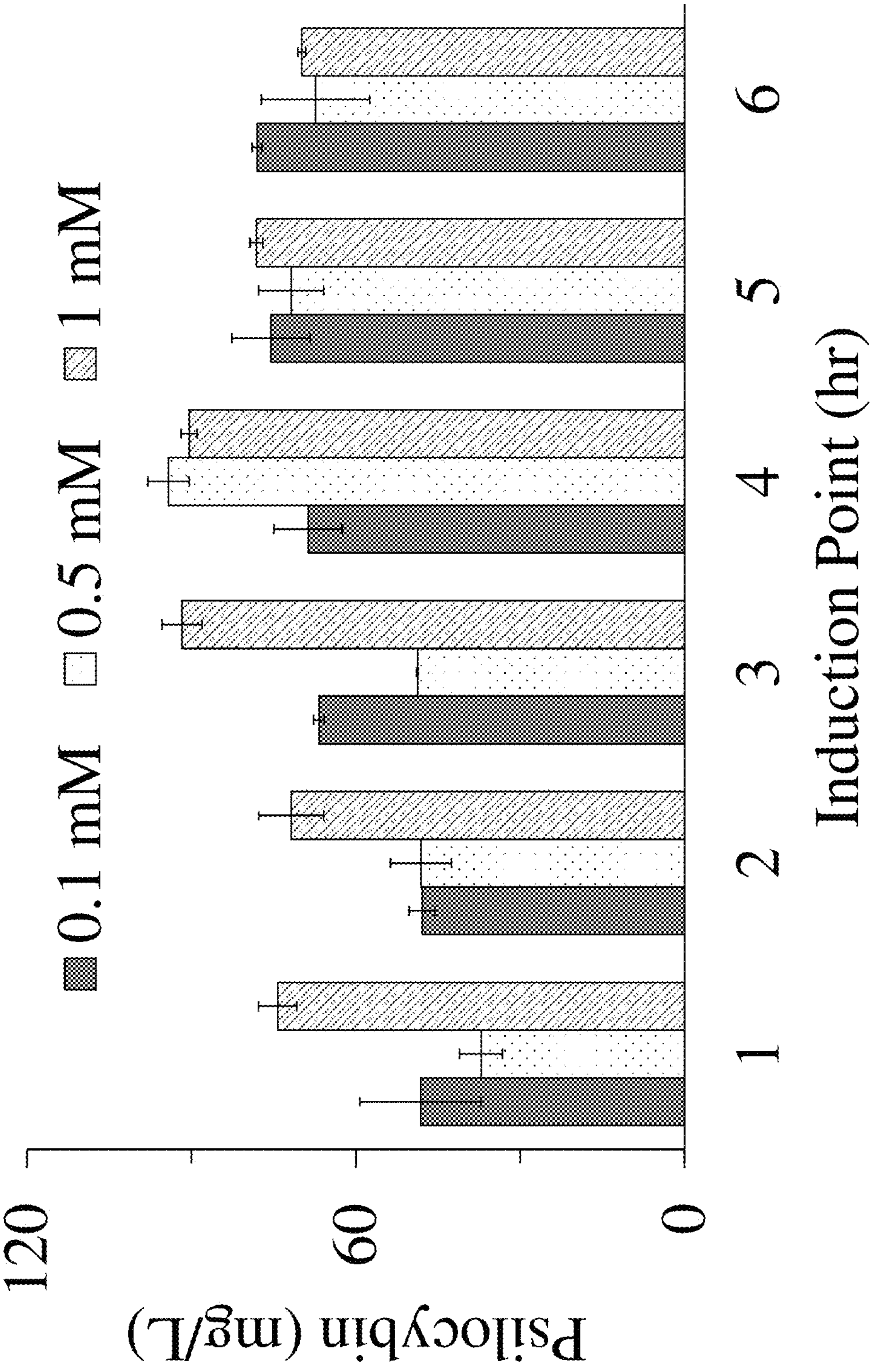
FIG. 14 shows induction point sensitivity analysis for pPsilo16 growing in AMM—Glucose at different inducer concentrations. Error bars represent ±1 deviation from the mean of duplicate samples.
Figure 15:
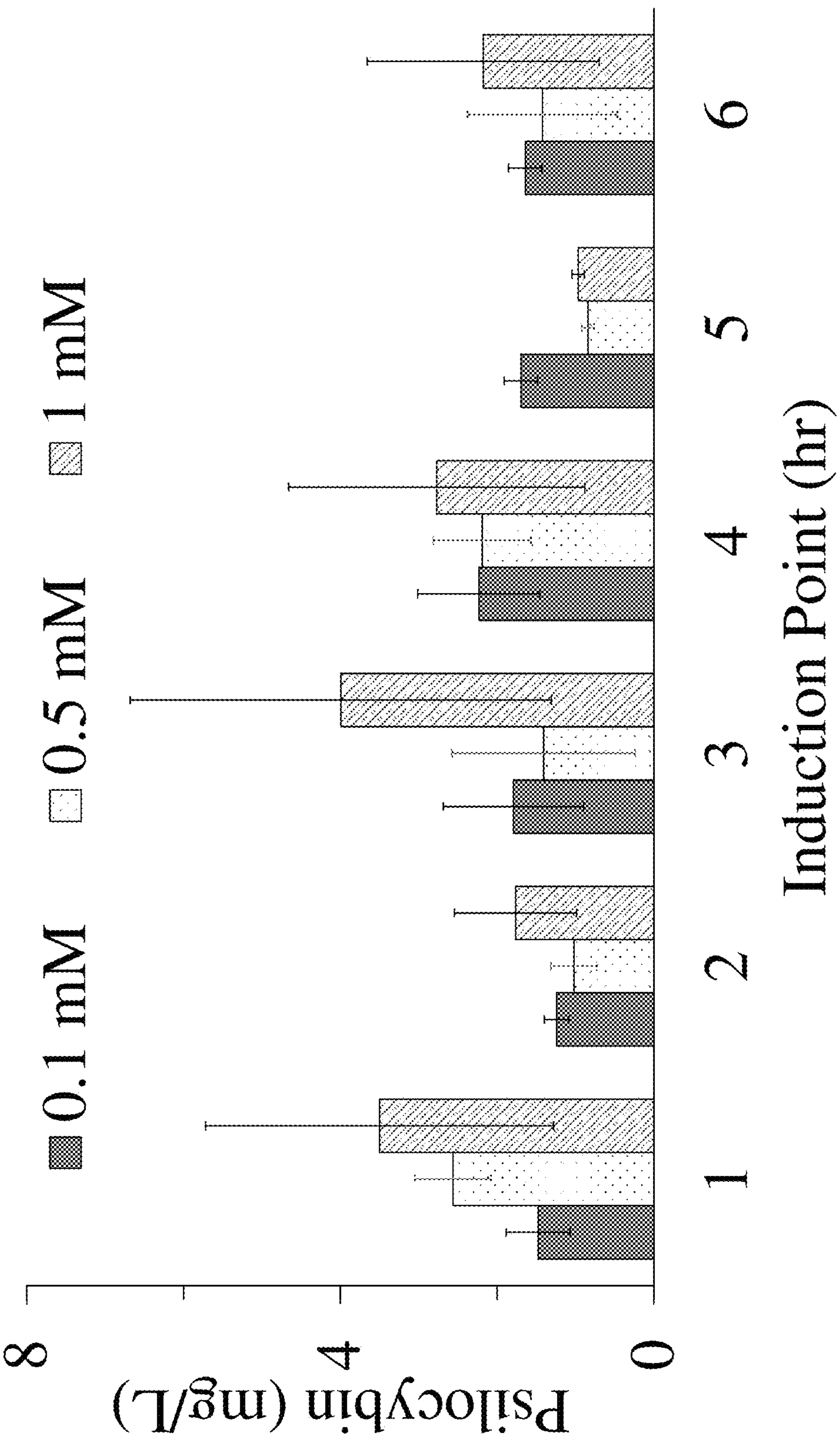
FIG. 15 shows induction point sensitivity analysis for pPsilo16 growing in AMM—Glycerol at different inducer concentrations. Error bars represent ±1 deviation from the mean of duplicate samples.
Figure 16:
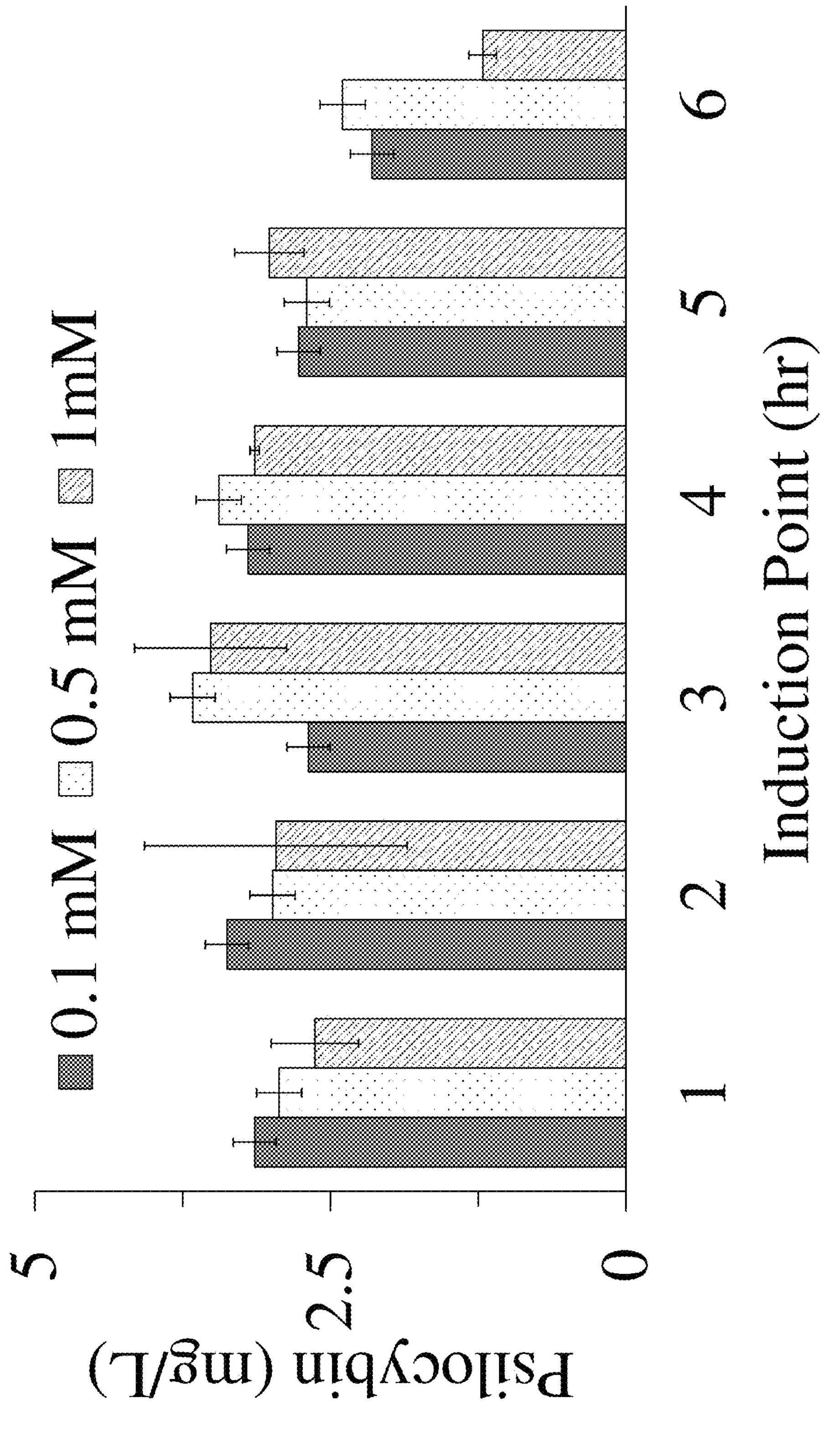
FIG. 16 shows induction point sensitivity analysis for pPsilo16 growing in LB at different inducer concentrations. Error bars represent ±1 deviation from the mean of duplicate samples.

The select mutants were additionally screened after plasmid retransformation to confirm their norbaeocystin production capability. Additionally, all selected mutants were also given additional 4-hydroxyindole to further evaluate their production in a non-substrate limited environment (FIG. 6, right). Upon rescreening, the mutants maintained their high titer production with the top mutant, O—H1, showing production just under 400 mg/L. Adding an additional 350 mg/L of the 4-hydroxyindole substrate approximately 24 hours after inoculation resulted in a significant ($p<0.05$) enhancement in overall titer for the best producing mutant, O—H1, to over 0.5 g/L of norbaeocystin in a 48-well plate fermentation assay.

Example 3: Optimization of Production of Norbaeocystin

Materials and Methods

The top norbaeocystin production strain identified from the library screens, O—H1 (Table 1), was subjected to scaleup screening in a 1.5-L working volume bioreactor controlled by the Eppendorf BioFLO120 system. This bioreactor system was operated as described above for the psilocybin scale up study (Example 1).

Figure 19:
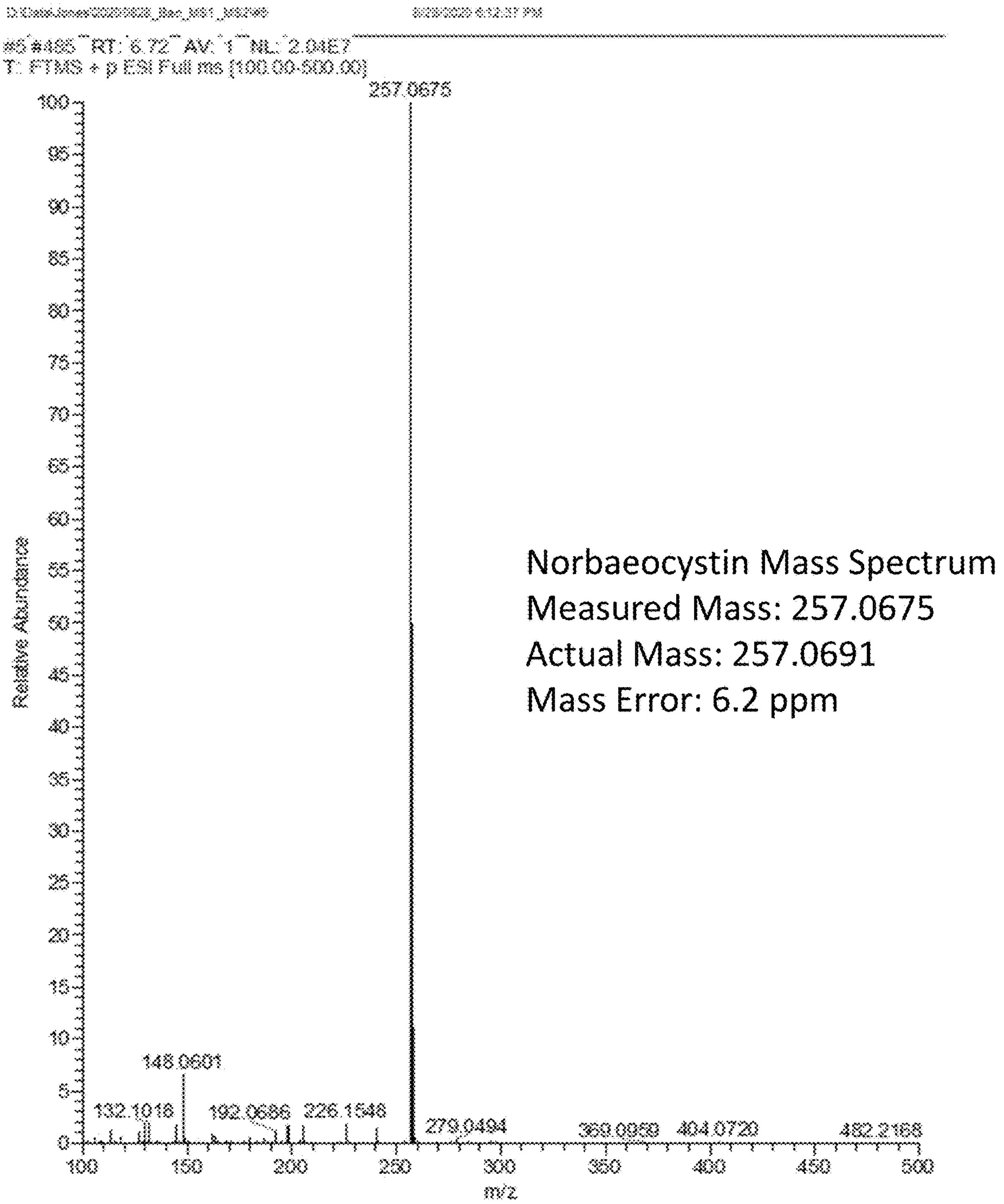
FIG. 19 shows a full mass spectrum of norbaeocystin produced via *E. coli* fermentation. This data was taken using a Thermo Scientific Orbitrap XL Mass Spectrometer in positive ion mode. The measured mass is in agreement with the actual mass of norbaeocystin to 5 significant figures, further confirming the identity of norbaeocystin in the fermentation broth.

Norbaeocystin was quantified as described above using a psilocybin standard curve due to the lack of a commercially available analytical standard. Norbaeocystin identity was verified using an accurate mass OrbitrapXL spectrometer (FIG. 19). The measured mass resulted in an acceptable error of 6.2 ppm.

Results

Figure 18:
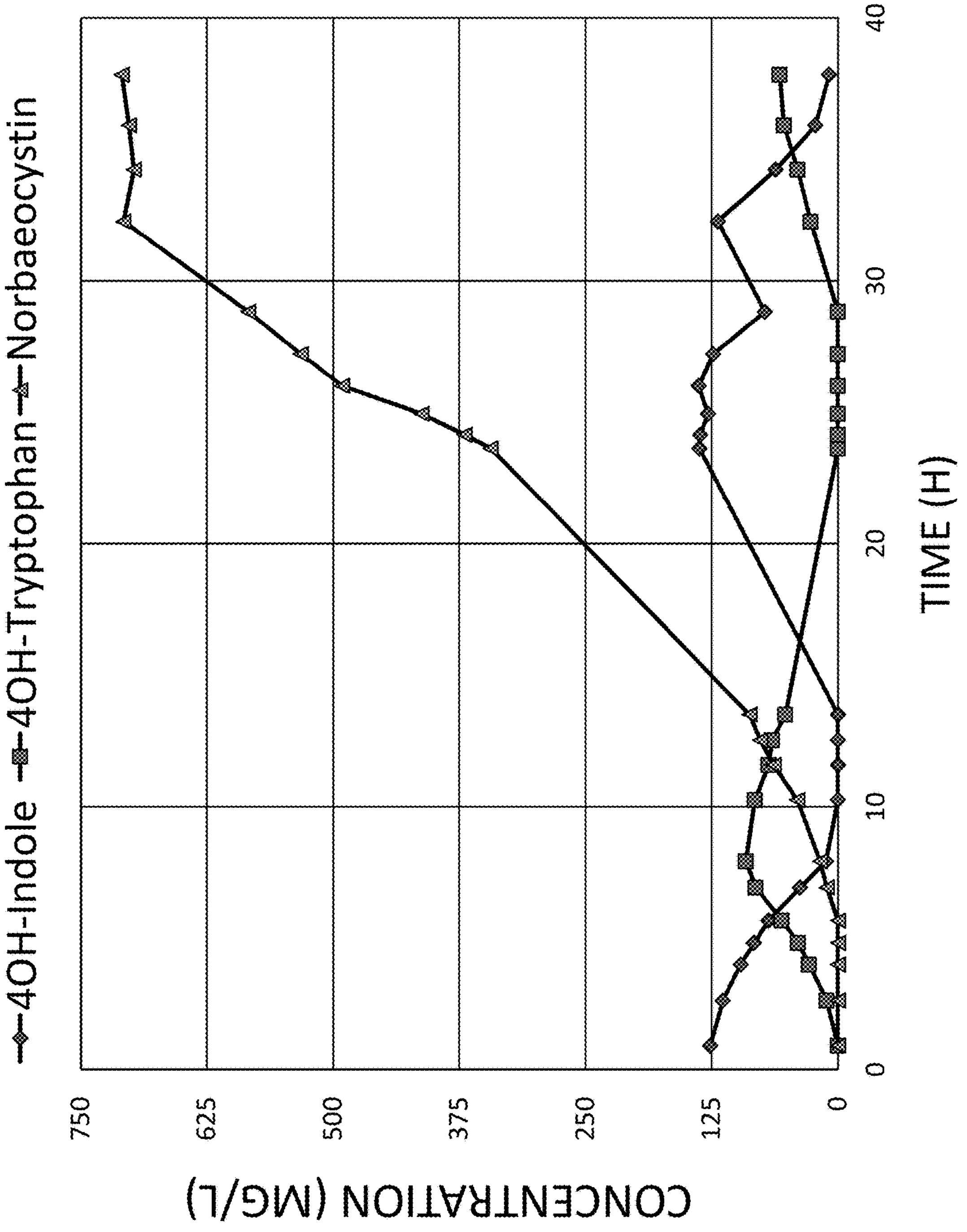
FIG. 18 shows data for a fed-batch bioreactor study for the high-level production of norbaeocystin in *E. coli*. Transient data for the target product, norbaeocystin, as well as intermediate product, 4-hydroxytryptophan, and starting substrate, 4-hydroxyindole is shown for the 38-hour fermentation process. 4-hydroxyindole was provided continuously using a syringe pump as to limit the accumulation of 4-hydroxytryptophan during the fermentation.

The concentration of psilocybin and other key intermediates were tracked over the course of the fed-batch bioreactor study. The results of this HPLC analysis are shown in FIG. 18. The figure shows that the intermediate product, 4-hydroxytryptophan, and the 4-hydroxyindole substrate were maintained below inhibitory levels throughout the fermentation. This was achieved by using an HPLC-informed feeding strategy coupled with frequent sampling and analysis. This study resulted in the production of 700 mg/L of norbaeocystin over 32 hours. This is the first reported example of norbaeocystin production from a prokaryotic host.

TABLE 2

Plasmid and Strain List

| Number | Strain or vector | Relevant properties | Reference |
|---|---|---|---|
| S1 | *Escherichia coli* DH5a | F-, φ80d lacZΔM15, Δ(lacZYA-argF)U169, recA1, endZ1, hsdR17(rk$^-$, mk$^+$), phoA, supE44λ$^-$, thi$^{-1}$, gyrA96, relA1 | Novagen |
| S2 | *E. coli* BL21 Star™ (DE3) | F- ompT gal dcm rne131 ion hsdS$_B$ (rB-mB-) λ(DE3) | Invitrogen |
| 1 | pJF24 | pET28a containing tryptophan decarboxylase from *Psilocybe cubensis* (PcPsiD), Kan$^R$ | (Fricke et al., 2017) |
| 2 | pJF23 | pET28a containing Kinase from *Psilocybe cubensis* (PcPsiK), Kan$^R$ | (Fricke et al., 2017) |
| 3 | pFB13 | pET28a containing SAM-dependant methyl transferase from *Psilocybe cubensis* (PcPsiM), Kan$^R$ | (Fricke et al., 2017) |
| 4 | pETM6 | ColE1(pBR322), Amp$^R$ | (Xu et al., 2012) |
| 5 | pACM4 | P15A(pACYC184), Cm$^R$ | (Xu et al., 2012) |
| 6 | pCDM4 | CloDF13, Str$^R$ | (Xu et al., 2012) |
| 7 | pETM6-SDM2x | #4 with XbaI and XmaJI sites swtiched | This Study |
| 8 | pACM4-SDM2x | #5 with XbaI and XmaJI sites swtiched | This Study |
| 9 | pCDM4-SDM2x | #6 with XbaI and XmaJI sites swtiched | This Study |
| 10 | pETM6-SDM2x-psiD | #7 containing psiD | This Study |
| 11 | pETM6-SDM2x-psiK | #7 containing psiK | This Study |
| 12 | pETM6-SDM2x-psiM | #7 containing psiM | This Study |
| 13 | pETM6-SDM2x-psiDK | #7 containing psiDK in pseudooperon configuration | This Study |
| 14 | pETM6-SDM2x-psiKM | #7 containing psiKM in pseudooperon configuration | This Study |
| 15 | pETM6-SDM2x-psiDKM (All-High) | #7 containing psiDKM in pseudooperon | This Study |
| 16 | pACM4-SDM2x-psiD | #8 containing psiD | This Study |
| 17 | pACM4-SDM2x-psiK | #8 containing psiK | This Study |
| 18 | pACM-SDM2x-psiM | #8 containing psiM | This Study |
| 19 | pACM4-SDM2x-psiDK | #8 containing psiDK in pseudooperon configuration | This Study |
| 20 | pACM4-SDM2x-psiKM | #8 containing psiKM in pseudooperon configuration | This Study |
| 21 | pACM4-SDM2x-psiDKM | #8 containing psiDKM in pseudooperon configuration | This Study |
| 22 | pCDM4-SDM2x-psiD | #9 containing psiD | This Study |
| 23 | pCDM4-SDM2x-psiK | #9 containing psiK | This Study |
| 24 | pCDM4-SDM2x-psiM | #9 containing psiM | This Study |
| 25 | pCDM4-SDM2x-psiDK | #9 containing psiDK in pseudooperon configuration | This Study |
| 26 | pCDM4-SDM2x-psiKM | #9 containing psiKM in pseudooperon configuration | This Study |
| 27 | pCDM4-SDM2x-psiDKM | #9 containing psiDKM in pseudooperon configuration | This Study |
| 28 | pPsilo16 | pETM6-SDM2x-psiDKM in basic operon configuration with T7 mutant promoter H10 | This Study |

TABLE 2-continued

| Plasmid and Strain List | | | |
|---|---|---|---|
| Number | Strain or vector | Relevant properties | Reference |
| | | (TAATACGACTCACTACGGAAGAA [SEQ ID NO: 11]) sequence in front of psiD controlling expression of all three genes in basic operon configuration | |
| 29 | pETM6-G6-mCherry | #4 containing the mCherry reporter under control of the G6 mutant T7 promoter | (Jones et al., 2015) |
| 30 | pETM6-H9-mCherry | #4 containing the mCherry reporter under control of the H9 mutant T7 promoter | (Jones et al., 2015) |
| 31 | pETM6-H10-mCherry | #4 containing the mCherry reporter under control of the H10 mutant T7 promoter | (Jones et al., 2015) |
| 32 | pETM6-mCherry | #4 containing the mCherry reporter under control of the consensus T7 promoter | (Xu et al., 2012) |
| 33 | pETM6-C4-mCherry | #4 containing the mCherry reporter under control of the C4 mutant T7 promoter | (Jones et al., 2015) |

BIBLIOGRAPHY

Fricke, J., Blei, F., Hoffmeister, D., 2017. Enzymatic synthesis of psilocybin. Angew. Chemie Int. Ed. 56, 12352-12355. (doi.org/10.1002/anie.201705489)

Jones, J. Andrew, Vernacchio, V. R., Lachance, D. M., Lebovich, M., Fu, L., Shirke, A. N., Schultz, V. L., Cress, B., Linhardt, R. J., Koffas, M. A. G., 2015. ePathOptimize: a combinatorial approach for transcriptional balancing of metabolic pathways. Sci. Rep. 5, 11301 (doi.org/10.1038/srep11301)

Xu, P., Vansiri, A., Bhan, N., Koffas, M. A. G., 2012. ePathBrick: A synthetic biology platform for engineering metabolic pathways in *E. coli*. Biol 1, 256-266. (doi.org/10.1021/sb300016b)

TABLE 3

| Sequences | | |
|---|---|---|
| SEQ ID NO: | Description | Sequence |
| 1 | SDM_XbaI-AvrII-FWD Primer 1 | GAATTGTGAGCGGATAACAATTCCCCCCTAGGAATAATTTTG<br>TTTAACTTTAAGAAG<br>(5'-3) |
| 2 | SDM_XbaI-AvrII-REV Primer 2 | CTTCTTAAAGTTAAACAAAATTATTCCTAGGGGGGAATTGTT<br>ATCCGCTCACAATTC<br>(5'-3) |
| 3 | SDM_AvrII-XbaI_FWD Primer 3 | CCGGCCACGATGCGTCCGGCGTAGTCTAGAATCGAGATCGA<br>TCTCGATCCCG<br>(5'-3) |
| 4 | SDM_AvrII-XbaI_REV Primer 4 | CGGGATCGAGATCGATCTCGATTCTAGACTACGCCGGACGC<br>ATCGTGGCCGG<br>(5'-3) |
| 5 | PsiD (Genbank KY984101.1) | ATGCAGGTGATACCCGCGTGCAACTCGGCAGCAATAAGATC<br>ACTATGTCCTACTCCCGAGTCTTTTAGAAACATGGGATGGCT<br>CTCTGTCAGCGATGCGGTCTACAGCGAGTTCATAGGAGAGTT<br>GGCTACCCGCGCTTCCAATCGAAATTACTCCAACGAGTTCGG<br>CCTCATGCAACCTATCCAGGAATTCAAGGCTTTCATTGAAAG<br>CGACCCGGTGGTGCACCAAGAATTTATTGACATGTTCGAGG<br>GCATTCAGGACTCTCCAAGGAATTATCAGGAACTATGTAATA<br>TGTTCAACGATATCTTTCGCAAAGCTCCCGTCTACGGAGACC<br>TTGGCCCTCCCGTTTATATGATTATGGCCAAATTAATGAACA<br>CCCGAGCGGGCTTCTCTGCATTCACGAGACAAAGGTTGAAC<br>CTTCACTTCAAAAAACTTTTCGATACCTGGGGATTGTTCCTG<br>TCTTCGAAAGATTCTCGAAATGTTCTTGTGGCCGACCAGTTC<br>GACGACAGACATTGCGGCTGGTTGAACGAGCGGGCCTTGTC<br>TGCTATGGTTAAACATTACAATGGACGCGCATTTGATGAAGT<br>CTTCCTCTGCGATAAAAATGCCCCATACTACGGCTTCAACTC<br>TTACGACGACTTCTTTAATCGCAGATTTCGAAACCGAGATAT<br>CGACCGACCTGTAGTCGGTGGAGTTAACAACACCACCCTCAT<br>TTCTGCTGCTTGCGAATCACTTTCCTACAACGTCTCTTATGAC<br>GTCCAGTCTCTCGACACTTTAGTTTTCAAAGGAGAGACTTAT |

TABLE 3-continued

| Sequences | | |
|---|---|---|
| SEQ ID NO: | Description | Sequence |
| | | TCGCTTAAGCATTTGCTGAATAATGACCCTTTCACCCCACAA<br>TTCGAGCATGGGAGTATTCTACAAGGATTCTTGAACGTCACC<br>GCTTACCACCGATGGCACGCACCCGTCAATGGGACAATCGT<br>CAAAATCATCAACGTTCCAGGTACCTACTTTGCGCAAGCCCC<br>GAGCACGATTGGCGACCCTATCCCGGATAACGATTACGACC<br>CACCTCCTTACCTTAAGTCTCTTGTCTACTTCTCTAATATTGC<br>CGCAAGGCAAATTATGTTTATTGAAGCCGACAACAAGGAAA<br>TTGGCCTCATTTTCCTTGTGTTCATCGGCATGACCGAAATCTC<br>GACATGTGAAGCCACGGTGTCCGAAGGTCAACACGTCAATC<br>GTGGCGATGACTTGGGAATGTTCCATTTCGGTGGTTCTTCGT<br>TCGCGCTTGGTCTGAGGAAGGATTGCAGGGCAGAGATCGTT<br>GAAAAGTTCACCGAACCCGGAACAGTGATCAGAATCAACGA<br>AGTCGTCGCTGCTCTAAAGGCTTAG |
| 6 | PsiK (Genbank KY984099.1) | ATGGCGTTCGATCTCAAGACTGAAGACGGCCTCATCACATAT<br>CTCACTAAACATCTTTCTTTGGACGTCGACACGAGCGGAGTG<br>AAGCGCCTTAGCGGAGGCTTTGTCAATGTAACCTGGCGCATT<br>AAGCTCAATGCTCCTTATCAAGGTCATACGAGCATCATCCTG<br>AAGCATGCTCAGCCGCACATGTCTACGGATGAGGATTTTAA<br>GATAGGTGTAGAACGTTCGGTTTACGAATACCAGGCTATCA<br>AGCTCATGATGGCCAATCGGGAGGTTCTGGGAGGCGTGGAT<br>GGCATAGTTTCTGTGCCAGAAGGCCTGAACTACGACTTAGA<br>GAATAATGCATTGATCATGCAAGATGTCGGGAAGATGAAGA<br>CCCTTTTAGATTATGTCACCGCCAAACCGCCACTTGCGACGG<br>ATATAGCCCGCCTTGTTGGGACAGAAATTGGGGGGTTCGTTG<br>CCAGACTCCATAACATAGGCCGCGAGAGGCGAGACGATCCT<br>GAGTTCAAATTCTTCTCTGGAAATATTGTCGGAAGGACGACT<br>TCAGACCAGCTGTATCAAACCATCATACCCAACGCAGCGAA<br>ATATGGCGTCGATGACCCCTTGCTGCCTACTGTGGTTAAGGA<br>CCTTGTGGACGATGTCATGCACAGCGAAGAGACCCTTGTCAT<br>GGCGGACCTGTGGAGTGGAAATATTCTTCTCCAGTTGGAGG<br>AGGGAAACCCATCGAAGCTGCAGAAGATATATATCCTGGAT<br>TGGGAACTTTGCAAGTACGGCCCAGCGTCGTTGGACCTGGG<br>CTATTTCTTGGGTGACTGCTATTTGATATCCCGCTTTCAAGAC<br>GAGCAGGTCGGTACGACGATGCGGCAAGCCTACTTGCAAAG<br>CTATGCGCGTACGAGCAAGCATTCGATCAACTACGCCAAAG<br>TCACTGCAGGTATTGCTGCTCATATTGTGATGTGGACCGACT<br>TTATGCAGTGGGGGAGCGAGGAAGAAAGGATAAATTTTGTG<br>AAAAAGGGGGTAGCTGCCTTTCACGACGCCAGGGGCAACAA<br>CGACAATGGGGAAATTACGTCTACCTTACTGAAGGAATCAT<br>CCACTGCGTAA |
| 7 | PsiM (Genbank KY984100.1) | ATGCATATCAGAAATCCTTACCGTACACCAATTGACTATCAA<br>GCACTTTCAGAGGCCTTCCCTCCCCTCAAGCCATTTGTGTCT<br>GTCAATGCAGATGGTACCAGTTCTGTTGACCTCACTATCCCA<br>GAAGCCCAGAGGGCGTTCACGGCCGCTCTTCTTCATCGTGAC<br>TTCGGGCTCACCATGACCATACCAGAAGACCGTCTGTGCCCA<br>ACAGTCCCCAATAGGTTGAACTACGTTCTGTGGATTGAAGAT<br>ATTTTCAACTACACGAACAAAACCCTCGGCCTGTCGGATGAC<br>CGTCCTATTAAAGGCGTTGATATTGGTACAGGAGCCTCCGCA<br>ATTTATCCTATGCTTGCCTGTGCTCGGTTCAAGGCATGGTCT<br>ATGGTTGGAACAGAGGTCGAGAGGAAGTGCATTGACACGGC<br>CCGCCTCAATGTCGTCGCGAACAATCTCCAAGACCGTCTCTC<br>GATATTAGAGACATCCATTGATGGTCCTATTCTCGTCCCCAT<br>TTTCGAGGCGACTGAAGAATACGAATACGAGTTTACTATGTG<br>TAACCCTCCATTCTACGACGGTGCTGCCGATATGCAGACTTC<br>GGATGCTGCCAAAGGATTTGGATTTGGCGTGGGCGCTCCCCA<br>TTCTGGAACAGTCATCGAAATGTCGACTGAGGGAGGTGAAT<br>CGGCTTTCGTCGCTCAGATGGTCCGTGAGAGCTTGAAGCTTC<br>GAACACGATGCAGATGGTACACGAGTAACTTGGGAAAGCTG<br>AAATCCTTGAAAGAAATAGTGGGGCTGCTGAAAGAACTTGA<br>GATAAGCAACTATGCCATTAACGAATACGTTCAGGGGTCCA<br>CACGTCGTTATGCCGTTGCGTGGTCTTTCACTGATATTCAACT<br>GCCTGAGGAGCTTTCTCGTCCCTCTAACCCCGAGCTCAGCTC<br>TCTTTTCTAG |
| 8 | PsiD amino acid sequence | MQVIPACNSAAIRSLCPTPESFRNMGWLSVSDAVYSEFIGELAT<br>RASNRNYSNEFGLMQPIQEFKAFIESDPVVHQEFIDMFEGIQDSP<br>RNYQELCNMFNDIFRKAPVYGDLGPPVYMIMAKLMNTRAGFS<br>AFTRQRLNLHFKKLFDTWGLFLSSKDSRNVLVADQFDDRHCG<br>WLNERALSAMVKHYNGRAFDEVFLCDKNAPYYGFNSYDDFFN<br>RRFRNRDIDRPVVGGVNNTTLISAACESLSYNVSYDVQSLDTLV<br>FKGETYSLKHLLNNDPFTPQFEHGSILQGFLNVTAYHRWHAPV<br>NGTIVKIINVPGTYFAQAPSTIGDPIPDNDYDPPPYLKSLVYFSNI |

TABLE 3-continued

| SEQ ID NO: | Description | Sequence |
|---|---|---|
| | | AARQIMFIEADNKEIGLIFLVFIGMTEISTCEATVSEGQHVNRGD DLGMFHFGGSSFALGLRKDCRAEIVEKFTEPGTVIRINEVVAAL KA |
| 9 | PsiK amino acid sequence | MAFDLKTEDGLITYLTKHLSLDVDTSGVKRLSGGFVNVTWRIK LNAPYQGHTSIILKHAQPHMSTDEDFKIGVERSVYEYQAIKLM MANREVLGGVDGIVSVPEGLNYDLENNALIMQDVGKMKTLLD YVTAKPPLATDIARLVGTEIGGFVARLHNIGRERRDDPEFKFFS GNIVGRTTSDQLYQTIIPNAAKYGVDDPLLPTVVKDLVDDVMH SEETLVMADLWSGNILLQLEEGNPSKLQKIYILDWELCKYGPAS LDLGYFLGDCYLISRFQDEQVGTTMRQAYLQSYARTSKHSINY AKVTAGIAAHIVMWTDFMQWGSEEERINFVKKGVAAFHDARG NNDNGEITSTLLKESSTA |
| 10 | PsiM amino acid sequence | MHIRNPYRTPIDYQALSEAFPPLKPFVSVNADGTSSVDLTIPEAQ RAFTAALLHRDFGLTMTIPEDRLCPTVPNRLNYVLWIEDIFNYT NKTLGLSDDRPIKGVDIGTGASAIYPMLACARFKAWSMVGTEV ERKCIDTARLNVVANNLQDRLSILETSIDGPILVPIFEATEEYEYE FTMCNPPFYDGAADMQTSDAAKGFGFGVGAPHSGTVIEMSTE GGESAFVAQMVRESLKLRTRCRWYTSNLGKLKSLKEIVGLLKE LEISNYAINEYVQGSTRRYAVAWSFTDIQLPEELSRPSNPELSSL F |
| 11 | H10 mutant T7 promoter | TAATACGACTCACTACGGAAGAA |
| 12 | G6 mutant T7 promoter | TAATACGACTCACTATTTCGGAA |
| 13 | H9 mutant T7 promoter | TAATACGACTCACTAATACTGAA |
| 14 | C4 mutant T7 promoter | TAATACGACTCACTATCAAGGAA |
| 15 | consensus T7 promoter | TAATACGACTCACTATAGGGGAA |
| 16 | Lac promoter | TTTACACTTTATGCTTCCGGCTCGTATGTTG |
| 17 | Lac UV5 promoter | TTTACACTTTATGCTTCCGGCTCGTATAATG |
| 18 | tac promoter | TTGACAATTAATCATCGGCTCGTATAATG |
| 19 | trc promoter | TTGACAATTAATCATCCGGCTCGTATAATG |
| 20 | GAP promoter | GCGTAATGCTTAGGCACAGGATTGATTTGTCGCAATGATTGA CACGATTCCGCTTGACGCTGCGTAAGGTTTTTGTAATTTTAC AGGCAACCTTTTATTCA |
| 21 | xylA promoter | TTGAAATAAACATTTATTTTGTATATGATGAGATAAAGTTAG TTTATTGGATAAACAAACTAACTCAATTAAGATAGTTGATGG ATAAACTT |
| 22 | pPsilo16 vector | TAATACGACTCACTACGGAAGAATTGTGAGCGGATAACAAT TCCCCTCTAGAAATAATTTTGTTTAACTTTAAGAAGGAGATA TACATATGGCTAGCATGACTGGTGGACAGCAAATGGGTCGC GGATCCATGCAGGTGATACCCGCGTGCAACTCGGCAGCAAT AAGATCACTATGTCCTACTCCCGAGTCTTTTAGAAACATGGG ATGGCTCTCTGTCAGCGATGCGGTCTACAGCGAGTTCATAGG AGAGTTGGCTACCCGCGCTTCCAATCGAAATTACTCCAACGA GTTCGGCCTCATGCAACCTATCCAGGAATTCAAGGCTTTCAT TGAAAGCGACCCGGTGGTGCACCAAGAATTTATTGACATGTT CGAGGGCATTCAGGACTCTCCAAGGAATTATCAGGAACTAT GTAATATGTTCAACGATATCTTTCGCAAAGCTCCCGTCTACG GAGACCTTGGCCCTCCCGTTTATATGATTATGGCCAAATTAA TGAACACCCGAGCGGGCTTCTCTGCATTCACGAGACAAAGG TTGAACCTTCACTTCAAAAAACTTTTCGATACCTGGGGATTG TTCCTGTCTTCGAAAGATTCTCGAAATGTTCTTGTGGCCGAC CAGTTCGACGACAGACATTGCGGCTGGTTGAACGAGCGGGC CTTGTCTGCTATGGTTAAACATTACAATGGACGCGCATTTGA TGAAGTCTTCCTCTGCGATAAAAATGCCCCATACTACGGCTT CAACTCTTACGACGACTTCTTTAATCGCAGATTTCGAAACCG |

TABLE 3-continued

Sequences

| SEQ ID NO: | Description | Sequence |
|---|---|---|
| | | AGATATCGACCGACCTGTAGTCGGTGGAGTTAACAACACCA<br>CCCTCATTTCTGCTGCTTGCGAATCACTTTCCTACAACGTCTC<br>TTATGACGTCCAGTCTCTCGACACTTTAGTTTTCAAAGGAGA<br>GACTTATTCGCTTAAGCATTTGCTGAATAATGACCCTTTCAC<br>CCCACAATTCGAGCATGGGAGTATTCTACAAGGATTCTTGAA<br>CGTCACCGCTTACCACCGATGGCACGCACCCGTCAATGGGA<br>CAATCGTCAAAATCATCAACGTTCCAGGTACCTACTTTGCGC<br>AAGCCCCGAGCACGATTGGCGACCCTATCCCGGATAACGAT<br>TACGACCCACCTCCTTACCTTAAGTCTCTTGTCTACTTCTCTA<br>ATATTGCCGCAAGGCAAATTATGTTTATTGAAGCCGACAACA<br>AGGAAATTGGCCTCATTTTCCTTGTGTTCATCGGCATGACCG<br>AAATCTCGACATGTGAAGCCACGGTGTCCGAAGGTCAACAC<br>GTCAATCGTGGCGATGACTTGGGAATGTTCCATTTCGGTGGT<br>TCTTCGTTCGCGCTTGGTCTGAGGAAGGATTGCAGGGCAGAG<br>ATCGTTGAAAAGTTCACCGAACCCGGAACAGTGATCAGAAT<br>CAACGAAGTCGTCGCTGCTCTAAAGGCTTAGAAGCTTGCGG<br>CCGCACTCGAGTCTGGTAAAGAAACCGCTGCTGCGAAATTT<br>GAACGCCAGCACATGGACTCGTCTACTAGAAATAATTTTGTT<br>TAACTTTAAGAAGGAGATATACATATGGCTAGCATGACTGG<br>TGGACAGCAAATGGGTCGCGGATCCATGGCGTTCGATCTCA<br>AGACTGAAGACGGCCTCATCACATATCTCACTAAACATCTTT<br>CTTTGGACGTCGACACGAGCGGAGTGAAGCGCCTTAGCGGA<br>GGCTTTGTCAATGTAACCTGGCGCATTAAGCTCAATGCTCCT<br>TATCAAGGTCATACGAGCATCATCCTGAAGCATGCTCAGCCG<br>CACATGTCTACGGATGAGGATTTTAAGATAGGTGTAGAACG<br>TTCGGTTTACGAATACCAGGCTATCAAGCTCATGATGGCCAA<br>TCGGGAGGTTCTGGGAGGCGTGGATGGCATAGTTTCTGTGCC<br>AGAAGGCCTGAACTACGACTTAGAGAATAATGCATTGATCA<br>TGCAAGATGTCGGGAAGATGAAGACCCTTTTAGATTATGTCA<br>CCGCCAAACCGCCACTTGCGACGGATATAGCCCGCCTTGTTG<br>GGACAGAAATTGGGGGGTTCGTTGCCAGACTCCATAACATA<br>GGCCGCGAGAGGCGAGACGATCCTGAGTTCAAATTCTTCTCT<br>GGAAATATTGTCGGAAGGACGACTTCAGACCAGCTGTATCA<br>AACCATCATACCCAACGCAGCGAAATATGGCGTCGATGACC<br>CCTTGCTGCCTACTGTGGTTAAGGACCTTGTGGACGATGTCA<br>TGCACAGCGAAGAGACCCTTGTCATGGCGGACCTGTGGAGT<br>GGAAATATTCTTCTCCAGTTGGAGGAGGGAAACCCATCGAA<br>GCTGCAGAAGATATATATCCTGGATTGGGAACTTTGCAAGTA<br>CGGCCCAGCGTCGTTGGACCTGGGCTATTTCTTGGGTGACTG<br>CTATTTGATATCCCGCTTTCAAGACGAGCAGGTCGGTACGAC<br>GATGCGGCAAGCCTACTTGCAAAGCTATGCGCGTACGAGCA<br>AGCATTCGATCAACTACGCCAAAGTCACTGCAGGTATTGCTG<br>CTCATATTGTGATGTGGACCGACTTTATGCAGTGGGGGAGCG<br>AGGAAGAAAGGATAAATTTTGTGAAAAAGGGGGTAGCTGCC<br>TTTCACGACGCCAGGGGCAACAACGACAATGGGGAAATTAC<br>GTCTACCTTACTGAAGGAATCATCCACTGCGTAAAAGCTTGC<br>GGCCGCACTCGAGTCTGGTAAAGAAACCGCTGCTGCGAAAT<br>TTGAACGCCAGCACATGGACTCGTCTACTAGAAATAATTTTG<br>TTTAACTTTAAGAAGGAGATATACATATGGCTAGCATGACTG<br>GTGGACAGCAAATGGGTCGCGGATCCATGCATATCAGAAAT<br>CCTTACCGTACACCAATTGACTATCAAGCACTTTCAGAGGCC<br>TTCCCTCCCCTCAAGCCATTTGTGTCTGTCAATGCAGATGGT<br>ACCAGTTCTGTTGACCTCACTATCCCAGAAGCCCAGAGGGCG<br>TTCACGGCCGCTCTTCTTCATCGTGACTTCGGGCTCACCATG<br>ACCATACCAGAAGACCGTCTGTGCCCAACAGTCCCCAATAG<br>GTTGAACTACGTTCTGTGGATTGAAGATATTTTCAACTACAC<br>GAACAAAACCCTCGGCCTGTCGGATGACCGTCCTATTAAAG<br>GCGTTGATATTGGTACAGGAGCCTCCGCAATTTATCCTATGC<br>TTGCCTGTGCTCGGTTCAAGGCATGGTCTATGGTTGGAACAG<br>AGGTCGAGAGGAAGTGCATTGACACGGCCCGCCTCAATGTC<br>GTCGCGAACAATCTCCAAGACCGTCTCTCGATATTAGAGACA<br>TCCATTGATGGTCCTATTCTCGTCCCCATTTTCGAGGCGACTG<br>AAGAATACGAATACGAGTTTACTATGTGTAACCCTCCATTCT<br>ACGACGGTGCTGCCGATATGCAGACTTCGGATGCTGCCAAA<br>GGATTTGGATTTGGCGTGGGCGCTCCCCATTCTGGAACAGTC<br>ATCGAAATGTCGACTGAGGGAGGTGAATCGGCTTTCGTCGCT<br>CAGATGGTCCGTGAGAGCTTGAAGCTTCGAACACGATGCAG<br>ATGGTACACGAGTAACTTGGGAAAGCTGAAATCCTTGAAAG<br>AAATAGTGGGGCTGCTGAAAGAACTTGAGATAAGCAACTAT<br>GCCATTAACGAATACGTTCAGGGGTCCACACGTCGTTATGCC<br>GTTGCGTGGTCTTTCACTGATATTCAACTGCCTGAGGAGCTT<br>TCTCGTCCCTCTAACCCCGAGCTCAGCTCTCTTTTCTAGCTCG<br>AGTCTGGTAAAGAAACCGCTGCTGCGAAATTTGAACGCCAG<br>CACATGGACTCGTCTACTAGTCGCAGCTTAATTAACCTAAAC |

TABLE 3-continued

| Sequences | | |
|---|---|---|
| SEQ ID NO: | Description | Sequence |
| | | TGCTGCCACCGCTGAGCAATAACTAGCATAACCCCTTGGGGC<br>CTCTAAACGGGTCTTGAGGGGTTTTTTGCTAGCGAAAGGAGG<br>AGTCGACTATATCCGGATTGGCGAATGGGACGCGCCCTGTA<br>GCGGCGCATTAAGCGCGGCGGGTGTGGTGGTTACGCGCAGC<br>GTGACCGCTACACTTGCCAGCGCCCTAGCGCCCGCTCCTTTC<br>GCTTTCTTCCCTTCCTTTCTCGCCACGTTCGCCGGCTTTCCCC<br>GTCAAGCTCTAAATCGGGGGCTCCCTTTAGGGTTCCGATTTA<br>GTGCTTTACGGCACCTCGACCCCAAAAAACTTGATTAGGGTG<br>ATGGTTCACGTAGTGGGCCATCGCCCTGATAGACGGTTTTTC<br>GCCCTTTGACGTTGGAGTCCACGTTCTTTAATAGTGGACTCT<br>TGTTCCAAACTGGAACAACACTCAACCCTATCTCGGTCTATT<br>CTTTTGATTTATAAGGGATTTTGCCGATTTCGGCCTATTGGTT<br>AAAAAATGAGCTGATTTAACAAAAATTTAACGCGAATTTTA<br>ACAAAATATTAACGTTTACAATTTCTGGCGGCACGATGGCAT<br>GAGATTATCAAAAAGGATCTTCACCTAGATCCTTTTAAATTA<br>AAAATGAAGTTTTAAATCAATCTAAAGTATATATGAGTAAA<br>CTTGGTCTGACAGTTACCAATGCTTAATCAGTGAGGCACCTA<br>TCTCAGCGATCTGTCTATTTCGTTCATCCATAGTTGCCTGACT<br>CCCCGTCGTGTAGATAACTACGATACGGGAGGGCTTACCATC<br>TGGCCCCAGTGCTGCAATGATACCGCGAGACCCACGCTCAC<br>CGGCTCCAGATTTATCAGCAATAAACCAGCCAGCCGGAAGG<br>GCCGAGCGCAGAAGTGGTCCTGCAACTTTATCCGCCTCCATC<br>CAGTCTATTAATTGTTGCCGGGAAGCTAGAGTAAGTAGTTCG<br>CCAGTTAATAGTTTGCGCAACGTTGTTGCCATTGCTACAGGC<br>ATCGTGGTGTCACGCTCGTCGTTTGGTATGGCTTCATTCAGC<br>TCCGGTTCCCAACGATCAAGGCGAGTTACATGATCCCCCATG<br>TTGTGCAAAAAAGCGGTTAGCTCCTTCGGTCCTCCGATCGTT<br>GTCAGAAGTAAGTTGGCCGCAGTGTTATCACTCATGGTTATG<br>GCAGCACTGCATAATTCTCTTACTGTCATGCCATCCGTAAGA<br>TGCTTTTCTGTGACTGGTGAGTACTCAACCAAGTCATTCTGA<br>GAATAGTGTATGCGGCGACCGAGTTGCTCTTGCCCGGCGTCA<br>ATACGGGATAATACCGCGCCACATAGCAGAACTTTAAAAGT<br>GCTCATCATTGGAAAACGTTCTTCGGGGCGAAAACTCTCAAG<br>GATCTTACCGCTGTTGAGATCCAGTTCGATGTAACCCACTCG<br>TGCACCCAACTGATCTTCAGCATCTTTTACTTTCACCAGCGTT<br>TCTGGGTGAGCAAAAACAGGAAGGCAAAATGCCGCAAAAA<br>AGGGAATAAGGGCGACACGGAAATGTTGAATACTCATACTC<br>TTCCTTTTTCAATCATGATTGAAGCATTTATCAGGGTTATTGT<br>CTCATGAGCGGATACATATTTGAATGTATTTAGAAAAATAAA<br>CAAATAGGTCATGACCAAAATCCCTTAACGTGAGTTTTCGTT<br>CCACTGAGCGTCAGACCCCGTAGAAAAGATCAAAGGATCTT<br>CTTGAGATCCTTTTTTTCTGCGCGTAATCTGCTGCTTGCAAAC<br>AAAAAAACCACCGCTACCAGCGGTGGTTTGTTTGCCGGATC<br>AAGAGCTACCAACTCTTTTTCCGAAGGTAACTGGCTTCAGCA<br>GAGCGCAGATACCAAATACTGTCCTTCTAGTGTAGCCGTAGT<br>TAGGCCACCACTTCAAGAACTCTGTAGCACCGCCTACATACC<br>TCGCTCTGCTAATCCTGTTACCAGTGGCTGCTGCCAGTGGCG<br>ATAAGTCGTGTCTTACCGGGTTGGACTCAAGACGATAGTTAC<br>CGGATAAGGCGCAGCGGTCGGGCTGAACGGGGGGTTCGTGC<br>ACACAGCCCAGCTTGGAGCGAACGACCTACACCGAACTGAG<br>ATACCTACAGCGTGAGCTATGAGAAAGCGCCACGCTTCCCG<br>AAGGGAGAAAGGCGGACAGGTATCCGGTAAGCGGCAGGGT<br>CGGAACAGGAGAGCGCACGAGGGAGCTTCCAGGGGGAAAC<br>GCCTGGTATCTTTATAGTCCTGTCGGGTTTCGCCACCTCTGAC<br>TTGAGCGTCGATTTTTGTGATGCTCGTCAGGGGGGCGGAGCC<br>TATGGAAAAACGCCAGCAACGCGGCCTTTTTACGGTTCCTGG<br>CCTTTTGCTGGCCTTTTGCTCACATGTTCTTTCCTGCGTTATC<br>CCCTGATTCTGTGGATAACCGTATTACCGCCTTTGAGTGAGC<br>TGATACCGCTCGCCGCAGCCGAACGACCGAGCGCAGCGAGT<br>CAGTGAGCGAGGAAGCGGAAGAGCGCCTGATGCGGTATTTT<br>CTCCTTACGCATCTGTGCGGTATTTCACACCGCATATATGGT<br>GCACTCTCAGTACAATCTGCTCTGATGCCGCATAGTTAAGCC<br>AGTATACACTCCGCTATCGCTACGTGACTGGGTCATGGCTGC<br>GCCCCGACACCCGCCAACACCCGCTGACGCGCCCTGACGGG<br>CTTGTCTGCTCCCGGCATCCGCTTACAGACAAGCTGTGACCG<br>TCTCCGGGAGCTGCATGTGTCAGAGGTTTTCACCGTCATCAC<br>CGAAACGCGCGAGGCAGCTGCGGTAAAGCTCATCAGCGTGG<br>TCGTGAAGCGATTCACAGATGTCTGCCTGTTCATCCGCGTCC<br>AGCTCGTTGAGTTTCTCCAGAAGCGTTAATGTCTGGCTTCTG<br>ATAAAGCGGGCCATGTTAAGGGCGGTTTTTTCCTGTTTGGTC<br>ACTGATGCCTCCGTGTAAGGGGGATTTCTGTTCATGGGGGTA<br>ATGATACCGATGAAACGAGAGAGGATGCTCACGATACGGGT<br>TACTGATGATGAACATGCCCGGTTACTGGAACGTTGTGAGG<br>GTAAACAACTGGCGGTATGGATGCGGCGGGACCAGAGAAAA |

TABLE 3-continued

| Sequences | | |
|---|---|---|
| SEQ ID NO: | Description | Sequence |
| | | ATCACTCAGGGTCAATGCCAGCGCTTCGTTAATACAGATGTA GGTGTTCCACAGGGTAGCCAGCAGCATCCTGCGATGCAGAT CCGGAACATAATGGTGCAGGGCGCTGACTTCCGCGTTTCCAG ACTTTACGAAACACGGAAACCGAAGACCATTCATGTTGTTGC TCAGGTCGCAGACGTTTTGCAGCAGCAGTCGCTTCACGTTCG CTCGCGTATCGGTGATTCATTCTGCTAACCAGTAAGGCAACC CCGCCAGCCTAGCCGGGTCCTCAACGACAGGAGCACGATCA TGCTAGTCATGCCCCGCGCCCACCGGAAGGAGCTGACTGGG TTGAAGGCTCTCAAGGGCATCGGTCGAGATCCCGGTGCCTA ATGAGTGAGCTAACTTACATTAATTGCGTTGCGCTCACTGCC CGCTTTCCAGTCGGGAAACCTGTCGTGCCAGCTGCATTAATG AATCGGCCAACGCGCGGGGAGAGGCGGTTTGCGTATTGGGC GCCAGGGTGGTTTTTCTTTTCACCAGTGAGACGGGCAACAGC TGATTGCCCTTCACCGCCTGGCCCTGAGAGAGTTGCAGCAAG CGGTCCACGCTGGTTTGCCCCAGCAGGCGAAAATCCTGTTTG ATGGTGGTTAACGGCGGGATATAACATGAGCTGTCTTCGGTA TCGTCGTATCCCACTACCGAGATGTCCGCACCAACGCGCAGC CCGGACTCGGTAATGGCGCGCATTGCGCCCAGCGCCATCTG ATCGTTGGCAACCAGCATCGCAGTGGGAACGATGCCCTCATT CAGCATTTGCATGGTTTGTTGAAAACCGGACATGGCACTCCA GTCGCCTTCCCGTTCCGCTATCGGCTGAATTTGATTGCGAGT GAGATATTTATGCCAGCCAGCCAGACGCAGACGCGCCGAGA CAGAACTTAATGGGCCCGCTAACAGCGCGATTTGCTGGTGA CCCAATGCGACCAGATGCTCCACGCCCAGTCGCGTACCGTCT TCATGGGAGAAAATAATACTGTTGATGGGTGTCTGGTCAGA GACATCAAGAAATAACGCCGGAACATTAGTGCAGGCAGCTT CCACAGCAATGGCATCCTGGTCATCCAGCGGATAGTTAATG ATCAGCCCACTGACGCGTTGCGCGAGAAGATTGTGCACCGC CGCTTTACAGGCTTCGACGCCGCTTCGTTCTACCATCGACAC CACCACGCTGGCACCCAGTTGATCGGCGCGAGATTTAATCGC CGCGACAATTTGCGACGGCGCGTGCAGGGCCAGACTGGAGG TGGCAACGCCAATCAGCAACGACTGTTTGCCCGCCAGTTGTT GTGCCACGCGGTTGGGAATGTAATTCAGCTCCGCCATCGCCG CTTCCACTTTTTCCCGCGTTTTCGCAGAAACGTGGCTGGCCT GGTTCACCACGCGGGAAACGGTCTGATAAGAGACACCGGCA TACTCTGCGACATCGTATAACGTTACTGGTTTCACATTCACC ACCCTGAATTGACTCTCTTCCGGGCGCTATCATGCCATACCG CGAAAGGTTTTGCGCCATTCGATGGTGTCCGGGATCTCGACG CTCTCCCTTATGCGACTCCTGCATTAGGAAGCAGCCCAGTAG TAGGTTGAGGCCGTTGAGCACCGCCGCCGCAAGGAATGGTG CATGCAAGGAGATGGCGCCCAACAGTCCCCCGGCCACGGGG CCTGCCACCATACCCACGCCGAAACAAGCGCTCATGAGCCC GAAGTGGCGAGCCCGATCTTCCCCATCGGTGATGTCGGCGAT ATAGGCGCCAGCAACCGCACCTGTGGCGCCGGTGATGCCGG CCACGATGCGTCCGGCGTAGCCTAGGATCGAGATCGATCTC GATCCCGCGAAAT |
| 23 | pETM6-C4-psiDK | TAATACGACTCACTATCAAGGAATTGTGAGCGGATAACAAT TCCCCTCTAGAAATAATTTTGTTTAACTTTAAGAAGGAGATA TACATATGGCTAGCATGACTGGTGGACAGCAAATGGGTCGC GGATCCATGCAGGTGATACCCGCGTGCAACTCGGCAGCAAT AAGATCACTATGTCCTACTCCCGAGTCTTTTAGAAACATGGG ATGGCTCTCTGTCAGCGATGCGGTCTACAGCGAGTTCATAGG AGAGTTGGCTACCCGCGCTTCCAATCGAAATTACTCCAACGA GTTCGGCCTCATGCAACCTATCCAGGAATTCAAGGCTTTCAT TGAAAGCGACCCGGTGGTGCACCAAGAATTTATTGACATGTT CGAGGGCATTCAGGACTCTCCAAGGAATTATCAGGAACTAT GTAATATGTTCAACGATATCTTTCGCAAAGCTCCCGTCTACG GAGACCTTGGCCCTCCCGTTTATATGATTATGGCCAAATTAA TGAACACCCGAGCGGGCTTCTCTGCATTCACGAGACAAAGG TTGAACCTTCACTTCAAAAAACTTTTCGATACCTGGGGATTG TTCCTGTCTTCGAAAGATTCTCGAAATGTTCTTGTGGCCGAC CAGTTCGACGACAGACATTGCGGCTGGTTGAACGAGCGGGC CTTGTCTGCTATGGTTAAACATTACAATGGACGCGCATTTGA TGAAGTCTTCCTCTGCGATAAAAATGCCCCATACTACGGCTT CAACTCTTACGACGACTTCTTTAATCGCAGATTTCGAAACCG AGATATCGACCGACCTGTAGTCGGTGGAGTTAACAACACCA CCCTCATTTCTGCTGCTTGCGAATCACTTTCCTACAACGTCTC TTATGACGTCCAGTCTCTCGACACTTTAGTTTTCAAAGGAGA GACTTATTCGCTTAAGCATTTGCTGAATAATGACCCTTTCAC CCCACAATTCGAGCATGGGAGTATTCTACAAGGATTCTTGAA CGTCACCGCTTACCACCGATGGCACGCACCCGTCAATGGGA CAATCGTCAAAATCATCAACGTTCCAGGTACCTACTTTGCGC AAGCCCCGAGCACGATTGGCGACCCTATCCCGGATAACGAT |

TABLE 3-continued

Sequences

| SEQ ID NO: | Description | Sequence |
|---|---|---|
| | | TACGACCCACCTCCTTACCTTAAGTCTCTTGTCTACTTCTCTA |
| | | ATATTGCCGCAAGGCAAATTATGTTTATTGAAGCCGACAACA |
| | | AGGAAATTGGCCTCATTTTCCTTGTGTTCATCGGCATGACCG |
| | | AAATCTCGACATGTGAAGCCACGGTGTCCGAAGGTCAACAC |
| | | GTCAATCGTGGCGATGACTTGGGAATGTTCCATTTCGGTGGT |
| | | TCTTCGTTCGCGCTTGGTCTGAGGAAGGATTGCAGGGCAGAG |
| | | ATCGTTGAAAAGTTCACCGAACCCGGAACAGTGATCAGAAT |
| | | CAACGAAGTCGTCGCTGCTCTAAAGGCTTAGAAGCTTGCGG |
| | | CCGCACTCGAGTCTGGTAAAGAAACCGCTGCTGCGAAATTT |
| | | GAACGCCAGCACATGGACTCGTCTACTAGAAATAATTTTGTT |
| | | TAACTTTAAGAAGGAGATATACATATGGCTAGCATGACTGG |
| | | TGGACAGCAAATGGGTCGCGGATCCATGGCGTTCGATCTCA |
| | | AGACTGAAGACGGCCTCATCACATATCTCACTAAACATCTTT |
| | | CTTTGGACGTCGACACGAGCGGAGTGAAGCGCCTTAGCGGA |
| | | GGCTTTGTCAATGTAACCTGGCGCATTAAGCTCAATGCTCCT |
| | | TATCAAGGTCATACGAGCATCATCCTGAAGCATGCTCAGCCG |
| | | CACATGTCTACGGATGAGGATTTTAAGATAGGTGTAGAACG |
| | | TTCGGTTTACGAATACCAGGCTATCAAGCTCATGATGGCCAA |
| | | TCGGGAGGTTCTGGGAGGCGTGGATGGCATAGTTTCTGTGCC |
| | | AGAAGGCCTGAACTACGACTTAGAGAATAATGCATTGATCA |
| | | TGCAAGATGTCGGGAAGATGAAGACCCTTTTAGATTATGTCA |
| | | CCGCCAAACCGCCACTTGCGACGGATATAGCCCGCCTTGTTG |
| | | GGACAGAAATTGGGGGGTTCGTTGCCAGACTCCATAACATA |
| | | GGCCGCGAGAGGCGAGACGATCCTGAGTTCAAATTCTTCTCT |
| | | GGAAATATTGTCGGAAGGACGACTTCAGACCAGCTGTATCA |
| | | AACCATCATACCCAACGCAGCGAAATATGGCGTCGATGACC |
| | | CCTTGCTGCCTACTGTGGTTAAGGACCTTGTGGACGATGTCA |
| | | TGCACAGCGAAGAGACCCTTGTCATGGCGGACCTGTGGAGT |
| | | GGAAATATTCTTCTCCAGTTGGAGGAGGGAAACCCATCGAA |
| | | GCTGCAGAAGATATATATCCTGGATTGGGAACTTTGCAAGTA |
| | | CGGCCCAGCGTCGTTGGACCTGGGCTATTTCTTGGGTGACTG |
| | | CTATTTGATATCCCGCTTTCAAGACGAGCAGGTCGGTACGAC |
| | | GATGCGGCAAGCCTACTTGCAAAGCTATGCGCGTACGAGCA |
| | | AGCATTCGATCAACTACGCCAAAGTCACTGCAGGTATTGCTG |
| | | CTCATATTGTGATGTGGACCGACTTTATGCAGTGGGGGAGCG |
| | | AGGAAGAAAGGATAAATTTTGTGAAAAAGGGGGTAGCTGCC |
| | | TTTCACGACGCCAGGGGCAACAACGACAATGGGGAAATTAC |
| | | GTCTACCTTACTGAAGGAATCATCCACTGCGTAAAAGCTTGC |
| | | GGCCGCACTCGAGTCTGGTAAAGAAACCGCTGCTGCGAAAT |
| | | TTGAACGCCAGCACATGGACTCGTCTACTAGTCGCAGCTTAA |
| | | TTAACCTAAACTGCTGCCACCGCTGAGCAATAACTAGCATAA |
| | | CCCCTTGGGGCCTCTAAACGGGTCTTGAGGGGTTTTTTGCTA |
| | | GCGAAAGGAGGAGTCGACTATATCCGGATTGGCGAATGGGA |
| | | CGCGCCCTGTAGCGGCGCATTAAGCGCGGCGGGTGTGGTGG |
| | | TTACGCGCAGCGTGACCGCTACACTTGCCAGCGCCCTAGCGC |
| | | CCGCTCCTTTCGCTTTCTTCCCTTCCTTTCTCGCCACGTTCGC |
| | | CGGCTTTCCCCGTCAAGCTCTAAATCGGGGGCTCCCTTTAGG |
| | | GTTCCGATTTAGTGCTTTACGGCACCTCGACCCCAAAAAACT |
| | | TGATTAGGGTGATGGTTCACGTAGTGGGCCATCGCCCTGATA |
| | | GACGGTTTTTCGCCCTTTGACGTTGGAGTCCACGTTCTTTAAT |
| | | AGTGGACTCTTGTTCCAAACTGGAACAACACTCAACCCTATC |
| | | TCGGTCTATTCTTTTGATTTATAAGGGATTTTGCCGATTTCGG |
| | | CCTATTGGTTAAAAAATGAGCTGATTTAACAAAAATTTAACG |
| | | CGAATTTTAACAAAATATTAACGTTTACAATTTCTGGCGGCA |
| | | CGATGGCATGAGATTATCAAAAAGGATCTTCACCTAGATCCT |
| | | TTTAAATTAAAAATGAAGTTTTAAATCAATCTAAAGTATATA |
| | | TGAGTAAACTTGGTCTGACAGTTACCAATGCTTAATCAGTGA |
| | | GGCACCTATCTCAGCGATCTGTCTATTTCGTTCATCCATAGTT |
| | | GCCTGACTCCCCGTCGTGTAGATAACTACGATACGGGAGGG |
| | | CTTACCATCTGGCCCCAGTGCTGCAATGATACCGCGAGACCC |
| | | ACGCTCACCGGCTCCAGATTTATCAGCAATAAACCAGCCAG |
| | | CCGGAAGGGCCGAGCGCAGAAGTGGTCCTGCAACTTTATCC |
| | | GCCTCCATCCAGTCTATTAATTGTTGCCGGGAAGCTAGAGTA |
| | | AGTAGTTCGCCAGTTAATAGTTTGCGCAACGTTGTTGCCATT |
| | | GCTACAGGCATCGTGGTGTCACGCTCGTCGTTTGGTATGGCT |
| | | TCATTCAGCTCCGGTTCCCAACGATCAAGGCGAGTTACATGA |
| | | TCCCCCATGTTGTGCAAAAAAGCGGTTAGCTCCTTCGGTCCT |
| | | CCGATCGTTGTCAGAAGTAAGTTGGCCGCAGTGTTATCACTC |
| | | ATGGTTATGGCAGCACTGCATAATTCTCTTACTGTCATGCCA |
| | | TCCGTAAGATGCTTTTCTGTGACTGGTGAGTACTCAACCAAG |
| | | TCATTCTGAGAATAGTGTATGCGGCGACCGAGTTGCTCTTGC |
| | | CCGGCGTCAATACGGGATAATACCGCGCCACATAGCAGAAC |
| | | TTTAAAAGTGCTCATCATTGGAAAACGTTCTTCGGGGCGAAA |
| | | ACTCTCAAGGATCTTACCGCTGTTGAGATCCAGTTCGATGTA |

TABLE 3-continued

Sequences

| SEQ ID NO: | Description | Sequence |
|---|---|---|
| | | ACCCACTCGTGCACCCAACTGATCTTCAGCATCTTTTACTTTC<br>ACCAGCGTTTCTGGGTGAGCAAAAACAGGAAGGCAAAATGC<br>CGCAAAAAAGGGAATAAGGGCGACACGGAAATGTTGAATA<br>CTCATACTCTTCCTTTTTCAATCATGATTGAAGCATTTATCAG<br>GGTTATTGTCTCATGAGCGGATACATATTTGAATGTATTTAG<br>AAAAATAAACAAATAGGTCATGACCAAAATCCCTTAACGTG<br>AGTTTTCGTTCCACTGAGCGTCAGACCCCGTAGAAAAGATCA<br>AAGGATCTTCTTGAGATCCTTTTTTTCTGCGCGTAATCTGCTG<br>CTTGCAAACAAAAAAACCACCGCTACCAGCGGTGGTTTGTTT<br>GCCGGATCAAGAGCTACCAACTCTTTTTCCGAAGGTAACTGG<br>CTTCAGCAGAGCGCAGATACCAAATACTGTCCTTCTAGTGTA<br>GCCGTAGTTAGGCCACCACTTCAAGAACTCTGTAGCACCGCC<br>TACATACCTCGCTCTGCTAATCCTGTTACCAGTGGCTGCTGC<br>CAGTGGCGATAAGTCGTGTCTTACCGGGTTGGACTCAAGAC<br>GATAGTTACCGGATAAGGCGCAGCGGTCGGGCTGAACGGGG<br>GGTTCGTGCACACAGCCCAGCTTGGAGCGAACGACCTACAC<br>CGAACTGAGATACCTACAGCGTGAGCTATGAGAAAGCGCCA<br>CGCTTCCCGAAGGGAGAAAGGCGGACAGGTATCCGGTAAGC<br>GGCAGGGTCGGAACAGGAGAGCGCACGAGGGAGCTTCCAG<br>GGGGAAACGCCTGGTATCTTTATAGTCCTGTCGGGTTTCGCC<br>ACCTCTGACTTGAGCGTCGATTTTTGTGATGCTCGTCAGGGG<br>GGCGGAGCCTATGGAAAAACGCCAGCAACGCGGCCTTTTTA<br>CGGTTCCTGGCCTTTTGCTGGCCTTTTGCTCACATGTTCTTTC<br>CTGCGTTATCCCCTGATTCTGTGGATAACCGTATTACCGCCTT<br>TGAGTGAGCTGATACCGCTCGCCGCAGCCGAACGACCGAGC<br>GCAGCGAGTCAGTGAGCGAGGAAGCGGAAGAGCGCCTGAT<br>GCGGTATTTTCTCCTTACGCATCTGTGCGGTATTTCACACCGC<br>ATATATGGTGCACTCTCAGTACAATCTGCTCTGATGCCGCAT<br>AGTTAAGCCAGTATACACTCCGCTATCGCTACGTGACTGGGT<br>CATGGCTGCGCCCCGACACCCGCCAACACCCGCTGACGCGC<br>CCTGACGGGCTTGTCTGCTCCCGGCATCCGCTTACAGACAAG<br>CTGTGACCGTCTCCGGGAGCTGCATGTGTCAGAGGTTTTCAC<br>CGTCATCACCGAAACGCGCGAGGCAGCTGCGGTAAAGCTCA<br>TCAGCGTGGTCGTGAAGCGATTCACAGATGTCTGCCTGTTCA<br>TCCGCGTCCAGCTCGTTGAGTTTCTCCAGAAGCGTTAATGTC<br>TGGCTTCTGATAAAGCGGGCCATGTTAAGGGCGGTTTTTTCC<br>TGTTTGGTCACTGATGCCTCCGTGTAAGGGGGATTTCTGTTC<br>ATGGGGGTAATGATACCGATGAAACGAGAGAGGATGCTCAC<br>GATACGGGTTACTGATGATGAACATGCCCGGTTACTGGAAC<br>GTTGTGAGGGTAAACAACTGGCGGTATGGATGCGGCGGGAC<br>CAGAGAAAAATCACTCAGGGTCAATGCCAGCGCTTCGTTAA<br>TACAGATGTAGGTGTTCCACAGGGTAGCCAGCAGCATCCTG<br>CGATGCAGATCCGGAACATAATGGTGCAGGGCGCTGACTTC<br>CGCGTTTCCAGACTTTACGAAACACGGAAACCGAAGACCAT<br>TCATGTTGTTGCTCAGGTCGCAGACGTTTTGCAGCAGCAGTC<br>GCTTCACGTTCGCTCGCGTATCGGTGATTCATTCTGCTAACC<br>AGTAAGGCAACCCCGCCAGCCTAGCCGGGTCCTCAACGACA<br>GGAGCACGATCATGCTAGTCATGCCCCGCGCCCACCGGAAG<br>GAGCTGACTGGGTTGAAGGCTCTCAAGGGCATCGGTCGAGA<br>TCCCGGTGCCTAATGAGTGAGCTAACTTACATTAATTGCGTT<br>GCGCTCACTGCCCGCTTTCCAGTCGGGAAACCTGTCGTGCCA<br>GCTGCATTAATGAATCGGCCAACGCGCGGGGAGAGGCGGTT<br>TGCGTATTGGGCGCCAGGGTGGTTTTTCTTTTCACCAGTGAG<br>ACGGGCAACAGCTGATTGCCCTTCACCGCCTGGCCCTGAGA<br>GAGTTGCAGCAAGCGGTCCACGCTGGTTTGCCCCAGCAGGC<br>GAAAATCCTGTTTGATGGTGGTTAACGGCGGGATATAACAT<br>GAGCTGTCTTCGGTATCGTCGTATCCCACTACCGAGATGTCC<br>GCACCAACGCGCAGCCCGGACTCGGTAATGGCGCGCATTGC<br>GCCCAGCGCCATCTGATCGTTGGCAACCAGCATCGCAGTGG<br>GAACGATGCCCTCATTCAGCATTTGCATGGTTTGTTGAAAAC<br>CGGACATGGCACTCCAGTCGCCTTCCCGTTCCGCTATCGGCT<br>GAATTTGATTGCGAGTGAGATATTTATGCCAGCCAGCCAGAC<br>GCAGACGCGCCGAGACAGAACTTAATGGGCCCGCTAACAGC<br>GCGATTTGCTGGTGACCCAATGCGACCAGATGCTCCACGCCC<br>AGTCGCGTACCGTCTTCATGGGAGAAAATAATACTGTTGATG<br>GGTGTCTGGTCAGAGACATCAAGAAATAACGCCGGAACATT<br>AGTGCAGGCAGCTTCCACAGCAATGGCATCCTGGTCATCCA<br>GCGGATAGTTAATGATCAGCCCACTGACGCGTTGCGCGAGA<br>AGATTGTGCACCGCCGCTTTACAGGCTTCGACGCCGCTTCGT<br>TCTACCATCGACACCACCACGCTGGCACCCAGTTGATCGGCG<br>CGAGATTTAATCGCCGCGACAATTTGCGACGGCGCGTGCAG<br>GGCCAGACTGGAGGTGGCAACGCCAATCAGCAACGACTGTT<br>TGCCCGCCAGTTGTTGTGCCACGCGGTTGGGAATGTAATTCA<br>GCTCCGCCATCGCCGCTTCCACTTTTTCCCGCGTTTTCGCAGA |

TABLE 3-continued

| Sequences | | |
|---|---|---|
| SEQ ID NO: | Description | Sequence |
| | | AACGTGGCTGGCCTGGTTCACCACGCGGGAAACGGTCTGAT AAGAGACACCGGCATACTCTGCGACATCGTATAACGTTACT GGTTTCACATTCACCACCCTGAATTGACTCTCTTCCGGGCGC TATCATGCCATACCGCGAAAGGTTTTGCGCCATTCGATGGTG TCCGGGATCTCGACGCTCTCCCTTATGCGACTCCTGCATTAG GAAGCAGCCCAGTAGTAGGTTGAGGCCGTTGAGCACCGCCG CCGCAAGGAATGGTGCATGCAAGGAGATGGCGCCCAACAGT CCCCCGGCCACGGGGCCTGCCACCATACCCACGCCGAAACA AGCGCTCATGAGCCCGAAGTGGCGAGCCCGATCTTCCCCATC GGTGATGTCGGCGATATAGGCGCCAGCAACCGCACCTGTGG CGCCGGTGATGCCGGCCACGATGCGTCCGGCGTAGCCTAGG ATCGAGATCGATCTCGATCCCGCGAAAT |

All publications and patents referred to herein are incorporated by reference. Various modifications and variations of the described subject matter will be apparent to those skilled in the art without departing from the scope and spirit of the invention. Although the invention has been described in connection with specific embodiments, it should be understood that the invention as claimed should not be unduly limited to these embodiments. Indeed, various modifications for carrying out the invention are obvious to those skilled in the art and are intended to be within the scope of the following claims.

What is claimed is:

1. A recombinant prokaryotic cell comprising one or more expression vectors and a promoter, wherein each expression vector comprises a psilocybin production gene selected from the group consisting of psiD, psiK and psiM and combinations thereof, and wherein the promoter is selected from the group consisting of G6 mutant T7, H9 mutant T7, H10 mutant T7, C4 mutant T7, trc, GAP, and xylA promoter.

2. The recombinant prokaryotic cell of claim 1, wherein the psiD comprises the amino acid sequence of SEQ ID NO: 8 or a sequence having at least 60%, at least 70%, at least 80%, at least 90%, at least 95%, at least 96%, at least 97%, at least 98%, or at least 99% sequence identity thereto.

3. The recombinant prokaryotic cell of claim 1, wherein the psiK comprises the amino acid sequence of SEQ ID NO: 9 or a sequence having at least 60%, at least 70%, at least 80%, at least 90%, at least 95%, at least 96%, at least 97%, at least 98%, or at least 99% sequence identity thereto.

4. The recombinant prokaryotic cell of claim 1, wherein the psiM comprises the amino acid sequence of SEQ ID NO:

10 or a sequence having at least 60%, at least 70%, at least 80%, at least 90%, at least 95%, at least 96%, at least 97%, at least 98%, or at least 99% sequence identity thereto.

5. The recombinant prokaryotic cell of claim 1, wherein the prokaryotic cell is selected from the group consisting of *Escherichia coli, Corynebacterium glutamicum, Vibrio natriegens, Bacillus subtilis, Bacillus megaterium, Escherichia coli* Nissle 1917, *Clostridium acetobutlyicum, Streptomyces coelicolor, Lactococcus lactis, Pseudomonas putida, Streptomyces clavuligerus*, and *Streptomyces venezuelae.*

6. The recombinant prokaryotic cell of claim 1, wherein the expression vector comprises a psiD gene, a psiK gene and a psiM gene, wherein:

all genes are under control of a single promoter in operon configuration;

each gene is under control of a separate promoter in pseudooperon configuration; or each gene is in monocistronic configuration wherein each gene has a promoter and a terminator.

7. The recombinant prokaryotic cell of claim 1, wherein the promoter is selected from the group consisting of G6 mutant T7, H9 mutant T7, H10 mutant T7, and C4 mutant T7.

8. An expression vector comprising a psiD gene, a psiK gene and a psiM gene, wherein:

all genes are under control of a single promoter in operon configuration;

each gene is under control of a separate promoter in pseudooperon configuration; or each gene is in monocistronic configuration wherein each gene has a promoter and a terminator; wherein the promoter is selected from the group consisting of G6 mutant T7, H9 mutant T7, H10 mutant T7, C4 mutant T7, trc, GAP, and xylA promoter.

9. The expression vector of claim 8, wherein the promoter is selected from the group consisting of H10 mutant T7and C4 mutant T7.

10. A recombinant prokaryotic cell comprising one or more expression vectors and a promoter, wherein each expression vector comprises a psilocybin production gene selected from the group consisting of psiD, psiK and combinations thereof; wherein the promoter is selected from the group consisting of G6 mutant T7, H9 mutant T7, H10 mutant T7, C4 mutant T7, trc, GAP, and xylA promoter;

wherein the recombinant prokaryotic cell does not comprise psiM.

11. The recombinant prokaryotic cell of claim 10, wherein the psiD comprises the amino acid sequence of SEQ ID NO: 8 or a sequence having at least 60%, at least 70%, at least 80%, at least 90%, at least 95%, at least 96%, at least 97%, at least 98%, or at least 99% sequence identity thereto.

12. The recombinant prokaryotic cell of claim 10, wherein the psiK comprises the amino acid sequence of SEQ ID NO: 9 or a sequence having at least 60%, at least 70%, at least 80%, at least 90%, at least 95%, at least 96%, at least 97%, at least 98%, or at least 99% sequence identity thereto.

13. The recombinant prokaryotic cell of claim 10, wherein the prokaryotic cell is selected from the group consisting of *Escherichia coli, Corynebacterium glutamicum, Vibrio natriegens, Bacillus subtilis, Bacillus megaterium, Escherichia coli* Nissle 1917, *Clostridium* acetobutlyicum, *Streptomyces coelicolor, Lactococcus lactis, Pseudomonas putida, Streptomyces clavuligerus*, and *Streptomyces venezuelae.*

14. The recombinant prokaryotic cell of claim 10, wherein the expression vector comprises a psilocybin production gene selected from the group consisting of psiD, psiK and combinations thereof, wherein:

all genes are under control of a single promoter in operon configuration;

each gene is under control of a separate promoter in pseudooperon configuration; or each gene is in monocistronic configuration wherein each gene has a promoter and a terminator.

15. The recombinant prokaryotic cell of claim 10, wherein the promoter is selected from the group consisting of G6 mutant T7, H9 mutant T7, H10 mutant T7, and C4 mutant T7.

16. An expression vector comprising a psilocybin production gene selected from the group consisting of psiD, psiK and combinations thereof, wherein:

all genes are under control of a single promoter in operon configuration;

each gene is under control of a separate promoter in pseudooperon configuration; or each gene is in monocistronic configuration wherein each gene has a promoter and a terminator;

wherein the promoter is selected from the group consisting of G6 mutant T7, H9 mutant T7, H10 mutant T7, C4 mutant T7, trc, GAP, and xylA promoter;

wherein the expression vector does not comprise psiM.

17. The expression vector of claim 16, wherein the promoter is selected from the group consisting of G6 mutant T7, H9 mutant T7, H10 mutant T7, and C4 mutant T7.

* * * * *

SEQUENCE LISTING

<160> NUMBER OF SEQ ID NOS: 23

<210> SEQ ID NO 1
<211> LENGTH: 57
<212> TYPE: DNA
<213> ORGANISM: Artificial Sequence
<220> FEATURE:
<223> OTHER INFORMATION: SDM_XbaI-AvrII-FWD

<400> SEQUENCE: 1
gaattgtgag cggataacaa ttcccccta ggaataattt tgtttaactt taagaag 57

<210> SEQ ID NO 2
<211> LENGTH: 57
<212> TYPE: DNA
<213> ORGANISM: Artificial Sequence
<220> FEATURE:
<223> OTHER INFORMATION: SDM_XbaI-AvrII-REV

<400> SEQUENCE: 2
cttcttaaag ttaaacaaaa ttattcctag gggggaattg ttatccgctc acaattc 57

<210> SEQ ID NO 3
<211> LENGTH: 52
<212> TYPE: DNA
<213> ORGANISM: Artificial Sequence
<220> FEATURE:
<223> OTHER INFORMATION: SDM_AvrII-XbaI_FWD

<400> SEQUENCE: 3
ccggccacga tgcgtccggc gtagtctaga atcgagatcg atctcgatcc cg 52

<210> SEQ ID NO 4
<211> LENGTH: 52
<212> TYPE: DNA
<213> ORGANISM: Artificial Sequence
<220> FEATURE:
<223> OTHER INFORMATION: SDM_AvrII-XbaI_REV

<400> SEQUENCE: 4
cgggatcgag atcgatctcg attctagact acgccggacg catcgtggcc gg 52

<210> SEQ ID NO 5
<211> LENGTH: 1320
<212> TYPE: DNA
<213> ORGANISM: Psilocybe cubensis

<400> SEQUENCE: 5
atgcaggtga tacccgcgtg caactcggca gcaataagat cactatgtcc tactcccgag 60
tcttttagaa acatgggatg gctctctgtc agcgatgcgg tctacagcga gttcatagga 120
gagttggcta cccgcgcttc caatcgaaat tactccaacg agttcggcct catgcaacct 180
atccaggaat tcaaggcttt cattgaaagc gacccggtgg tgcaccaaga atttattgac 240
atgttcgagg gcattcagga ctctccaagg aattatcagg aactatgtaa tatgttcaac 300
gatatctttc gcaaagctcc cgtctacgga gaccttggcc ctcccgttta tatgattatg 360
gccaaattaa tgaacacccg agcgggcttc tctgcattca cgagacaaag gttgaacctt 420
cacttcaaaa aacttttcga tacctgggga ttgttcctgt cttcgaaaga ttctcgaaat 480
gttcttgtgg ccgaccagtt cgacgacaga cattgcggct ggttgaacga gcgggccttg 540
tctgctatgg ttaaacatta caatggacgc gcatttgatg aagtcttcct ctgcgataaa 600
aatgccccat actacggctt caactcttac gacgacttct ttaatcgcag atttcgaaac 660
cgagatatcg accgacctgt agtcggtgga gttaacaaca ccaccctcat ttctgctgct 720
tgcgaatcac tttcctacaa cgtctcttat gacgtccagt ctctcgacac tttagttttc 780
aaaggagaga cttattcgct taagcatttg ctgaataatg accctttcac cccacaattc 840
gagcatggga gtattctaca aggattcttg aacgtcaccg cttaccaccg atggcacgca 900
cccgtcaatg ggacaatcgt caaaatcatc aacgttccag gtacctactt tgcgcaagcc 960
ccgagcacga ttggcgaccc tatcccggat aacgattacg acccacctcc ttaccttaag 1020
tctcttgtct acttctctaa tattgccgca aggcaaatta tgtttattga agccgacaac 1080
aaggaaattg gcctcatttt ccttgtgttc atcggcatga ccgaaatctc gacatgtgaa 1140
gccacggtgt ccgaaggtca acacgtcaat cgtggcgatg acttgggaat gttccatttc 1200
ggtggttctt cgttcgcgct tggtctgagg aaggattgca gggcagagat cgttgaaaag 1260
ttcaccgaac ccggaacagt gatcagaatc aacgaagtcg tcgctgctct aaaggcttag 1320

<210> SEQ ID NO 6
<211> LENGTH: 1089
<212> TYPE: DNA
<213> ORGANISM: Psilocybe cubensis

<400> SEQUENCE: 6
atggcgttcg atctcaagac tgaagacggc ctcatcacat atctcactaa acatctttct 60
ttggacgtcg acacgagcgg agtgaagcgc cttagcggag gctttgtcaa tgtaacctgg 120
cgcattaagc tcaatgctcc ttatcaaggt catacgagca tcatcctgaa gcatgctcag 180
ccgcacatgt ctacggatga ggattttaag ataggtgtag aacgttcggt ttacgaatac 240
caggctatca agctcatgat ggccaatcgg gaggttctgg gaggcgtgga tggcatagtt 300
tctgtgccag aaggcctgaa ctacgactta gagaataatg cattgatcat gcaagatgtc 360
gggaagatga agacccttt agattatgtc accgccaaac cgccacttgc gacggatata 420
gcccgccttg ttgggacaga aattgggggg ttcgttgcca gactccataa cataggccgc 480
gagaggcgag acgatcctga gttcaaattc ttctctggaa atattgtcgg aaggacgact 540
tcagaccagc tgtatcaaac catcataccc aacgcagcga aatatggcgt cgatgacccc 600
ttgctgccta ctgtggttaa ggaccttgtg gacgatgtca tgcacagcga agagaccctt 660
gtcatggcgg acctgtggag tggaaatatt cttctccagt tggaggaggg aaacccatcg 720
aagctgcaga agatatatat cctggattgg gaactttgca agtacggccc agcgtcgttg 780
gacctgggct atttcttggg tgactgctat ttgatatccc gctttcaaga cgagcaggtc 840
ggtacgacga tgcggcaagc ctacttgcaa agctatgcgc gtacgagcaa gcattcgatc 900
aactacgcca aagtcactgc aggtattgct gctcatattg tgatgtggac cgactttatg 960 cagtgggggga gcgaggaaga aaggataaat tttgtgaaaa agggggtagc tgcctttcac 1020
gacgccaggg gcaacaacga caatggggaa attacgtcta ccttactgaa ggaatcatcc 1080
actgcgtaa 1089

<210> SEQ ID NO 7
<211> LENGTH: 930
<212> TYPE: DNA
<213> ORGANISM: Psilocybe cubensis

<400> SEQUENCE: 7
atgcatatca gaaatcctta ccgtacacca attgactatc aagcactttc agaggccttc 60
cctcccctca agccatttgt gtctgtcaat gcagatggta ccagttctgt tgacctcact 120
atcccagaag cccagagggc gttcacggcc gctcttcttc atcgtgactt cgggctcacc 180
atgaccatac cagaagaccg tctgtgccca acagtcccca ataggttgaa ctacgttctg 240
tggattgaag atattttcaa ctacacgaac aaaaccctcg gcctgtcgga tgaccgtcct 300
attaaaggcg ttgatattgg tacaggagcc tccgcaattt atcctatgct tgcctgtgct 360
cggttcaagg catggtctat ggttggaaca gaggtcgaga ggaagtgcat tgacacggcc 420
cgcctcaatg tcgtcgcgaa caatctccaa gaccgtctct cgatattaga gacatccatt 480
gatggtccta ttctcgtccc cattttcgag gcgactgaag aatacgaata cgagtttact 540
atgtgtaacc ctccattcta cgacggtgct gccgatatgc agacttcgga tgctgccaaa 600
ggatttggat ttggcgtggg cgctccccat tctggaacag tcatcgaaat gtcgactgag 660
ggaggtgaat cggctttcgt cgctcagatg gtccgtgaga gcttgaagct tcgaacacga 720
tgcagatggt acacgagtaa cttgggaaag ctgaaatcct tgaaagaaat agtggggctg 780
ctgaaagaac ttgagataag caactatgcc attaacgaat acgttcaggg gtccacacgt 840
cgttatgccg ttgcgtggtc tttcactgat attcaactgc ctgaggagct ttctcgtccc 900
tctaaccccg agctcagctc tcttttctag 930

<210> SEQ ID NO 8
<211> LENGTH: 439
<212> TYPE: PRT
<213> ORGANISM: Psilocybe cubensis

<400> SEQUENCE: 8

Met Gln Val Ile Pro Ala Cys Asn Ser Ala Ala Ile Arg Ser Leu Cys
1               5                   10                  15

Pro Thr Pro Glu Ser Phe Arg Asn Met Gly Trp Leu Ser Val Ser Asp
            20                  25                  30

```
Ala Val Tyr Ser Glu Phe Ile Gly Glu Leu Ala Thr Arg Ala Ser Asn
        35                  40                  45

Arg Asn Tyr Ser Asn Glu Phe Gly Leu Met Gln Pro Ile Gln Glu Phe
    50                  55                  60

Lys Ala Phe Ile Glu Ser Asp Pro Val Val His Gln Glu Phe Ile Asp
65                  70                  75                  80

Met Phe Glu Gly Ile Gln Asp Ser Pro Arg Asn Tyr Gln Glu Leu Cys
                85                  90                  95

Asn Met Phe Asn Asp Ile Phe Arg Lys Ala Pro Val Tyr Gly Asp Leu
            100                 105                 110

Gly Pro Pro Val Tyr Met Ile Met Ala Lys Leu Met Asn Thr Arg Ala
        115                 120                 125

Gly Phe Ser Ala Phe Thr Arg Gln Arg Leu Asn Leu His Phe Lys Lys
    130                 135                 140

Leu Phe Asp Thr Trp Gly Leu Phe Leu Ser Ser Lys Asp Ser Arg Asn
145                 150                 155                 160

Val Leu Val Ala Asp Gln Phe Asp Asp Arg His Cys Gly Trp Leu Asn
                165                 170                 175

Glu Arg Ala Leu Ser Ala Met Val Lys His Tyr Asn Gly Arg Ala Phe
            180                 185                 190

Asp Glu Val Phe Leu Cys Asp Lys Asn Ala Pro Tyr Tyr Gly Phe Asn
        195                 200                 205

Ser Tyr Asp Asp Phe Phe Asn Arg Arg Phe Arg Asn Arg Asp Ile Asp
    210                 215                 220

Arg Pro Val Val Gly Gly Val Asn Asn Thr Thr Leu Ile Ser Ala Ala
225                 230                 235                 240

Cys Glu Ser Leu Ser Tyr Asn Val Ser Tyr Asp Val Gln Ser Leu Asp
                245                 250                 255

Thr Leu Val Phe Lys Gly Glu Thr Tyr Ser Leu Lys His Leu Leu Asn
            260                 265                 270

Asn Asp Pro Phe Thr Pro Gln Phe Glu His Gly Ser Ile Leu Gln Gly
        275                 280                 285

Phe Leu Asn Val Thr Ala Tyr His Arg Trp His Ala Pro Val Asn Gly
    290                 295                 300

Thr Ile Val Lys Ile Ile Asn Val Pro Gly Thr Tyr Phe Ala Gln Ala
305                 310                 315                 320

Pro Ser Thr Ile Gly Asp Pro Ile Pro Asp Asn Asp Tyr Asp Pro Pro
                325                 330                 335

Pro Tyr Leu Lys Ser Leu Val Tyr Phe Ser Asn Ile Ala Ala Arg Gln
            340                 345                 350

Ile Met Phe Ile Glu Ala Asp Asn Lys Glu Ile Gly Leu Ile Phe Leu
        355                 360                 365

Val Phe Ile Gly Met Thr Glu Ile Ser Thr Cys Glu Ala Thr Val Ser
    370                 375                 380

Glu Gly Gln His Val Asn Arg Gly Asp Asp Leu Gly Met Phe His Phe
385                 390                 395                 400

Gly Gly Ser Ser Phe Ala Leu Gly Leu Arg Lys Asp Cys Arg Ala Glu
                405                 410                 415

Ile Val Glu Lys Phe Thr Glu Pro Gly Thr Val Ile Arg Ile Asn Glu
            420                 425                 430

Val Val Ala Ala Leu Lys Ala
        435
```

<210> SEQ ID NO 9
<211> LENGTH: 362
<212> TYPE: PRT
<213> ORGANISM: Psilocybe cubensis

<400> SEQUENCE: 9

```
Met Ala Phe Asp Leu Lys Thr Glu Asp Gly Leu Ile Thr Tyr Leu Thr
1               5                   10                  15

Lys His Leu Ser Leu Asp Val Asp Thr Ser Gly Val Lys Arg Leu Ser
            20                  25                  30

Gly Gly Phe Val Asn Val Thr Trp Arg Ile Lys Leu Asn Ala Pro Tyr
        35                  40                  45

Gln Gly His Thr Ser Ile Ile Leu Lys His Ala Gln Pro His Met Ser
    50                  55                  60

Thr Asp Glu Asp Phe Lys Ile Gly Val Glu Arg Ser Val Tyr Glu Tyr
65                  70                  75                  80

Gln Ala Ile Lys Leu Met Met Ala Asn Arg Glu Val Leu Gly Gly Val
                85                  90                  95

Asp Gly Ile Val Ser Val Pro Glu Gly Leu Asn Tyr Asp Leu Glu Asn
            100                 105                 110

Asn Ala Leu Ile Met Gln Asp Val Gly Lys Met Lys Thr Leu Leu Asp
        115                 120                 125

Tyr Val Thr Ala Lys Pro Pro Leu Ala Thr Asp Ile Ala Arg Leu Val
    130                 135                 140

Gly Thr Glu Ile Gly Gly Phe Val Ala Arg Leu His Asn Ile Gly Arg
145                 150                 155                 160

Glu Arg Arg Asp Asp Pro Glu Phe Lys Phe Phe Ser Gly Asn Ile Val
                165                 170                 175

Gly Arg Thr Thr Ser Asp Gln Leu Tyr Gln Thr Ile Ile Pro Asn Ala
            180                 185                 190

Ala Lys Tyr Gly Val Asp Asp Pro Leu Leu Pro Thr Val Val Lys Asp
        195                 200                 205

Leu Val Asp Asp Val Met His Ser Glu Glu Thr Leu Val Met Ala Asp
    210                 215                 220

Leu Trp Ser Gly Asn Ile Leu Leu Gln Leu Glu Glu Gly Asn Pro Ser
225                 230                 235                 240

Lys Leu Gln Lys Ile Tyr Ile Leu Asp Trp Glu Leu Cys Lys Tyr Gly
                245                 250                 255

Pro Ala Ser Leu Asp Leu Gly Tyr Phe Leu Gly Asp Cys Tyr Leu Ile
            260                 265                 270

Ser Arg Phe Gln Asp Glu Gln Val Gly Thr Thr Met Arg Gln Ala Tyr
        275                 280                 285

Leu Gln Ser Tyr Ala Arg Thr Ser Lys His Ser Ile Asn Tyr Ala Lys
    290                 295                 300

Val Thr Ala Gly Ile Ala Ala His Ile Val Met Trp Thr Asp Phe Met
305                 310                 315                 320

Gln Trp Gly Ser Glu Glu Glu Arg Ile Asn Phe Val Lys Lys Gly Val
                325                 330                 335

Ala Ala Phe His Asp Ala Arg Gly Asn Asn Asp Asn Gly Glu Ile Thr
            340                 345                 350

Ser Thr Leu Leu Lys Glu Ser Ser Thr Ala
        355                 360
```

<210> SEQ ID NO 10

<211> LENGTH: 309
<212> TYPE: PRT
<213> ORGANISM: Psilocybe cubensis

<400> SEQUENCE: 10

Met His Ile Arg Asn Pro Tyr Arg Thr Pro Ile Asp Tyr Gln Ala Leu
1 5 10 15

Ser Glu Ala Phe Pro Pro Leu Lys Pro Phe Val Ser Val Asn Ala Asp
20 25 30

Gly Thr Ser Ser Val Asp Leu Thr Ile Pro Glu Ala Gln Arg Ala Phe
35 40 45

Thr Ala Ala Leu Leu His Arg Asp Phe Gly Leu Thr Met Thr Ile Pro
50 55 60

Glu Asp Arg Leu Cys Pro Thr Val Pro Asn Arg Leu Asn Tyr Val Leu
65 70 75 80

Trp Ile Glu Asp Ile Phe Asn Tyr Thr Asn Lys Thr Leu Gly Leu Ser
85 90 95

Asp Asp Arg Pro Ile Lys Gly Val Asp Ile Gly Thr Gly Ala Ser Ala
100 105 110

Ile Tyr Pro Met Leu Ala Cys Ala Arg Phe Lys Ala Trp Ser Met Val
115 120 125

Gly Thr Glu Val Glu Arg Lys Cys Ile Asp Thr Ala Arg Leu Asn Val
130 135 140

Val Ala Asn Asn Leu Gln Asp Arg Leu Ser Ile Leu Glu Thr Ser Ile
145 150 155 160

Asp Gly Pro Ile Leu Val Pro Ile Phe Glu Ala Thr Glu Glu Tyr Glu
165 170 175

Tyr Glu Phe Thr Met Cys Asn Pro Pro Phe Tyr Asp Gly Ala Ala Asp
180 185 190

Met Gln Thr Ser Asp Ala Ala Lys Gly Phe Gly Phe Gly Val Gly Ala
195 200 205

Pro His Ser Gly Thr Val Ile Glu Met Ser Thr Glu Gly Gly Glu Ser
210 215 220

Ala Phe Val Ala Gln Met Val Arg Glu Ser Leu Lys Leu Arg Thr Arg
225 230 235 240

Cys Arg Trp Tyr Thr Ser Asn Leu Gly Lys Leu Lys Ser Leu Lys Glu
245 250 255

Ile Val Gly Leu Leu Lys Glu Leu Glu Ile Ser Asn Tyr Ala Ile Asn
260 265 270

Glu Tyr Val Gln Gly Ser Thr Arg Arg Tyr Ala Val Ala Trp Ser Phe
275 280 285

Thr Asp Ile Gln Leu Pro Glu Glu Leu Ser Arg Pro Ser Asn Pro Glu
290 295 300

Leu Ser Ser Leu Phe
305

<210> SEQ ID NO 11
<211> LENGTH: 23
<212> TYPE: DNA
<213> ORGANISM: Artificial Sequence
<220> FEATURE:
<223> OTHER INFORMATION: H10 mutant T7 promoter

<400> SEQUENCE: 11
taatacgact cactacggaa gaa 23

<210> SEQ ID NO 12
<211> LENGTH: 23
<212> TYPE: DNA
<213> ORGANISM: Artificial Sequence
<220> FEATURE:
<223> OTHER INFORMATION: G6 mutant T7 promoter

<400> SEQUENCE: 12
taatacgact cactatttcg gaa 23

<210> SEQ ID NO 13
<211> LENGTH: 23
<212> TYPE: DNA
<213> ORGANISM: Artificial Sequence
<220> FEATURE:
<223> OTHER INFORMATION: H9 mutant T7 promoter

<400> SEQUENCE: 13
taatacgact cactaatact gaa 23

<210> SEQ ID NO 14
<211> LENGTH: 23
<212> TYPE: DNA
<213> ORGANISM: Artificial Sequence
<220> FEATURE:
<223> OTHER INFORMATION: C4 mutant T7 promoter

<400> SEQUENCE: 14
taatacgact cactatcaag gaa 23

<210> SEQ ID NO 15
<211> LENGTH: 23
<212> TYPE: DNA
<213> ORGANISM: Artificial Sequence
<220> FEATURE:
<223> OTHER INFORMATION: consensus T7 promoter

<400> SEQUENCE: 15
taatacgact cactataggg gaa 23

<210> SEQ ID NO 16
<211> LENGTH: 31
<212> TYPE: DNA
<213> ORGANISM: Artificial Sequence
<220> FEATURE:
<223> OTHER INFORMATION: Lac promoter

<400> SEQUENCE: 16
tttacacttt atgcttccgg ctcgtatgtt g 31

<210> SEQ ID NO 17
<211> LENGTH: 31
<212> TYPE: DNA
<213> ORGANISM: Artificial Sequence
<220> FEATURE:
<223> OTHER INFORMATION: Lac UV5 promoter

<400> SEQUENCE: 17
tttacacttt atgcttccgg ctcgtataat g 31

<210> SEQ ID NO 18
<211> LENGTH: 29
<212> TYPE: DNA
<213> ORGANISM: Artificial Sequence
<220> FEATURE:
<223> OTHER INFORMATION: tac promoter

<400> SEQUENCE: 18
ttgacaatta atcatcggct cgtataatg 29

<210> SEQ ID NO 19
<211> LENGTH: 30
<212> TYPE: DNA
<213> ORGANISM: Artificial Sequence
<220> FEATURE:
<223> OTHER INFORMATION: trc promoter

<400> SEQUENCE: 19
ttgacaatta atcatccggc tcgtataatg 30

<210> SEQ ID NO 20
<211> LENGTH: 101
<212> TYPE: DNA
<213> ORGANISM: Artificial Sequence
<220> FEATURE:
<223> OTHER INFORMATION: GAP promoter

<400> SEQUENCE: 20
gcgtaatgct taggcacagg attgatttgt cgcaatgatt gacacgattc cgcttgacgc 60
tgcgtaaggt ttttgtaatt ttacaggcaa ccttttattc a 101

<210> SEQ ID NO 21
<211> LENGTH: 92
<212> TYPE: DNA
<213> ORGANISM: Artificial Sequence
<220> FEATURE:
<223> OTHER INFORMATION: xylA promoter

<400> SEQUENCE: 21
ttgaaataaa catttatttt gtatatgatg agataaagtt agtttattgg ataaacaaac 60
taactcaatt aagatagttg atggataaac tt 92

<210> SEQ ID NO 22
<211> LENGTH: 8848
<212> TYPE: DNA
<213> ORGANISM: Artificial Sequence
<220> FEATURE:
<223> OTHER INFORMATION: pPsilo16 vector

<400> SEQUENCE: 22
taatacgact cactacggaa gaattgtgag cggataacaa ttcccctcta gaaataattt 60
tgtttaactt taagaaggag atatacatat ggctagcatg actggtggac agcaaatggg 120
tcgcggatcc atgcaggtga tacccgcgtg caactcggca gcaataagat cactatgtcc 180
tactcccgag tcttttagaa acatgggatg gctctctgtc agcgatgcgg tctacagcga 240
gttcatagga gagttggcta cccgcgcttc caatcgaaat tactccaacg agttcggcct 300
catgcaacct atccaggaat tcaaggcttt cattgaaagc gacccggtgg tgcaccaaga 360
atttattgac atgttcgagg gcattcagga ctctccaagg aattatcagg aactatgtaa 420
tatgttcaac gatatctttc gcaaagctcc cgtctacgga gaccttggcc ctcccgttta 480
tatgattatg gccaaattaa tgaacacccg agcgggcttc tctgcattca cgagacaaag 540
gttgaacctt cacttcaaaa aactttttcga tacctgggga ttgttcctgt cttcgaaaga 600
ttctcgaaat gttcttgtgg ccgaccagtt cgacgacaga cattgcggct ggttgaacga 660
gcgggccttg tctgctatgg ttaaacatta caatggacgc gcatttgatg aagtcttcct 720
ctgcgataaa aatgccccat actacggctt caactcttac gacgacttct ttaatcgcag 780

```
atttcgaaac cgagatatcg accgacctgt agtcggtgga gttaacaaca ccaccctcat    840
ttctgctgct tgcgaatcac tttcctacaa cgtctcttat gacgtccagt ctctcgacac    900
tttagttttc aaaggagaga cttattcgct taagcatttg ctgaataatg accctttcac    960
cccacaattc gagcatggga gtattctaca aggattcttg aacgtcaccg cttaccaccg   1020
atggcacgca cccgtcaatg ggacaatcgt caaaatcatc aacgttccag gtacctactt   1080
tgcgcaagcc ccgagcacga ttggcgaccc tatcccggat aacgattacg acccacctcc   1140
ttaccttaag tctcttgtct acttctctaa tattgccgca aggcaaatta tgtttattga   1200
agccgacaac aaggaaattg gcctcatttt ccttgtgttc atcggcatga ccgaaatctc   1260
gacatgtgaa gccacggtgt ccgaaggtca acacgtcaat cgtggcgatg acttgggaat   1320
gttccatttc ggtggttctt cgttcgcgct tggtctgagg aaggattgca gggcagagat   1380
cgttgaaaag ttcaccgaac ccggaacagt gatcagaatc aacgaagtcg tcgctgctct   1440
aaaggcttag aagcttgcgg ccgcactcga gtctggtaaa gaaaccgctg ctgcgaaatt   1500
tgaacgccag cacatggact cgtctactag aaataatttt gtttaacttt aagaaggaga   1560
tatacatatg gctagcatga ctggtggaca gcaaatgggt cgcggatcca tggcgttcga   1620
tctcaagact gaagacggcc tcatcacata tctcactaaa catctttctt tggacgtcga   1680
cacgagcgga gtgaagcgcc ttagcggagg ctttgtcaat gtaacctggc gcattaagct   1740
caatgctcct tatcaaggtc atacgagcat catcctgaag catgctcagc cgcacatgtc   1800
tacggatgag gattttaaga taggtgtaga acgttcggtt tacgaatacc aggctatcaa   1860
gctcatgatg gccaatcggg aggttctggg aggcgtggat ggcatagttt ctgtgccaga   1920
aggcctgaac tacgacttag agaataatgc attgatcatg caagatgtcg ggaagatgaa   1980
gaccctttta gattatgtca ccgccaaacc gccacttgcg acggatatag cccgccttgt   2040
tgggacagaa attgggggt tcgttgccag actccataac ataggccgcg agaggcgaga   2100
cgatcctgag ttcaaattct tctctggaaa tattgtcgga aggacgactt cagaccagct   2160
gtatcaaacc atcataccca acgcagcgaa atatggcgtc gatgacccct tgctgcctac   2220
tgtggttaag gaccttgtgg acgatgtcat gcacagcgaa gagacccttg tcatggcgga   2280
cctgtggagt ggaaatattc ttctccagtt ggaggaggga aacccatcga agctgcagaa   2340
gatatatatc ctggattggg aactttgcaa gtacggccca gcgtcgttgg acctgggcta   2400
tttcttgggt gactgctatt tgatatcccg ctttcaagac gagcaggtcg gtacgacgat   2460
gcggcaagcc tacttgcaaa gctatgcgcg tacgagcaag cattcgatca actacgccaa   2520
agtcactgca ggtattgctg ctcatattgt gatgtggacc gactttatgc agtgggggag   2580
cgaggaagaa aggataaatt ttgtgaaaaa gggggtagct gcctttcacg acgccagggg   2640
caacaacgac aatggggaaa ttacgtctac cttactgaag gaatcatcca ctgcgtaaaa   2700
gcttgcggcc gcactcgagt ctggtaaaga aaccgctgct gcgaaatttg aacgccagca   2760
catggactcg tctactagaa ataattttgt ttaactttaa gaaggagata tacatatggc   2820
tagcatgact ggtggacagc aaatgggtcg cggatccatg catatcagaa atccttaccg   2880
tacaccaatt gactatcaag cactttcaga ggccttccct cccctcaagc catttgtgtc   2940
tgtcaatgca gatggtacca gttctgttga cctcactatc ccagaagccc agagggcgtt   3000
cacggccgct cttcttcatc gtgacttcgg gctcaccatg accataccag aagaccgtct   3060
gtgcccaaca gtccccaata ggttgaacta cgttctgtgg attgaagata ttttcaacta   3120
```

cacgaacaaa accctcggcc tgtcggatga ccgtcctatt aaaggcgttg atattggtac 3180
aggagcctcc gcaatttatc ctatgcttgc ctgtgctcgg ttcaaggcat ggtctatggt 3240
tggaacagag gtcgagagga agtgcattga cacggcccgc ctcaatgtcg tcgcgaacaa 3300
tctccaagac cgtctctcga tattagagac atccattgat ggtcctattc tcgtccccat 3360
tttcgaggcg actgaagaat acgaatacga gtttactatg tgtaaccctc cattctacga 3420
cggtgctgcc gatatgcaga cttcggatgc tgccaaagga tttggatttg gcgtgggcgc 3480
tccccattct ggaacagtca tcgaaatgtc gactgaggga ggtgaatcgg ctttcgtcgc 3540
tcagatggtc cgtgagagct tgaagcttcg aacacgatgc agatggtaca cgagtaactt 3600
gggaaagctg aaatccttga aagaaatagt ggggctgctg aaagaacttg agataagcaa 3660
ctatgccatt aacgaatacg ttcaggggtc cacacgtcgt tatgccgttg cgtggtcttt 3720
cactgatatt caactgcctg aggagctttc tcgtccctct aaccccgagc tcagctctct 3780
tttctagctc gagtctggta aagaaaccgc tgctgcgaaa tttgaacgcc agcacatgga 3840
ctcgtctact agtcgcagct taattaacct aaactgctgc caccgctgag caataactag 3900
cataacccct tggggcctct aaacgggtct tgaggggttt tttgctagcg aaaggaggag 3960
tcgactatat ccggattggc gaatgggacg cgccctgtag cggcgcatta agcgcggcgg 4020
gtgtggtggt tacgcgcagc gtgaccgcta cacttgccag cgccctagcg cccgctcctt 4080
tcgctttctt cccttccttt ctcgccacgt tcgccggctt tccccgtcaa gctctaaatc 4140
gggggctccc tttagggttc cgatttagtg ctttacggca cctcgacccc aaaaaacttg 4200
attagggtga tggttcacgt agtgggccat cgccctgata gacggttttt cgccctttga 4260
cgttggagtc cacgttcttt aatagtggac tcttgttcca aactggaaca acactcaacc 4320
ctatctcggt ctattctttt gatttataag ggattttgcc gatttcggcc tattggttaa 4380
aaaatgagct gatttaacaa aaatttaacg cgaattttaa caaaatatta acgtttacaa 4440
tttctggcgg cacgatggca tgagattatc aaaaaggatc ttcacctaga tccttttaaa 4500
ttaaaaatga agttttaaat caatctaaag tatatatgag taaacttggt ctgacagtta 4560
ccaatgctta atcagtgagg cacctatctc agcgatctgt ctatttcgtt catccatagt 4620
tgcctgactc cccgtcgtgt agataactac gatacgggag ggcttaccat ctggccccag 4680
tgctgcaatg ataccgcgag acccacgctc accggctcca gatttatcag caataaacca 4740
gccagccgga agggccgagc gcagaagtgg tcctgcaact ttatccgcct ccatccagtc 4800
tattaattgt tgccgggaag ctagagtaag tagttcgcca gttaatagtt tgcgcaacgt 4860
tgttgccatt gctacaggca tcgtggtgtc acgctcgtcg tttggtatgg cttcattcag 4920
ctccggttcc caacgatcaa ggcgagttac atgatccccc atgttgtgca aaaaagcggt 4980
tagctccttc ggtcctccga tcgttgtcag aagtaagttg gccgcagtgt tatcactcat 5040
ggttatggca gcactgcata attctcttac tgtcatgcca tccgtaagat gcttttctgt 5100
gactggtgag tactcaacca agtcattctg agaatagtgt atgcggcgac cgagttgctc 5160
ttgcccggcg tcaatacggg ataataccgc gccacatagc agaactttaa aagtgctcat 5220
cattggaaaa cgttcttcgg ggcgaaaact ctcaaggatc ttaccgctgt tgagatccag 5280
ttcgatgtaa cccactcgtg cacccaactg atcttcagca tcttttactt tcaccagcgt 5340
ttctgggtga gcaaaaacag gaaggcaaaa tgccgcaaaa aagggaataa gggcgacacg 5400
gaaatgttga atactcatac tcttcctttt tcaatcatga ttgaagcatt tatcagggtt 5460
attgtctcat gagcggatac atatttgaat gtatttagaa aaataaacaa ataggtcatg 5520

-continued accaaaatcc cttaacgtga gttttcgttc cactgagcgt cagaccccgt agaaaagatc 5580
aaaggatctt cttgagatcc tttttttctg cgcgtaatct gctgcttgca aacaaaaaaa 5640
ccaccgctac cagcggtggt ttgtttgccg gatcaagagc taccaactct ttttccgaag 5700
gtaactggct tcagcagagc gcagatacca aatactgtcc ttctagtgta gccgtagtta 5760
ggccaccact tcaagaactc tgtagcaccg cctacatacc tcgctctgct aatcctgtta 5820
ccagtggctg ctgccagtgg cgataagtcg tgtcttaccg ggttggactc aagacgatag 5880
ttaccggata aggcgcagcg gtcgggctga acggggggtt cgtgcacaca gcccagcttg 5940
gagcgaacga cctacaccga actgagatac ctacagcgtg agctatgaga aagcgccacg 6000
cttcccgaag ggagaaaggc ggacaggtat ccggtaagcg gcagggtcgg aacaggagag 6060
cgcacgaggg agcttccagg gggaaacgcc tggtatcttt atagtcctgt cgggtttcgc 6120
cacctctgac ttgagcgtcg atttttgtga tgctcgtcag gggggcggag cctatggaaa 6180
aacgccagca acgcggcctt tttacggttc ctggcctttt gctggccttt tgctcacatg 6240
ttctttcctg cgttatcccc tgattctgtg gataaccgta ttaccgcctt tgagtgagct 6300
gataccgctc gccgcagccg aacgaccgag cgcagcgagt cagtgagcga ggaagcggaa 6360
gagcgcctga tgcggtattt tctccttacg catctgtgcg gtatttcaca ccgcatatat 6420
ggtgcactct cagtacaatc tgctctgatg ccgcatagtt aagccagtat acactccgct 6480
atcgctacgt gactgggtca tggctgcgcc ccgacacccg ccaacacccg ctgacgcgcc 6540
ctgacgggct tgtctgctcc cggcatccgc ttacagacaa gctgtgaccg tctccgggag 6600
ctgcatgtgt cagaggtttt caccgtcatc accgaaacgc gcgaggcagc tgcggtaaag 6660
ctcatcagcg tggtcgtgaa gcgattcaca gatgtctgcc tgttcatccg cgtccagctc 6720
gttgagtttc tccagaagcg ttaatgtctg gcttctgata aagcgggcca tgttaagggc 6780
ggtttttttcc tgtttggtca ctgatgcctc cgtgtaaggg ggatttctgt tcatgggggt 6840
aatgataccg atgaaacgag agaggatgct cacgatacgg gttactgatg atgaacatgc 6900
ccggttactg gaacgttgtg agggtaaaca actggcggta tggatgcggc gggaccagag 6960
aaaaatcact cagggtcaat gccagcgctt cgttaataca gatgtaggtg ttccacaggg 7020
tagccagcag catcctgcga tgcagatccg gaacataatg gtgcagggcg ctgacttccg 7080
cgtttccaga ctttacgaaa cacggaaacc gaagaccatt catgttgttg ctcaggtcgc 7140
agacgttttg cagcagcagt cgcttcacgt tcgctcgcgt atcggtgatt cattctgcta 7200
accagtaagg caaccccgcc agcctagccg ggtcctcaac gacaggagca cgatcatgct 7260
agtcatgccc cgcgcccacc ggaaggagct gactgggttg aaggctctca agggcatcgg 7320
tcgagatccc ggtgcctaat gagtgagcta acttacatta attgcgttgc gctcactgcc 7380
cgctttccag tcgggaaacc tgtcgtgcca gctgcattaa tgaatcggcc aacgcgcggg 7440
gagaggcggt ttgcgtattg ggcgccaggg tggtttttct tttcaccagt gagacgggca 7500
acagctgatt gcccttcacc gcctggccct gagagagttg cagcaagcgg tccacgctgg 7560
tttgccccag caggcgaaaa tcctgtttga tggtggttaa cggcgggata taacatgagc 7620
tgtcttcggt atcgtcgtat cccactaccg agatgtccgc accaacgcgc agcccggact 7680
cggtaatggc gcgcattgcg cccagcgcca tctgatcgtt ggcaaccagc atcgcagtgg 7740
gaacgatgcc ctcattcagc atttgcatgg tttgttgaaa accggacatg gcactccagt 7800
cgccttcccg ttccgctatc ggctgaattt gattgcgagt gagatattta tgccagccag 7860
ccagacgcag acgcgccgag acagaactta atgggcccgc taacagcgcg atttgctggt 7920
gacccaatgc gaccagatgc tccacgccca gtcgcgtacc gtcttcatgg gagaaaataa 7980
tactgttgat gggtgtctgg tcagagacat caagaaataa cgccggaaca ttagtgcagg 8040
cagcttccac agcaatggca tcctggtcat ccagcggata gttaatgatc agcccactga 8100
cgcgttgcgc gagaagattg tgcaccgccg ctttacaggc ttcgacgccg cttcgttcta 8160
ccatcgacac caccacgctg gcacccagtt gatcggcgcg agatttaatc gccgcgacaa 8220
tttgcgacgg cgcgtgcagg gccagactgg aggtggcaac gccaatcagc aacgactgtt 8280
tgcccgccag ttgttgtgcc acgcggttgg gaatgtaatt cagctccgcc atcgccgctt 8340
ccactttttc ccgcgttttc gcagaaacgt ggctggcctg gttcaccacg cgggaaacgg 8400
tctgataaga gacaccggca tactctgcga catcgtataa cgttactggt ttcacattca 8460
ccaccctgaa ttgactctct tccgggcgct atcatgccat accgcgaaag gttttgcgcc 8520
attcgatggt gtccgggatc tcgacgctct cccttatgcg actcctgcat taggaagcag 8580
cccagtagta ggttgaggcc gttgagcacc gccgccgcaa ggaatggtgc atgcaaggag 8640
atggcgccca acagtccccc ggccacgggg cctgccacca tacccacgcc gaaacaagcg 8700
ctcatgagcc cgaagtggcg agcccgatct tccccatcgg tgatgtcggc gatataggcg 8760
ccagcaaccg cacctgtggc gccggtgatg ccggccacga tgcgtccggc gtagcctagg 8820
atcgagatcg atctcgatcc cgcgaaat 8848

<210> SEQ ID NO 23
<211> LENGTH: 7774
<212> TYPE: DNA
<213> ORGANISM: Artificial Sequence
<220> FEATURE:
<223> OTHER INFORMATION: pETM6-C4-psiDK

<400> SEQUENCE: 23
taatacgact cactatcaag gaattgtgag cggataacaa ttcccctcta gaaataattt 60
tgtttaactt taagaaggag atatacatat ggctagcatg actggtggac agcaaatggg 120
tcgcggatcc atgcaggtga tacccgcgtg caactcggca gcaataagat cactatgtcc 180
tactcccgag tcttttagaa acatgggatg gctctctgtc agcgatgcgg tctacagcga 240
gttcatagga gagttggcta cccgcgcttc caatcgaaat tactccaacg agttcggcct 300
catgcaacct atccaggaat tcaaggcttt cattgaaagc gacccggtgg tgcaccaaga 360
atttattgac atgttcgagg gcattcagga ctctccaagg aattatcagg aactatgtaa 420
tatgttcaac gatatctttc gcaaagctcc cgtctacgga gaccttggcc ctcccgttta 480
tatgattatg gccaaattaa tgaacacccg agcgggcttc tctgcattca cgagacaaag 540
gttgaacctt cacttcaaaa aacttttcga tacctgggga ttgttcctgt cttcgaaaga 600
ttctcgaaat gttcttgtgg ccgaccagtt cgacgacaga cattgcggct ggttgaacga 660
gcgggccttg tctgctatgg ttaaacatta caatggacgc gcatttgatg aagtcttcct 720
ctgcgataaa aatgccccat actacggctt caactcttac gacgacttct ttaatcgcag 780
atttcgaaac cgagatatcg accgacctgt agtcggtgga gttaacaaca ccacccctcat 840 ttctgctgct tgcgaatcac tttcctacaa cgtctcttat gacgtccagt ctctcgacac 900
tttagttttc aaaggagaga cttattcgct taagcatttg ctgaataatg accctttcac 960
cccacaattc gagcatggga gtattctaca aggattcttg aacgtcaccg cttaccaccg 1020
atggcacgca cccgtcaatg ggacaatcgt caaaatcatc aacgttccag gtacctactt 1080

```
tgcgcaagcc ccgagcacga ttggcgaccc tatcccggat aacgattacg acccacctcc   1140
ttaccttaag tctcttgtct acttctctaa tattgccgca aggcaaatta tgtttattga   1200
agccgacaac aaggaaattg gcctcatttt ccttgtgttc atcggcatga ccgaaatctc   1260
gacatgtgaa gccacggtgt ccgaaggtca acacgtcaat cgtggcgatg acttgggaat   1320
gttccatttc ggtggttctt cgttcgcgct tggtctgagg aaggattgca gggcagagat   1380
cgttgaaaag ttcaccgaac ccggaacagt gatcagaatc aacgaagtcg tcgctgctct   1440
aaaggcttag aagcttgcgg ccgcactcga gtctggtaaa gaaaccgctg ctgcgaaatt   1500
tgaacgccag cacatggact cgtctactag aaataatttt gtttaacttt aagaaggaga   1560
tatacatatg gctagcatga ctggtggaca gcaaatgggt cgcggatcca tggcgttcga   1620
tctcaagact gaagacggcc tcatcacata tctcactaaa catctttctt tggacgtcga   1680
cacgagcgga gtgaagcgcc ttagcggagg ctttgtcaat gtaacctggc gcattaagct   1740
caatgctcct tatcaaggtc atacgagcat catcctgaag catgctcagc cgcacatgtc   1800
tacggatgag gattttaaga taggtgtaga acgttcggtt tacgaatacc aggctatcaa   1860
gctcatgatg gccaatcggg aggttctggg aggcgtggat ggcatagttt ctgtgccaga   1920
aggcctgaac tacgacttag agaataatgc attgatcatg caagatgtcg ggaagatgaa   1980
gaccctttta gattatgtca ccgccaaacc gccacttgcg acggatatag cccgccttgt   2040
tgggacagaa attgggggt tcgttgccag actccataac ataggccgcg agaggcgaga   2100
cgatcctgag ttcaaattct tctctggaaa tattgtcgga aggacgactt cagaccagct   2160
gtatcaaacc atcataccca acgcagcgaa atatggcgtc gatgacccct tgctgcctac   2220
tgtggttaag gaccttgtgg acgatgtcat gcacagcgaa gagacccttg tcatggcgga   2280
cctgtggagt ggaaatattc ttctccagtt ggaggaggga aacccatcga agctgcagaa   2340
gatatatatc ctggattggg aactttgcaa gtacggccca gcgtcgttgg acctgggcta   2400
tttcttgggt gactgctatt tgatatcccg ctttcaagac gagcaggtcg gtacgacgat   2460
gcggcaagcc tacttgcaaa gctatgcgcg tacgagcaag cattcgatca actacgccaa   2520
agtcactgca ggtattgctg ctcatattgt gatgtggacc gactttatgc agtgggggag   2580
cgaggaagaa aggataaatt ttgtgaaaaa gggggtagct gcctttcacg acgccagggg   2640
caacaacgac aatggggaaa ttacgtctac cttactgaag gaatcatcca ctgcgtaaaa   2700
gcttgcggcc gcactcgagt ctggtaaaga aaccgctgct gcgaaatttg aacgccagca   2760
catggactcg tctactagtc gcagcttaat taacctaaac tgctgccacc gctgagcaat   2820
aactagcata accccttggg gcctctaaac gggtcttgag gggttttttg ctagcgaaag   2880
gaggagtcga ctatatccgg attggcgaat gggacgcgcc ctgtagcggc gcattaagcg   2940
cggcgggtgt ggtggttacg cgcagcgtga ccgctacact tgccagcgcc ctagcgcccg   3000
ctcctttcgc tttcttccct tcctttctcg ccacgttcgc cggctttccc cgtcaagctc   3060
taaatcgggg gctcccttta gggttccgat ttagtgcttt acggcacctc gaccccaaaa   3120
aacttgatta gggtgatggt tcacgtagtg ggccatcgcc ctgatagacg gtttttcgcc   3180
ctttgacgtt ggagtccacg ttctttaata gtggactctt gttccaaact ggaacaacac   3240
tcaaccctat ctcggtctat tcttttgatt tataagggat tttgccgatt tcggcctatt   3300
ggttaaaaaa tgagctgatt taacaaaaat ttaacgcgaa ttttaacaaa atattaacgt   3360
ttacaatttc tggcggcacg atggcatgag attatcaaaa aggatcttca cctagatcct   3420
```

tttaaattaa aaatgaagtt ttaaatcaat ctaaagtata tatgagtaaa cttggtctga 3480
cagttaccaa tgcttaatca gtgaggcacc tatctcagcg atctgtctat ttcgttcatc 3540
catagttgcc tgactccccg tcgtgtagat aactacgata cgggagggct taccatctgg 3600
ccccagtgct gcaatgatac cgcgagaccc acgctcaccg gctccagatt tatcagcaat 3660
aaaccagcca gccggaaggg ccgagcgcag aagtggtcct gcaactttat ccgcctccat 3720
ccagtctatt aattgttgcc gggaagctag agtaagtagt tcgccagtta atagtttgcg 3780
caacgttgtt gccattgcta caggcatcgt ggtgtcacgc tcgtcgtttg gtatggcttc 3840
attcagctcc ggttcccaac gatcaaggcg agttacatga tcccccatgt tgtgcaaaaa 3900
agcggttagc tccttcggtc ctccgatcgt tgtcagaagt aagttggccg cagtgttatc 3960
actcatggtt atggcagcac tgcataattc tcttactgtc atgccatccg taagatgctt 4020
ttctgtgact ggtgagtact caaccaagtc attctgagaa tagtgtatgc ggcgaccgag 4080
ttgctcttgc ccggcgtcaa tacgggataa taccgcgcca catagcagaa ctttaaaagt 4140
gctcatcatt ggaaaacgtt cttcggggcg aaaactctca aggatcttac cgctgttgag 4200
atccagttcg atgtaaccca ctcgtgcacc caactgatct tcagcatctt ttactttcac 4260
cagcgtttct gggtgagcaa aaacaggaag gcaaaatgcc gcaaaaaagg gaataagggc 4320
gacacggaaa tgttgaatac tcatactctt cctttttcaa tcatgattga agcatttatc 4380
agggttattg tctcatgagc ggatacatat ttgaatgtat ttagaaaaat aaacaaatag 4440
gtcatgacca aaatccctta acgtgagttt tcgttccact gagcgtcaga ccccgtagaa 4500
aagatcaaag gatcttcttg agatcctttt tttctgcgcg taatctgctg cttgcaaaca 4560
aaaaaaccac cgctaccagc ggtggtttgt ttgccggatc aagagctacc aactcttttt 4620
ccgaaggtaa ctggcttcag cagagcgcag ataccaaata ctgtccttct agtgtagccg 4680
tagttaggcc accacttcaa gaactctgta gcaccgccta catacctcgc tctgctaatc 4740
ctgttaccag tggctgctgc cagtggcgat aagtcgtgtc ttaccgggtt ggactcaaga 4800
cgatagttac cggataaggc gcagcggtcg ggctgaacgg ggggttcgtg cacacagccc 4860
agcttggagc gaacgaccta caccgaactg agatacctac agcgtgagct atgagaaagc 4920
gccacgcttc ccgaagggag aaaggcggac aggtatccgg taagcggcag ggtcggaaca 4980
ggagagcgca cgagggagct tccaggggga aacgcctggt atctttatag tcctgtcggg 5040
tttcgccacc tctgacttga gcgtcgattt ttgtgatgct cgtcaggggg gcggagccta 5100
tggaaaaacg ccagcaacgc ggccttttta cggttcctgg ccttttgctg gccttttgct 5160
cacatgttct ttcctgcgtt atcccctgat tctgtggata accgtattac cgcctttgag 5220
tgagctgata ccgctcgccg cagccgaacg accgagcgca gcgagtcagt gagcgaggaa 5280
gcggaagagc gcctgatgcg gtattttctc cttacgcatc tgtgcggtat ttcacaccgc 5340
atatatggtg cactctcagt acaatctgct ctgatgccgc atagttaagc cagtatacac 5400
tccgctatcg ctacgtgact gggtcatggc tgcgccccga cacccgccaa cacccgctga 5460
cgcgccctga cgggcttgtc tgctcccggc atccgcttac agacaagctg tgaccgtctc 5520
cgggagctgc atgtgtcaga ggttttcacc gtcatcaccg aaacgcgcga ggcagctgcg 5580
gtaaagctca tcagcgtggt cgtgaagcga ttcacagatg tctgcctgtt catccgcgtc 5640
cagctcgttg agtttctcca gaagcgttaa tgtctggctt ctgataaagc gggccatgtt 5700
aagggcggtt ttttcctgtt tggtcactga tgcctccgtg taagggggat ttctgttcat 5760
gggggtaatg ataccgatga aacgagagag gatgctcacg atacgggtta ctgatgatga 5820

-continued

| | | | | | | |
|---|---|---|---|---|---|---|
| acatgcccgg | ttactggaac | gttgtgaggg | taaacaactg | gcggtatgga | tgcggcggga | 5880 |
| ccagagaaaa | atcactcagg | gtcaatgcca | gcgcttcgtt | aatacagatg | taggtgttcc | 5940 |
| acagggtagc | cagcagcatc | ctgcgatgca | gatccggaac | ataatggtgc | agggcgctga | 6000 |
| cttccgcgtt | tccagacttt | acgaaacacg | gaaaccgaag | accattcatg | ttgttgctca | 6060 |
| ggtcgcagac | gttttgcagc | agcagtcgct | tcacgttcgc | tcgcgtatcg | gtgattcatt | 6120 |
| ctgctaacca | gtaaggcaac | cccgccagcc | tagccgggtc | ctcaacgaca | ggagcacgat | 6180 |
| catgctagtc | atgccccgcg | cccaccggaa | ggagctgact | gggttgaagg | ctctcaaggg | 6240 |
| catcggtcga | gatcccggtg | cctaatgagt | gagctaactt | acattaattg | cgttgcgctc | 6300 |
| actgcccgct | ttccagtcgg | gaaacctgtc | gtgccagctg | cattaatgaa | tcggccaacg | 6360 |
| cgcggggaga | ggcggtttgc | gtattgggcg | ccagggtggt | ttttcttttc | accagtgaga | 6420 |
| cgggcaacag | ctgattgccc | ttcaccgcct | ggccctgaga | gagttgcagc | aagcggtcca | 6480 |
| cgctggtttg | ccccagcagg | cgaaaatcct | gtttgatggt | ggttaacggc | gggatataac | 6540 |
| atgagctgtc | ttcggtatcg | tcgtatccca | ctaccgagat | gtccgcacca | acgcgcagcc | 6600 |
| cggactcggt | aatggcgcgc | attgcgccca | gcgccatctg | atcgttggca | accagcatcg | 6660 |
| cagtgggaac | gatgccctca | ttcagcattt | gcatggtttg | ttgaaaaccg | gacatggcac | 6720 |
| tccagtcgcc | ttcccgttcc | gctatcggct | gaatttgatt | gcgagtgaga | tatttatgcc | 6780 |
| agccagccag | acgcagacgc | gccgagacag | aacttaatgg | gcccgctaac | agcgcgattt | 6840 |
| gctggtgacc | caatgcgacc | agatgctcca | cgcccagtcg | cgtaccgtct | tcatgggaga | 6900 |
| aaataatact | gttgatgggt | gtctggtcag | agacatcaag | aaataacgcc | ggaacattag | 6960 |
| tgcaggcagc | ttccacagca | atggcatcct | ggtcatccag | cggatagtta | atgatcagcc | 7020 |
| cactgacgcg | ttgcgcgaga | agattgtgca | ccgccgcttt | acaggcttcg | acgccgcttc | 7080 |
| gttctaccat | cgacaccacc | acgctggcac | ccagttgatc | ggcgcgagat | ttaatcgccg | 7140 |
| cgacaatttg | cgacggcgcg | tgcagggcca | gactggaggt | ggcaacgcca | atcagcaacg | 7200 |
| actgtttgcc | cgccagttgt | tgtgccacgc | ggttgggaat | gtaattcagc | tccgccatcg | 7260 |
| ccgcttccac | tttttcccgc | gttttcgcag | aaacgtggct | ggcctggttc | accacgcggg | 7320 |
| aaacggtctg | ataagagaca | ccggcatact | ctgcgacatc | gtataacgtt | actggtttca | 7380 |
| cattcaccac | cctgaattga | ctctcttccg | ggcgctatca | tgccataccg | cgaaaggttt | 7440 |
| tgcgccattc | gatggtgtcc | gggatctcga | cgctctccct | tatgcgactc | ctgcattagg | 7500 |
| aagcagccca | gtagtaggtt | gaggccgttg | agcaccgccg | ccgcaaggaa | tggtgcatgc | 7560 |
| aaggagatgg | cgcccaacag | tcccccggcc | acggggcctg | ccaccatacc | cacgccgaaa | 7620 |
| caagcgctca | tgagcccgaa | gtggcgagcc | cgatcttccc | catcggtgat | gtcggcgata | 7680 |
| taggcgccag | caaccgcacc | tgtggcgccg | gtgatgccgg | ccacgatgcg | tccggcgtag | 7740 |
| cctaggatcg | agatcgatct | cgatcccgcg | aaat | | | 7774 |